United States Patent [19]

Höger et al.

[11] Patent Number: 5,756,697
[45] Date of Patent: May 26, 1998

[54] SUBUNITS OF GLUTAMATE RECEPTORS, THEIR PREPARATION AND THEIR USE

[75] Inventors: Thomas Höger, Edingen-Neckarhausen; Andreas Ultsch, Mannheim; Alfred Bach, Heidelberg; Sylvia Sterrer, Rellingen; Hans-Georg Lemaire, Limburgerhof, all of Germany

[73] Assignee: BASF Aktiengesellschaft, Ludwigshafen, Germany

[21] Appl. No.: 687,379

[22] PCT Filed: Jan. 27, 1995

[86] PCT No.: PCT/EP95/00290

§ 371 Date: Aug. 5, 1996

§ 102(e) Date: Aug. 5, 1996

[87] PCT Pub. No.: WO95/21188

PCT Pub. Date: Aug. 10, 1995

[30] Foreign Application Priority Data

Feb. 7, 1994 [DE] Germany .................. 44 03 666.3

[51] Int. Cl.⁶ .................. C07H 21/02; C07H 21/04
[52] U.S. Cl. .................. 536/23.1; 536/243; 530/350
[58] Field of Search .................. 536/23.1, 24.3; 530/350; 514/44; 435/69.1, 6

[56] References Cited

U.S. PATENT DOCUMENTS

| 5,202,257 | 4/1993 | Heinemann et al. | 435/252.3 |
| 5,385,831 | 1/1995 | Mulvihill et al. | 435/69.1 |
| 5,521,297 | 5/1996 | Daggett et al. | 536/23.5 |
| 5,547,855 | 8/1996 | Kamboj et al. | 435/69.1 |
| 5,585,479 | 12/1996 | Hoke et al. | 536/24.5 |

FOREIGN PATENT DOCUMENTS

| 568 384 | 11/1993 | European Pat. Off. |
| 574 257 | 12/1993 | European Pat. Off. |

OTHER PUBLICATIONS

J. NeuroScience, vol. 12, 1010–23, 1992.
Science, vol. 249, 556–60 (1990).
Nature, vol. 342, 643–48 (1989).
Poc. Natl. Acad. Sci. vol. 88, 7557–61 (1991).
Proc. Natl. Acad. Sci., vol. 89, 1443–47 (1992).

*Primary Examiner*—W. Gary Jones
*Assistant Examiner*—Ethan Whisenant
*Attorney, Agent, or Firm*—Keil & Weinkauf

[57] ABSTRACT

The invention relates to novel subunits for glutamate receptors and to the DNA sequences coding therefor, and to processes for preparing DNA sequences and receptors. The invention furthermore relates to methods for identifying functional ligands for these receptors.

5 Claims, No Drawings

SUBUNITS OF GLUTAMATE RECEPTORS, THEIR PREPARATION AND THEIR USE

This application is a 371 of PCT/EP95/00290 filed 27 Jan. 95, published as WO95/21188 Aug. 10, 1995. The invention relates to the expression of novel variants of ionotropic glutamate receptor subunits in eukaryotic cells and to methods for finding functional ligands for corresponding glutamate receptor channels.

Glutamate is the most important excitatory neurotransmitter in the central nervous system (TIPS 11, 1990, 126–132; Pharmacological Reviews 40, 1989, 143–210; TIPS 13, 1992, 291–296) and is involved in numerous pathophysiological processes such as epilepsy, schizophrenia, ischemia. Glutamate receptors are therefore potential sites of attack for appropriate drugs.

To date, the primary structure has been elucidated for some subunits of AMPA, kainate and NMDA receptors and some metabotropic receptors (Nature 342, 1989, 643; Science 249, 1990, 556; Neuron 8, 1992, 169; Science 256, 1992, 1217; Nature 358, 1992, 36).

Four AMPA-glutamate receptor subunits of the rat have hitherto been described in the literature, GluRA, GluRB, GluRC and GluRD, each of which occurs in two splicing variants "flip" and "flop" (Science 249, 1990, 1580). In addition, RNA editing which affects the Q/R site of the second transmembrane domain has been shown for mouse and rat GluRB. These two GluRB variants differ considerably in their electrophysiological properties (Cell 67, 1991, 11–19; Neuron 8; 1992, 189–198). The human cDNA for GluRAflip and GluRAflop has likewise been published (PNAS U.S.A. 88, 1991, 7557–7561; PNAS USA 89, 1992, 1443–1447).

We have now found variants of the human glutamate receptor subunits A, B, C and D, as well as DNA sequences which code for such subunits. These subunits lead to GluR channels with specific electrophysiological properties.

We have found that the first amino acid of the flip/flop region of GluRA, GluRB, GluRC and GluRD can be in the form of glycine (G) or arginine (R) due to RNA editing. The names of the corresponding subunits are as follows:
GluRAflipG, GluRAflipR, GluRAflopG, GluRAflopR
GluRBflipQ-G, GluRBflipQ-R, GluRBflopQ-G, GluRBflopQ-R
GluRBflipR-G, GluRBflipR-R, GluRBflopR-G, GluRBflopR-R
GluRCflipG, GluRCflipR, GluRCflopG, GluRCflopR
GluRDflipG, GluRDflipR, GluRDflopG, GluRDflopR In the case of GluRB the RNA editing known for the rat has been taken into account in the naming of the corresponding variants.

Furthermore, a variant of GluRA produced by alternative splicing, in which a 240 bp fragment is missing in the 5' region of the GluRA cDNA and thus the corresponding protein is truncated by 80 amino acids, has been found. The names of the corresponding subunits are as follows:
GluRAdel240flipG, GluRAdel240flipR, GluRAdel240flopG, GluRAdel240flopR The following DNA and amino-acid sequences all relate to human glutamate receptor subunits.

SEQ ID NO: 1 depicts the cDNA sequence of GluRAflipG and the polypeptide sequence (SEQ ID NO: 2) derived therefrom;

SEQ ID NO: 3 depicts the cDNA sequence of GluRAflopG, and

SEQ ID NO: 4 depicts the polypeptide sequence derived therefrom.

Compared with the GluRAflipG cDNA, the GluRAflipR cDNA has a base exchange at position bp 2269 which converts a glycine codon (GGA) into an arginine codon (AGA). A corresponding statement applies to GluRAflopR.

The GluRAdel240 variants correspond to the said GluRA variants but have a deletion: bp 221–460 relative to SEQ ID NO: 1 and 3.

SEQ ID NO: 5 depicts the cDNA sequence of GluRBflipQ-G and the polypeptide sequence derived therefrom (SEQ ID NO: 6); SEQ ID NO: 7 depicts the cDNA sequence of GluRBflopQ-G, and SEQ ID NO: 8 depicts the polypeptide sequence derived therefrom.

Compared with GluRBflipQ-G, the cDNA for GluRBflipQ-R has a base exchange at position bp 2290 which converts a glycine codon (GGA) into an arginine codon (AGA). A corresponding statement applies to GluRBflopQ-R.

Compared with the abovementioned GluRB variants, the cDNA molecules for GluRBflipR-G, GluRBflipR-R, GluRBflopR-G and GluRBflopR-R have a base exchange at position bp 1820 which converts a glutamine codon (CAG) into an arginine codon (CGG).

SEQ ID NO: 9 depicts the cDNA sequence of GluRCflipG and

SEQ ID NO: 10 depicts the polypeptide sequence derived therefrom.

SEQ ID NO: 11 shows the cDNA sequence of GluRCflopG and

SEQ ID NO: 12 depicts the polypeptide sequence derived therefrom.

Compared with GluRCflipG and GluRCflopG, respectively, the cDNA molecules for GluRCflipR and GluRCflopR have a base exchange at position bp 2377 which converts a glycine codon (GGA) into an arginine codon (AGA).

SEQ ID NO: 13 depicts the cDNA sequence of GluRDflipG and

SEQ ID NO: 14 depicts the polypeptide sequence derived therefrom.

SEQ ID NO: 15 shows the cDNA sequence of GluRDflopG and

SEQ ID NO: 16 depicts the polypeptide sequence derived therefrom.

Compared with GluRDflipG and GluRDflopG, respectively, the cDNA molecules for GluRDflipR and GluRDflopR have a base exchange at position bp 2293 which converts a glycine codon (GGA) into an arginine codon (AGA).

Other suitable DNA sequences are those which although they have a different nucleotide sequence from that detailed in SEQ ID NO: 1, 3, 5, 7, 9, 11, 13 or 15 code for the polypeptide chain detailed in SEQ ID NO: 2, 4, 6, 8, 10, 12, 14 or 16, or parts thereof as a consequence of the degeneracy of the genetic code. Also suitable are those DNA sequences which code for AMPA-glutamate receptor subunits and which hybridize under standard conditions with the nucleotide sequence depicted in SEQ ID NO: 1, 3, 5, 7, 9, 11, 13 or 15 or with a nucleotide sequence which codes for the protein depicted in SEQ ID NO: 2, 4, 6, 8, 10, 12, 14 or 16. Standard conditions mean, for example, temperatures of from 42° to 58° C. in an aqueous buffer solution with a concentration of from 0.1 to 1×SSC (1×SSC: 0.15M NaCl, 15 mM sodium citrate pH 7.2). The experimental conditions for DNA hybridization are described in textbooks of genetic manipulation, for example in Sambrook et al., Molecular Cloning, Cold Spring Harbor Laboratory, 1989.

We have furthermore found genetic engineering processes for preparing these subunits. We have additionally found that the DNA sequences coding for these receptor subunits can be used to find functional ligands for these receptors. The invention furthermore relates to methods for identifying functional ligands for AMPA-glutamate receptors, which comprise transfecting cells with sequences which code for AMPA-GluR subunits, isolating the membranes of these cells, and carrying out conventional receptor-binding experiments with these membranes.

Another method according to the invention for identifying functional ligands for AMPA-glutamate receptors comprises causing in cells which have been transfected with one or more DNA sequences which code for AMPA-GluR subunits an effect on the signal transduction pathway due to binding of the ligands to the receptor, which is detected by a receptor system, for example the intracellular $Ca^{++}$ concentration after ligand binding by fluorimetric methods (Anal. Biochem. 209, 1993, 343).

The novel polypeptides and DNA sequences can be prepared by using conventional methods of genetic engineering. Thus, mRNA can be isolated from brain tissue and converted into double-stranded cDNA. This cDNA can be used as template for the polymerase chain reaction. It is thus possible by using specific primers under suitable reaction conditions to amplify the appropriate cDNA. The use of suitable primers makes it possible to sequence the amplified cDNA without previous cloning. The double-stranded cDNA can also be integrated in $\lambda$ vectors, eg. $\lambda$ gt 10 or $\lambda$ ZAP, in order to generate a brain-specific cDNA bank. A cDNA bank of this type can be screened with radiolabeled DNA or RNA probes in order to identify clones which display homology with the hybridization probe. The methods used for this are described, for example, in Current Protocols in Molecular Biology (edited by F. M. Ausubel et al.) 1989, ISBN 0-471 50338-x (Vol. 1 and 2), for the polymerase chain reaction in Saiki et al., Science, 230 (1985) 1350–54 and Mullis and Faloona, Meth. Enzymol., 155 (1987) 335–350.

The cDNA characterized in this way can easily be obtained using restriction enzymes. The fragments resulting from this can be used, where appropriate in conjunction with chemically synthesized oligonucleotides, adaptors or gene fragments, to clone the sequences coding for the protein. Incorporation of the gene fragments or synthetic DNA sequences into cloning vectors, e.g. the commercial plasmids M13mp18 or Bluescript, is carried out in a conventional way. The genes or gene fragments can also be provided with suitable control regions which have been chemically synthesized or isolated from bacteria, phages, eukaryotic cells or their viruses and which make it possible to express the proteins in various host systems.

The transformation or transfection of suitable host organisms with hybrid plasmids has likewise been described in detail (M. Wigler et al., Cell, 16 (1979), 777–785; F. L. Graham and A. J. van der Eb, Virology, 52 (1973), 456–467).

On expression in mammalian cells it is possible to use vectors which place the gene to be expressed, in this case the cDNA sequences coding for the AMPA-glutamate receptor subunits described herein, under the control of the mouse metallothionein, the viral SV40 or the cytomegalovirus promoter (J. Page Martin, Gene, 37 (1985), 139–144). Needed for expression is the presence of the methionine start codon of the gene which codes for these subunits of AMPA-glutamate receptors. Clones which have copies of these vectors as episomes or integrated into the genome are then isolated. It is particularly advantageous to integrate the foreign gene into a vector which contains the cytomegalovirus promoter.

As an alternative to this, cells can be transfected with a suitable vector in such a way that the transient expression of the DNA introduced in this way is sufficient for pharmacological characterization of the expressed heterologous polypeptides. In this case too, control of expression by the cytomegalovirus promoter is particularly advantageous.

It is furthermore possible to prepare functional AMPA-glutamate receptors by transfecting one or more different DNA sequences from the group of AMPA-GluR subunits together into cells. AMPA-glutamate receptors with different subunits can be obtained in this way.

The use of shuttle vectors is very suitable in conjunction with prokaryotic sequences which code for replication in bacterial cells and antibiotic resistance. The construction and replication of the plasmid take place initially in bacterial cells; this is followed by transfer into eukaryotic cells, e.g. into the human embryonic kidney cell line HEK 293.

It is also possible to use other cell systems, e.g. yeast and other fungi, insect cells as well as animal and human cells such as CHO, COS and L cells in conjunction with suitable expression vectors for the expression of the cloned cDNA.

The eukaryotic expression systems have the advantage that they are able to express their products efficiently and usually in native form. They have furthermore the ability to carry out post-translational modification of their products.

The expressed receptor proteins can be solubilized by detergents and purified by affinity chromatography by conventional methods. The pure polypeptide can, after crystallization and X-ray structural analysis or other physical methods such as NMR or scanning tunneling microscopy, be used to elucidate first the spatial structure of the receptor and then the spatial structure of the ligand binding site.

The expressed receptor proteins can, after appropriate purification, also be used as antigens for generating polyclonal or monoclonal antibodies. These antibodies in turn can be used where appropriate for diagnostic purposes. Another possible use of such antibodies is as aids to rational drug design. Thus, the receptor-specific antibodies can be employed as antigen for generating anti-idiotype antibodies. Such antibodies may represent an image of defined regions of the receptor and be used for screening for specific receptor ligands or for rational drug design.

Receptor-expressing cell lines represent an important instrument in screening for specific receptor ligands. The membranes of these cells can be used for a receptor binding assay for this purpose. Information about the mode of action (agonism/antagonism) of a receptor ligand can be obtained by providing cells, which have been transfected with a DNA sequence according to the invention, with a suitable reporter system. Suitable reporter systems are those in which a promoter which is regulated by compounds of the signal transduction pathway (second messenger) is functionally connected to a gene for a product which can easily be detected, such as luciferase. Such reporter systems are disclosed, for example, in Science 252, (1991) 1424, Proc. Natl. Acad. Sci. U.S.A. 88 (1991) 5061 or Journal of Receptor Res. 13, (1993) 79. A suitable promoter which is, for example, regulated by the intracellular $Ca^{++}$ concentration is that of the fos gene. It is also possible to detect changes in the intracellular $Ca^{++}$ concentration directly using fluorescent dyes, eg. FURA 2AM.

Furthermore, the current flowing through the cell membrane as a function of the ligand binding can be measured.

Because of the degeneracy of the genetic code, it is possible to use DNA sequences other than those described here, e.g. chemically synthesized genes with a different DNA sequence, for the expression of the described subunits of human AMPA-glutamate receptors.

The invention makes it possible to identify and characterize substances which bind to the receptor described herein and there have an agonistic or antagonistic action.

The invention furthermore relates to the use of oligonucleotides which are derived from the structure described in SEQ ID NO: 1, 3, 5, 7, 9, 11, 13 or 15 as antisense molecules for switching off genes in a targeted manner.

The invention also makes it possible to prepare synthetic oligonucleotides with which the expression of AMPA-glutamate receptor subunits can be specifically inhibited by intracerebroventricular administration, as has been described, for example, for NMDA receptors (Nature 363, 1993, 260).

Other embodiments of the invention are described in detail in the examples.

For genetic engineering methods, reference may be made, for example, to the handbook by Sambrook et al., Molecular Cloning, Cold Spring Harbor Laboratory, 1989, or DNA cloning, Vol. I to III, IRl Press 1985 to 1987, edited by D. M. Glover.

EXAMPLE 1

Isolation of CDNA molecules which code for the human AMPA-glutamate receptor subunits GluRA and GluRAdel240.

The polymerase chain reaction (PCR) technique was used to amplify three cDNA fragments which are specific for the human AMPA-glutamate receptor subunit GluRA from two commercially available human brain cDNA libraries. To increase the specificity of amplification, the 2-stage PCR method described hereinafter was carried out: in each case 10 µl of lysate from a human temporal cortex cDNA library (titer: $1.5 \times 10^{11}$ phages/ml; vector lambda ZAP; GluRA cDNA fragment bp 1–839) or a human nucleus accumbens cDNA library (titer: $1-9 \times 10^9$ phages/ml; vector lambda gt10; GluRA cDNA fragments 1–1421 and 1407–2721) were used as templates for the first PCR reaction with the primer oligonucleotides A and B. The volumes of the reaction mixtures were 100 µl in each case, 20 pmol of each of the various primers were employed, and the reaction buffer contained 10 mM tris-HCl pH 8.5, 50 mM KCl, 1.5 mM $MgCl_2$, and 0.2 mM each of DATP, dCTP, dGTP and dTTP. 20 cycles with the following temperature profile were carried out: 94° C. for 1 minute, 55° C. for 1 minute, 72° C. for 1 minute. A Perkin-Elmer type 9600 thermocycler was used.

After the PCR had been carried out, in each case 10 µl of the PCR mixtures were removed and used as templates for a second PCR with primers C and D. The reaction and buffer conditions were the same as for the first PCR, but the number of cycles was increased to 35. The amplified cDNA fragments were cloned into the vector pCRII in accordance with the manufacturer's instructions using the Invitrogen TA cloning kit.

The primer oligonucleotides for amplification of the human GluRA cDNA fragment which comprises base pairs 1–1431 had the following sequences:

Primer A: 5'-ATCTATGATTGGACCTGGGC-3' (SEQ ID NO: 17)

Primer B: 5'-ACATCTGCTCTTCCATAGACCAGC-3' (SEQ ID NO: 18)

Primer C: 5'-TGCGATAAGCTTATGCAGCACATTTTT GCCTTCTTCTGC-3' (SEQ ID NO: 19)

Primer D: 5'-ATGCCATTCCAGGCCTTCGTGTCA-3' (SEQ ID NO: 20)

The primer oligonucleotides for amplification of the human GluRA cDNA fragment which comprises base pairs 1407–2721 had the following sequences:

Primer A: 5'-GATGGAAAATACGGAGCCCGA-3' (SEQ ID NO: 21)

Primer B: 5'-GCTGGGGAGCCGAGCCTGCTC-3' (SEQ ID NO: 22)

Primer C: 5'-TGACACGAAGGCCTGGAATGGCAT-3' (SEQ ID NO: 23)

Primer D: 5'-TGCGATGAATTCTTACAATCCCGTGG CTCCCAAGGGCAT-3' (SEQ ID NO: 24)

The primer oligonucleotides for amplification of the human GluRA cDNA fragment which comprises base pairs 1–839 had the following sequences:

Primer A: SEQ ID NO: 17

Primer B: 5'-TACTTGGGTCTCTTCCAGTCCA-3' (SEQ ID NO: 25)

Primer C: SEQ ID NO: 20

Primer D: 5'-TGTGTGGTCTCGAGCATCACTATT-3' (SEQ ID NO: 26)

Standard methods of genetic engineering (see, for example, Sambrook et al. (1989), Molecular Cloning, Cold Spring Harbor Laboratory) were used to assemble the amplified cDNA fragments in each case to the complete coding regions of GluRA and GluRAdel240.

EXAMPLE 2

Isolation of cDNA molecules for human glutamate receptor subunits A, B, C and D cDNA fragments which are specific for human glutamate receptor subunits A, B, C and D were obtained by screening the following commercially available human brain cDNA libraries:

Hippocampus (from Stratagene)

Cerebellum (from Clontech and Stratagene)

Nucleus accumbens (Clontech)

The screening probes used were PCR fragments 600–3000 bp in size which had been amplified from the cDNA molecules for rat GluRA, B, C and D which had been cloned in pBluescript. In each case 1 ng of plasmid DNA was employed as template. The primer concentrations and buffer conditions for the PCRs corresponded to those in Example 1 but in each case 2 µl of the dNTP labeling mixture from the Boehringer Mannheim DNA labeling and detection kit were employed as nucleotide source. 35 cycles with the following temperature profile were carried out: 94° C. for 2 minutes, 55° C. for 2 minutes, 72° C. for 3 minutes. The Dig-dUTP-labeled fragments were purified on a Seaplaque agarose gel. The screening procedure was carried out in accordance with the instructions in the manual for the abovementioned kit. The GluR cDNA fragments of the lambda clones derived from the screening were cloned by conventional methods of genetic engineering into the vector pBluescript and assembled to give the complete cDNA molecules of the various GluR variants.

EXAMPLE 3

Transient expression of the cloned human GluR genes in HEK293 cells.

Unless stated otherwise, the cell culture was carried out as described by Lindl and Bauer, Zell-und Gewebekultur, Gustav Fischer Verlag.

The GluR cDNA molecules from Examples 1 and 2 were cloned into conventional plasmids such as pBluescript (from Stratagene) and PCRII (from Invitrogen) during their isolation. The cloned GluR fragments in each case comprise the entire open reading frame including start and stop codons and at least 40 bp of the 5' non-translated region preceding the start codon.

For the transient expression in eukaryotic cell lines, the cloned GluR fragments were cloned into the expression vector pcDNA3 (from Invitrogen). The recombinant plasmids resulting therefrom were replicated in a known manner.

HEK 293 cells were cultivated under standard conditions. After trypsinization, the cells were taken up in DMEM (Gibco) which contained 3.7 g/l $NaHCO_3$, and 10 cm Petri dishes were inoculated with $1.5 \times 10^6$ cells. These cells were then cultivated at 37° C. and 5% $CO_2$ for 24 h.

The DNA to be transfected was prepared as follows: 20 µg of the DNA solution (1 mg/ml), purified using the Quiagen® system from Diagen, were mixed with 437 µl of $H_2O$, and then 62.5 µl of 2M $CaCl_2$, and finally 500 µl of PBS, were added. $Ca^{++}$ precipitates formed within 10 min at room temperature.

The solution was placed on a 10 cm culture dish containing the HEK 293 cells cultivated by the above method. After cautious mixing, the cells were cultivated in an incubator at 37° C./3% $CO_2$ for 15 to 20 h. Then 5 ml of serum-free medium were cautiously added. After removal of all the medium and repetition of the washing process with 5 ml of medium, 10 ml of medium were added to the cells. After incubation at 37° C. and 5% $CO_2$ for 48 h, the cells were suitable for pharmacologial and electrophysiological investigations.

Alternatively, the DNA was also introduced into the cells with liposome mediation. Lipofectin from GIBCO-BRL was employed for this in accordance with the manufacturer's instructions.

EXAMPLE 4
Expression of the AMPA-glutamate receptor subunits in oocytes

To prepare cRNA, the corresponding cDNA molecules which code for the glutamate receptor subunits were cloned by standard protocols into the Bluescript plasmid (Stratagene) which had been cleaved with EcoRI.

Plasmid DNA was obtained by standard methods after growing of the Bluescript clones which code for subunits of AMPA-glutamate receptors. This plasmid DNA was cleaved with the restriction enzyme Not I and employed for the in vitro transcription. The transcription was started from the T3 or T7 promoter and carried out under standard conditions in accordance with the Stratagene in vitro transcription kit.

For the expression of the receptor subunits, in each case 10 ng of cRNA were injected either alone or combined with other cRNA into oocytes which had been explanted from the clawed frog *Xenopus laevis* [C. Methfessel et al., Pflügers Arch. 407, 577, (1986)]. The oocytes were incubated in OR-2 (92.5 mM NaCl, 2.5 mM KCl, 1 mM $Na_2HPO_4$, 5 mM HEPES, 1 mM $MgCl_2$, 1 mM $CaCl_2$, 0.5 g/l polyvinylpyrrolidone, pH 7.2 with the addition of 4 µg/ml Zinacef and 100 U/ml Penstrep) at 19° C. 24 hours after the injection, the oocytes were treated with collagenase (Sigma Type II) (1 mg/ml in OR-2 for 1 hour). Electrophysiological recordings were made 2–6 days after injection of the cRNA. A 2-electrode voltage clamp configuration was used for this with a TEC 01C amplifier (NPI Electronic, Tamm, Germany). During the electrophysiological measurements, the oocytes were perfused with normal frog Ringer solution (NRF: 115 mM NaCl, 2.5 mM KCl, 1.8 mM $CaCl_2$, 10 mM HEPES, pH 7.2).

EXAMPLE 5
Stable expression of the glutamate receptor subunits in HEK 293 cells The glutamate receptor cDNA molecules described in Examples 1 and 2 were cloned into the eukaryotic expression vectors pcDNA3 and pRc/CMV (from Invitrogen). These expression constructs were introduced singly or in combination into HEK 293 cells by electroporation by the following protocol: HEK 293 cells (ATCC) were cultivated in RPMI 1640 medium (Glutamax I from Gibco BRL) containing 10% FCS (Gibco BRL) under 5% $CO_2$. For the electroporation, $10^7$ cells were transfected in 0.8 ml of PBS with 20 µg of the expression construct using an electroporator (BTX, electro cell manipulator 600, 3 µF, 130 V, 72 ohm). The cells were subsequently incubated in culture medium for 24 h and then transferred into selection medium (RPMI medium with 600 µg/ml G418 sulfate, geneticin). Stable geneticin-resistant cell clones were isolated after 10–12 days by plating out and were expanded and analyzed by a membrane binding assay.

We claim:

1. An isolated polynucleotide coding for a variant of a glutamate receptor subunit, the sequence of said polynucleotide being selected from the group consisting of:

a) a polynucleotide comprising the nucleotide sequence shown in SEQ ID NO: 1 or SEQ ID NO: 3;

b) a polynucleotide sequence coding for a protein comprising the amino acid sequence shown in SEQ ID NO: 2 or SEQ ID NO: 4; and c) a polynucleotide comprising a nucleotide sequence fully complementary to the nucleotide sequence of a) or b).

2. A method of preparing a glutamate receptor subunit, comprising the steps of constructing a recombinant vector comprising the DNA sequence defined in claim 1 which codes for a glutamate receptor subunit;

transforming a compatible host with the recombinant vector such that the DNA sequence coding for the glutamate receptor subunit can be expressed by the host;

culturing the transformed host in a suitable growth medium to produce the glutamate receptor subunit; and recovering the glutamate receptor subunit from the medium.

3. The isolated polynucleotide of claim 1 wherein the polynucleotide comprises DNA.

4. The isolated polynucleotide of claim 1 wherein the polynucleotide comprises RNA.

5. A method for identifying functional ligands for glutamate receptors, which comprises tranfecting cells with one or more DNA sequences coding for a glutamate receptor as claimed in claim 1, and detecting the effect on the signal transduction pathway caused in these cells by binding of the ligands to the receptor by a reporter system.

* * * * *

SEQUENCE LISTING ( 1 ) GENERAL INFORMATION:

( i i i ) NUMBER OF SEQUENCES: 26

( 2 ) INFORMATION FOR SEQ ID NO: 1:

( i ) SEQUENCE CHARACTERISTICS:
        ( A ) LENGTH: 2946 base pairs
        ( B ) TYPE: nucleic acid
        ( C ) STRANDEDNESS: single
        ( D ) TOPOLOGY: linear ( i i ) MOLECULE TYPE: cDNA to mRNA ( v i ) ORIGINAL SOURCE:
        ( A ) ORGANISM: Homo sapiens
        ( B ) DEVELOPMENTAL STAGE: Adult
        ( C ) TISSUE TYPE: Brain ( i x ) FEATURE:
    ( A ) NAME/KEY: CDS
    ( B ) LOCATION: 144..2861

( x i ) SEQUENCE DESCRIPTION: SEQ ID NO: 1:

```
GAAAGGAAGG AAGCAAGCAA GCAAGGAAGG AACTGCAGGA GGAAAAGAAC AGGCAGAACA        60

GCGAAAAGAA TAAAGGGAAA GGGGGGGAAA CACCAAATCT ATGATTGGAC CTGGGCTTCT       120

TTTTCGCCAA TGCAAAAAGG AAT ATG CAG CAC ATT TTT GCC TTC TTC TGC           170
                         Met Gln His Ile Phe Ala Phe Phe Cys
                          1               5

ACC GGT TTC CTA GGC GCG GTA GTA GGT GCC AAT TTC CCC AAC AAT ATC         218
Thr Gly Phe Leu Gly Ala Val Val Gly Ala Asn Phe Pro Asn Asn Ile
 10              15                  20                  25

CAG ATC GGG GGA TTA TTT CCA AAC CAG CAG TCA CAG GAA CAT GCT GCT         266
Gln Ile Gly Gly Leu Phe Pro Asn Gln Gln Ser Gln Glu His Ala Ala
         30                  35                  40

TTT AGA TTT GCT TTG TCG CAA CTC ACA GAG CCC CCG AAG CTG CTC CCC         314
Phe Arg Phe Ala Leu Ser Gln Leu Thr Glu Pro Pro Lys Leu Leu Pro
             45                  50                  55

CAG ATT GAT ATT GTG AAC ATC AGC GAC AGC TTT GAG ATG ACC TAT AGA         362
Gln Ile Asp Ile Val Asn Ile Ser Asp Ser Phe Glu Met Thr Tyr Arg
                 60                  65                  70

TTC TGT TCC CAG TTC TCC AAA GGA GTC TAT GCC ATC TTT GGG TTT TAT         410
Phe Cys Ser Gln Phe Ser Lys Gly Val Tyr Ala Ile Phe Gly Phe Tyr
     75                  80                  85

GAA CGT AGG ACT GTC AAC ATG CTG ACC TCC TTT TGT GGG GCC CTC CAC         458
Glu Arg Arg Thr Val Asn Met Leu Thr Ser Phe Cys Gly Ala Leu His
 90              95                 100                 105

GTC TGC TTC ATT ACG CCG AGC TTT CCC GTT GAT ACA TCC AAT CAG TTT         506
Val Cys Phe Ile Thr Pro Ser Phe Pro Val Asp Thr Ser Asn Gln Phe
             110                 115                 120

GTC CTT CAG CTG CGC CCT GAA CTG CAG GAT GCC CTC ATC AGC ATC ATT         554
Val Leu Gln Leu Arg Pro Glu Leu Gln Asp Ala Leu Ile Ser Ile Ile
         125                 130                 135

GAC CAT TAC AAG TGG CAG AAA TTT GTC TAC ATT TAT GAT GCC GAC CGG         602
Asp His Tyr Lys Trp Gln Lys Phe Val Tyr Ile Tyr Asp Ala Asp Arg
             140                 145                 150

GGC TTA TCC GTC CTG CAG AAA GTC CTG GAT ACA GCT GCT GAG AAG AAC         650
Gly Leu Ser Val Leu Gln Lys Val Leu Asp Thr Ala Ala Glu Lys Asn
 155                 160                 165

TGG CAG GTG ACA GCA GTC AAC ATC TTG ACA ACC ACA GAG GAG GGA TAC         698
Trp Gln Val Thr Ala Val Asn Ile Leu Thr Thr Thr Glu Glu Gly Tyr
 170             175                 180                 185

CGG ATG CTC TTT CAG GAC CTG GAG AAG AAA AAG GAG CGG CTG GTG GTG         746
Arg Met Leu Phe Gln Asp Leu Glu Lys Lys Lys Glu Arg Leu Val Val
             190                 195                 200

GTG GAC TGT GAA TCA GAA CGC CTC AAT GCT ATC TTG GGC CAG ATT ATA         794
Val Asp Cys Glu Ser Glu Arg Leu Asn Ala Ile Leu Gly Gln Ile Ile
             205                 210                 215

AAG CTA GAG AAG AAT GGC ATC GGC TAC CAC TAC ATT CTT GCA AAT CTG         842
Lys Leu Glu Lys Asn Gly Ile Gly Tyr His Tyr Ile Leu Ala Asn Leu
         220                 225                 230

GGC TTC ATG GAC ATT GAC TTA AAC AAA TTC AAG GAG AGT GGC GCC AAT         890
Gly Phe Met Asp Ile Asp Leu Asn Lys Phe Lys Glu Ser Gly Ala Asn
 235                 240                 245

GTG ACA GGT TTC CAG CTG GTG AAC TAC ACA GAC ACT ATT CCG GCC AAG         938
Val Thr Gly Phe Gln Leu Val Asn Tyr Thr Asp Thr Ile Pro Ala Lys
 250                 255                 260                 265

ATC ATG CAG CAG TGG AAG AAT AGT GAT GCT CGA GAC CAC ACA CGG GTG         986
```

|     |     |     |     |     |     |     |     |     |     |     |     |     |     |     |     |     |
| --- | --- | --- | --- | --- | --- | --- | --- | --- | --- | --- | --- | --- | --- | --- | --- | --- |
| Ile | Met | Gln | Gln | Trp | Lys | Asn | Ser | Asp | Ala | Arg | Asp | His | Thr | Arg | Val |     |
|     |     |     | 270 |     |     |     |     | 275 |     |     |     |     | 280 |     |     |     |
| GAC | TGG | AAG | AGA | CCC | AAG | TAC | ACC | TCT | GCG | CTC | ACC | TAC | GAT | GGG | GTG | 1034 |
| Asp | Trp | Lys | Arg | Pro | Lys | Tyr | Thr | Ser | Ala | Leu | Thr | Tyr | Asp | Gly | Val |     |
|     |     |     | 285 |     |     |     |     | 290 |     |     |     |     | 295 |     |     |     |
| AAG | GTG | ATG | GCT | GAG | GCT | TTC | CAG | AGC | CTG | CGG | AGG | CAG | AGA | ATT | GAT | 1082 |
| Lys | Val | Met | Ala | Glu | Ala | Phe | Gln | Ser | Leu | Arg | Arg | Gln | Arg | Ile | Asp |     |
|     |     | 300 |     |     |     |     | 305 |     |     |     |     | 310 |     |     |     |     |
| ATA | TCT | CGC | CGG | GGG | AAT | GCT | GGG | GAT | TGT | CTG | GCT | AAC | CCA | GCT | GTT | 1130 |
| Ile | Ser | Arg | Arg | Gly | Asn | Ala | Gly | Asp | Cys | Leu | Ala | Asn | Pro | Ala | Val |     |
|     | 315 |     |     |     |     | 320 |     |     |     |     | 325 |     |     |     |     |     |
| CCC | TGG | GGC | CAA | GGG | ATC | GAC | ATC | CAG | AGA | GCT | CTG | CAG | CAG | GTG | CGA | 1178 |
| Pro | Trp | Gly | Gln | Gly | Ile | Asp | Ile | Gln | Arg | Ala | Leu | Gln | Gln | Val | Arg |     |
| 330 |     |     |     |     | 335 |     |     |     |     | 340 |     |     |     |     | 345 |     |
| TTT | GAA | GGT | TTA | ACA | GGA | AAC | GTG | CAG | TTT | AAT | GAG | AAA | GGA | CGC | CGG | 1226 |
| Phe | Glu | Gly | Leu | Thr | Gly | Asn | Val | Gln | Phe | Asn | Glu | Lys | Gly | Arg | Arg |     |
|     |     |     |     | 350 |     |     |     |     | 355 |     |     |     |     | 360 |     |     |
| ACC | AAC | TAC | ACG | CTC | CAC | GTG | ATT | GAA | ATG | AAA | CAT | GAC | AGC | ATC | CGA | 1274 |
| Thr | Asn | Tyr | Thr | Leu | His | Val | Ile | Glu | Met | Lys | His | Asp | Ser | Ile | Arg |     |
|     |     |     | 365 |     |     |     |     | 370 |     |     |     |     | 375 |     |     |     |
| AAG | ATT | GGT | TAC | TGG | AAT | GAA | GAT | GAT | AAG | TTT | GTC | CCT | GCA | GCC | ACC | 1322 |
| Lys | Ile | Gly | Tyr | Trp | Asn | Glu | Asp | Asp | Lys | Phe | Val | Pro | Ala | Ala | Thr |     |
|     |     | 380 |     |     |     |     | 385 |     |     |     |     | 390 |     |     |     |     |
| GAT | GCC | CAA | GCT | GGG | GGC | GAT | AAT | TCA | AGT | GTT | CAG | AAC | AGA | ACA | TAC | 1370 |
| Asp | Ala | Gln | Ala | Gly | Gly | Asp | Asn | Ser | Ser | Val | Gln | Asn | Arg | Thr | Tyr |     |
|     | 395 |     |     |     |     | 400 |     |     |     |     | 405 |     |     |     |     |     |
| ATC | GTC | ACA | ACA | ATC | CTA | GAA | GAT | CCT | TAT | GTG | ATG | CTC | AAG | AAG | AAC | 1418 |
| Ile | Val | Thr | Thr | Ile | Leu | Glu | Asp | Pro | Tyr | Val | Met | Leu | Lys | Lys | Asn |     |
| 410 |     |     |     |     | 415 |     |     |     |     | 420 |     |     |     |     | 425 |     |
| GCC | AAT | CAG | TTT | GAG | GGC | AAT | GAC | CGT | TAC | GAG | GGC | TAC | TGT | GTA | GAG | 1466 |
| Ala | Asn | Gln | Phe | Glu | Gly | Asn | Asp | Arg | Tyr | Glu | Gly | Tyr | Cys | Val | Glu |     |
|     |     |     |     | 430 |     |     |     |     | 435 |     |     |     |     | 440 |     |     |
| CTG | GCG | GCA | GAG | ATT | GCC | AAG | CAC | GTG | GGC | TAC | TCC | TAC | CGT | CTG | GAG | 1514 |
| Leu | Ala | Ala | Glu | Ile | Ala | Lys | His | Val | Gly | Tyr | Ser | Tyr | Arg | Leu | Glu |     |
|     |     |     | 445 |     |     |     |     | 450 |     |     |     |     | 455 |     |     |     |
| ATT | GTC | AGT | GAT | GGA | AAA | TAC | GGA | GCC | CGA | GAC | CCT | GAC | ACG | AAG | GCC | 1562 |
| Ile | Val | Ser | Asp | Gly | Lys | Tyr | Gly | Ala | Arg | Asp | Pro | Asp | Thr | Lys | Ala |     |
|     |     | 460 |     |     |     |     | 465 |     |     |     |     | 470 |     |     |     |     |
| TGG | AAT | GGC | ATG | GTG | GGA | GAG | CTG | GTC | TAT | GGA | AGA | GCA | GAT | GTG | GCT | 1610 |
| Trp | Asn | Gly | Met | Val | Gly | Glu | Leu | Val | Tyr | Gly | Arg | Ala | Asp | Val | Ala |     |
|     | 475 |     |     |     |     | 480 |     |     |     |     | 485 |     |     |     |     |     |
| GTG | GCT | CCC | TTA | ACT | ATC | ACT | TTG | GTC | CGG | GAA | GAA | GTT | ATA | GAT | TTC | 1658 |
| Val | Ala | Pro | Leu | Thr | Ile | Thr | Leu | Val | Arg | Glu | Glu | Val | Ile | Asp | Phe |     |
| 490 |     |     |     |     | 495 |     |     |     |     | 500 |     |     |     |     | 505 |     |
| TCC | AAA | CCA | TTT | ATG | AGT | TTG | GGG | ATC | TCC | ATC | ATG | ATT | AAA | AAA | CCA | 1706 |
| Ser | Lys | Pro | Phe | Met | Ser | Leu | Gly | Ile | Ser | Ile | Met | Ile | Lys | Lys | Pro |     |
|     |     |     |     | 510 |     |     |     |     | 515 |     |     |     |     | 520 |     |     |
| CAG | AAA | TCC | AAG | CCG | GGT | GTC | TTC | TCC | TTC | CTT | GAT | CCT | TTG | GCT | TAT | 1754 |
| Gln | Lys | Ser | Lys | Pro | Gly | Val | Phe | Ser | Phe | Leu | Asp | Pro | Leu | Ala | Tyr |     |
|     |     |     | 525 |     |     |     |     | 530 |     |     |     |     | 535 |     |     |     |
| GAG | ATT | TGG | ATG | TGC | ATT | GTT | TTT | GCC | TAC | ATT | GGA | GTG | AGT | GTT | GTC | 1802 |
| Glu | Ile | Trp | Met | Cys | Ile | Val | Phe | Ala | Tyr | Ile | Gly | Val | Ser | Val | Val |     |
|     |     | 540 |     |     |     |     | 545 |     |     |     |     | 550 |     |     |     |     |
| CTC | TTC | CTG | GTC | AGC | CGC | TTC | AGT | CCC | TAT | GAA | TGG | CAC | AGT | GAA | GAG | 1850 |
| Leu | Phe | Leu | Val | Ser | Arg | Phe | Ser | Pro | Tyr | Glu | Trp | His | Ser | Glu | Glu |     |
|     | 555 |     |     |     |     | 560 |     |     |     |     | 565 |     |     |     |     |     |
| TTT | GAG | GAA | GGA | CGG | GAC | CAG | ACA | ACC | AGT | GAC | CAG | TCC | AAT | GAG | TTT | 1898 |
| Phe | Glu | Glu | Gly | Arg | Asp | Gln | Thr | Thr | Ser | Asp | Gln | Ser | Asn | Glu | Phe |     |
| 570 |     |     |     |     | 575 |     |     |     |     | 580 |     |     |     |     | 585 |     |
| GGG | ATA | TTC | AAC | AGT | TTG | TGG | TTC | TCC | CTG | GGA | GCC | TTC | ATG | CAG | CAA | 1946 |

-continued

| | | | | | | | | | | | | | | | |
|---|---|---|---|---|---|---|---|---|---|---|---|---|---|---|---|
| Gly | Ile | Phe | Asn | Ser | Leu | Trp | Phe | Ser | Leu | Gly | Ala | Phe | Met | Gln | Gln |
| | | | | 590 | | | | 595 | | | | | | 600 | |

| GGA | TGT | GAC | ATT | TCT | CCC | AGG | TCC | CTG | TCT | GGT | CGC | ATC | GTT | GGT | GGC | 1994 |
|---|---|---|---|---|---|---|---|---|---|---|---|---|---|---|---|---|
| Gly | Cys | Asp | Ile | Ser | Pro | Arg | Ser | Leu | Ser | Gly | Arg | Ile | Val | Gly | Gly | |
| | | | 605 | | | | | 610 | | | | | 615 | | | |

| GTC | TGG | TGG | TTC | TTC | ACC | TTA | ATC | ATC | ATC | TCC | TCA | TAT | ACA | GCC | AAT | 2042 |
|---|---|---|---|---|---|---|---|---|---|---|---|---|---|---|---|---|
| Val | Trp | Trp | Phe | Phe | Thr | Leu | Ile | Ile | Ile | Ser | Ser | Tyr | Thr | Ala | Asn | |
| | | 620 | | | | | 625 | | | | | 630 | | | | |

| CTG | GCC | GCC | TTC | CTG | ACC | GTG | GAG | AGG | ATG | GTG | TCT | CCC | ATT | GAG | AGT | 2090 |
|---|---|---|---|---|---|---|---|---|---|---|---|---|---|---|---|---|
| Leu | Ala | Ala | Phe | Leu | Thr | Val | Glu | Arg | Met | Val | Ser | Pro | Ile | Glu | Ser | |
| 635 | | | | | 640 | | | | | 645 | | | | | | |

| GCA | GAG | GAC | CTA | GCG | AAG | CAG | ACA | GAA | ATT | GCC | TAC | GGG | ACG | CTG | GAA | 2138 |
|---|---|---|---|---|---|---|---|---|---|---|---|---|---|---|---|---|
| Ala | Glu | Asp | Leu | Ala | Lys | Gln | Thr | Glu | Ile | Ala | Tyr | Gly | Thr | Leu | Glu | |
| 650 | | | | 655 | | | | | 660 | | | | | 665 | | |

| GCA | GGA | TCT | ACT | AAG | GAG | TTC | TTC | AGG | AGG | TCT | AAA | ATT | GCT | GTG | TTT | 2186 |
|---|---|---|---|---|---|---|---|---|---|---|---|---|---|---|---|---|
| Ala | Gly | Ser | Thr | Lys | Glu | Phe | Phe | Arg | Arg | Ser | Lys | Ile | Ala | Val | Phe | |
| | | | | 670 | | | | | 675 | | | | | 680 | | |

| GAG | AAG | ATG | TGG | ACA | TAC | ATG | AAG | TCA | GCA | GAG | CCA | TCA | GTT | TTT | GTG | 2234 |
|---|---|---|---|---|---|---|---|---|---|---|---|---|---|---|---|---|
| Glu | Lys | Met | Trp | Thr | Tyr | Met | Lys | Ser | Ala | Glu | Pro | Ser | Val | Phe | Val | |
| | | | 685 | | | | | 690 | | | | | 695 | | | |

| CGG | ACC | ACA | GAG | GAG | GGG | ATG | ATT | CGA | GTG | AGG | AAA | TCC | AAA | GGC | AAA | 2282 |
|---|---|---|---|---|---|---|---|---|---|---|---|---|---|---|---|---|
| Arg | Thr | Thr | Glu | Glu | Gly | Met | Ile | Arg | Val | Arg | Lys | Ser | Lys | Gly | Lys | |
| | | 700 | | | | | 705 | | | | | 710 | | | | |

| TAT | GCC | TAC | CTC | CTG | GAG | TCC | ACC | ATG | AAT | GAG | TAC | ATT | GAG | CAG | CGG | 2330 |
|---|---|---|---|---|---|---|---|---|---|---|---|---|---|---|---|---|
| Tyr | Ala | Tyr | Leu | Leu | Glu | Ser | Thr | Met | Asn | Glu | Tyr | Ile | Glu | Gln | Arg | |
| 715 | | | | | 720 | | | | | 725 | | | | | | |

| AAA | CCC | TGT | GAC | ACC | ATG | AAG | GTG | GGA | GGT | AAC | TTG | GAT | TCC | AAA | GGC | 2378 |
|---|---|---|---|---|---|---|---|---|---|---|---|---|---|---|---|---|
| Lys | Pro | Cys | Asp | Thr | Met | Lys | Val | Gly | Gly | Asn | Leu | Asp | Ser | Lys | Gly | |
| 730 | | | | 735 | | | | | 740 | | | | | 745 | | |

| TAT | GGC | ATT | GCA | ACA | CCC | AAG | GGG | TCT | GCC | CTG | GGA | GGT | CCC | GTA | AAC | 2426 |
|---|---|---|---|---|---|---|---|---|---|---|---|---|---|---|---|---|
| Tyr | Gly | Ile | Ala | Thr | Pro | Lys | Gly | Ser | Ala | Leu | Gly | Gly | Pro | Val | Asn | |
| | | | 750 | | | | | 755 | | | | | 760 | | | |

| CTA | GCG | GTT | TTG | AAA | CTC | AGT | GAG | CAA | GGC | GTC | TTA | GAC | AAG | CTG | AAA | 2474 |
|---|---|---|---|---|---|---|---|---|---|---|---|---|---|---|---|---|
| Leu | Ala | Val | Leu | Lys | Leu | Ser | Glu | Gln | Gly | Val | Leu | Asp | Lys | Leu | Lys | |
| | | | 765 | | | | | 770 | | | | | 775 | | | |

| AGC | AAA | TGG | TGG | TAC | GAT | AAA | GGG | GAA | TGT | GGA | AGC | AAG | GAC | TCC | GGA | 2522 |
|---|---|---|---|---|---|---|---|---|---|---|---|---|---|---|---|---|
| Ser | Lys | Trp | Trp | Tyr | Asp | Lys | Gly | Glu | Cys | Gly | Ser | Lys | Asp | Ser | Gly | |
| | | 780 | | | | | 785 | | | | | 790 | | | | |

| AGT | AAG | GAC | AAG | ACA | AGC | GCT | CTG | AGC | CTC | AGC | AAT | GTG | GCA | GGC | GTG | 2570 |
|---|---|---|---|---|---|---|---|---|---|---|---|---|---|---|---|---|
| Ser | Lys | Asp | Lys | Thr | Ser | Ala | Leu | Ser | Leu | Ser | Asn | Val | Ala | Gly | Val | |
| 795 | | | | | 800 | | | | | 805 | | | | | | |

| TTC | TAC | ATC | CTG | ATC | GGA | GGA | CTT | GGA | CTA | GCC | ATG | CTG | GTT | GCC | TTA | 2618 |
|---|---|---|---|---|---|---|---|---|---|---|---|---|---|---|---|---|
| Phe | Tyr | Ile | Leu | Ile | Gly | Gly | Leu | Gly | Leu | Ala | Met | Leu | Val | Ala | Leu | |
| 810 | | | | | 815 | | | | | 820 | | | | | 825 | |

| ATC | GAG | TTC | TGC | TAC | AAA | TCC | CGT | AGT | GAA | TCC | AAG | CGG | ATG | AAG | GGT | 2666 |
|---|---|---|---|---|---|---|---|---|---|---|---|---|---|---|---|---|
| Ile | Glu | Phe | Cys | Tyr | Lys | Ser | Arg | Ser | Glu | Ser | Lys | Arg | Met | Lys | Gly | |
| | | | 830 | | | | | 835 | | | | | 840 | | | |

| TTT | TGT | TTG | ATC | CCA | CAG | CAA | TCC | ATC | AAC | GAA | GCC | ATA | CGG | ACA | TCG | 2714 |
|---|---|---|---|---|---|---|---|---|---|---|---|---|---|---|---|---|
| Phe | Cys | Leu | Ile | Pro | Gln | Gln | Ser | Ile | Asn | Glu | Ala | Ile | Arg | Thr | Ser | |
| | | | 845 | | | | | 850 | | | | | 855 | | | |

| ACC | CTC | CCC | CGC | AAC | AGC | GGG | GCA | GGA | GCC | AGC | AGC | GGC | GGC | AGT | GGA | 2762 |
|---|---|---|---|---|---|---|---|---|---|---|---|---|---|---|---|---|
| Thr | Leu | Pro | Arg | Asn | Ser | Gly | Ala | Gly | Ala | Ser | Ser | Gly | Gly | Ser | Gly | |
| | | 860 | | | | | 865 | | | | | 870 | | | | |

| GAG | AAT | GGT | CGG | GTG | GTC | AGC | CAT | GAC | TTC | CCC | AAG | TCC | ATG | CAA | TCG | 2810 |
|---|---|---|---|---|---|---|---|---|---|---|---|---|---|---|---|---|
| Glu | Asn | Gly | Arg | Val | Val | Ser | His | Asp | Phe | Pro | Lys | Ser | Met | Gln | Ser | |
| 875 | | | | | 880 | | | | | 885 | | | | | | |

| ATT | CCT | TGC | ATG | AGC | CAC | AGT | TCA | GGG | ATG | CCC | TTG | GGA | GCC | ACG | GGA | 2858 |
|---|---|---|---|---|---|---|---|---|---|---|---|---|---|---|---|---|
| Ile | Pro | Cys | Met | Ser | His | Ser | Ser | Gly | Met | Pro | Leu | Gly | Ala | Thr | Gly | |
| 890 | | | | 895 | | | | | 900 | | | | | 905 | | |

| TTG | TAACTGGAGC | AGATGGAGAC | CCCTTGGGGA | GCAGGCTCGG | CTCCCCAGCC | 2911 |
|---|---|---|---|---|---|---|
| Leu | | | | | | |

Leu

CCATCCCAAA CCCTTCAGTG CCAAAAACAA CAAAA    2946

(2) INFORMATION FOR SEQ ID NO:2:

(i) SEQUENCE CHARACTERISTICS:
        (A) LENGTH: 906 amino acids
        (B) TYPE: amino acid
        (D) TOPOLOGY: linear (ii) MOLECULE TYPE: protein (xi) SEQUENCE DESCRIPTION: SEQ ID NO: 2:

```
Met Gln His Ile Phe Ala Phe Phe Cys Thr Gly Phe Leu Gly Ala Val
 1               5                  10                  15

Val Gly Ala Asn Phe Pro Asn Asn Ile Gln Ile Gly Gly Leu Phe Pro
                20                  25                  30

Asn Gln Gln Ser Gln Glu His Ala Ala Phe Arg Phe Ala Leu Ser Gln
            35                  40                  45

Leu Thr Glu Pro Pro Lys Leu Leu Pro Gln Ile Asp Ile Val Asn Ile
        50                  55                  60

Ser Asp Ser Phe Glu Met Thr Tyr Arg Phe Cys Ser Gln Phe Ser Lys
65                  70                  75                  80

Gly Val Tyr Ala Ile Phe Gly Phe Tyr Glu Arg Arg Thr Val Asn Met
                85                  90                  95

Leu Thr Ser Phe Cys Gly Ala Leu His Val Cys Phe Ile Thr Pro Ser
                100                 105                 110

Phe Pro Val Asp Thr Ser Asn Gln Phe Val Leu Gln Leu Arg Pro Glu
            115                 120                 125

Leu Gln Asp Ala Leu Ile Ser Ile Ile Asp His Tyr Lys Trp Gln Lys
130                 135                 140

Phe Val Tyr Ile Tyr Asp Ala Asp Arg Gly Leu Ser Val Leu Gln Lys
145                 150                 155                 160

Val Leu Asp Thr Ala Ala Glu Lys Asn Trp Gln Val Thr Ala Val Asn
                165                 170                 175

Ile Leu Thr Thr Thr Glu Glu Gly Tyr Arg Met Leu Phe Gln Asp Leu
                180                 185                 190

Glu Lys Lys Lys Glu Arg Leu Val Val Val Asp Cys Glu Ser Glu Arg
            195                 200                 205

Leu Asn Ala Ile Leu Gly Gln Ile Ile Lys Leu Glu Lys Asn Gly Ile
210                 215                 220

Gly Tyr His Tyr Ile Leu Ala Asn Leu Gly Phe Met Asp Ile Asp Leu
225                 230                 235                 240

Asn Lys Phe Lys Glu Ser Gly Ala Asn Val Thr Gly Phe Gln Leu Val
                245                 250                 255

Asn Tyr Thr Asp Thr Ile Pro Ala Lys Ile Met Gln Gln Trp Lys Asn
                260                 265                 270

Ser Asp Ala Arg Asp His Thr Arg Val Asp Trp Lys Arg Pro Lys Tyr
            275                 280                 285

Thr Ser Ala Leu Thr Tyr Asp Gly Val Lys Val Met Ala Glu Ala Phe
        290                 295                 300

Gln Ser Leu Arg Arg Gln Arg Ile Asp Ile Ser Arg Arg Gly Asn Ala
305                 310                 315                 320

Gly Asp Cys Leu Ala Asn Pro Ala Val Pro Trp Gly Gln Gly Ile Asp
                325                 330                 335

Ile Gln Arg Ala Leu Gln Gln Val Arg Phe Glu Gly Leu Thr Gly Asn
```

-continued

```
                    340                          345                          350
Val  Gln  Phe  Asn  Glu  Lys  Gly  Arg  Arg  Thr  Asn  Tyr  Thr  Leu  His  Val
          355                      360                     365

Ile  Glu  Met  Lys  His  Asp  Ser  Ile  Arg  Lys  Ile  Gly  Tyr  Trp  Asn  Glu
     370                      375                     380

Asp  Asp  Lys  Phe  Val  Pro  Ala  Ala  Thr  Asp  Ala  Gln  Ala  Gly  Gly  Asp
385                      390                     395                          400

Asn  Ser  Ser  Val  Gln  Asn  Arg  Thr  Tyr  Ile  Val  Thr  Thr  Ile  Leu  Glu
                    405                     410                          415

Asp  Pro  Tyr  Val  Met  Leu  Lys  Lys  Asn  Ala  Asn  Gln  Phe  Glu  Gly  Asn
               420                     425                     430

Asp  Arg  Tyr  Glu  Gly  Tyr  Cys  Val  Glu  Leu  Ala  Ala  Glu  Ile  Ala  Lys
          435                     440                     445

His  Val  Gly  Tyr  Ser  Tyr  Arg  Leu  Glu  Ile  Val  Ser  Asp  Gly  Lys  Tyr
     450                     455                     460

Gly  Ala  Arg  Asp  Pro  Asp  Thr  Lys  Ala  Trp  Asn  Gly  Met  Val  Gly  Glu
465                     470                     475                          480

Leu  Val  Tyr  Gly  Arg  Ala  Asp  Val  Ala  Val  Ala  Pro  Leu  Thr  Ile  Thr
               485                     490                          495

Leu  Val  Arg  Glu  Glu  Val  Ile  Asp  Phe  Ser  Lys  Pro  Phe  Met  Ser  Leu
               500                     505                     510

Gly  Ile  Ser  Ile  Met  Ile  Lys  Lys  Pro  Gln  Lys  Ser  Lys  Pro  Gly  Val
          515                     520                     525

Phe  Ser  Phe  Leu  Asp  Pro  Leu  Ala  Tyr  Glu  Ile  Trp  Met  Cys  Ile  Val
     530                     535                     540

Phe  Ala  Tyr  Ile  Gly  Val  Ser  Val  Val  Leu  Phe  Leu  Val  Ser  Arg  Phe
545                     550                     555                          560

Ser  Pro  Tyr  Glu  Trp  His  Ser  Glu  Glu  Phe  Glu  Glu  Gly  Arg  Asp  Gln
                    565                     570                     575

Thr  Thr  Ser  Asp  Gln  Ser  Asn  Glu  Phe  Gly  Ile  Phe  Asn  Ser  Leu  Trp
               580                     585                     590

Phe  Ser  Leu  Gly  Ala  Phe  Met  Gln  Gln  Gly  Cys  Asp  Ile  Ser  Pro  Arg
     595                     600                     605

Ser  Leu  Ser  Gly  Arg  Ile  Val  Gly  Gly  Val  Trp  Trp  Phe  Phe  Thr  Leu
     610                     615                     620

Ile  Ile  Ile  Ser  Ser  Tyr  Thr  Ala  Asn  Leu  Ala  Ala  Phe  Leu  Thr  Val
625                     630                     635                          640

Glu  Arg  Met  Val  Ser  Pro  Ile  Glu  Ser  Ala  Glu  Asp  Leu  Ala  Lys  Gln
               645                     650                     655

Thr  Glu  Ile  Ala  Tyr  Gly  Thr  Leu  Glu  Ala  Gly  Ser  Thr  Lys  Glu  Phe
               660                     665                     670

Phe  Arg  Arg  Ser  Lys  Ile  Ala  Val  Phe  Glu  Lys  Met  Trp  Thr  Tyr  Met
          675                     680                     685

Lys  Ser  Ala  Glu  Pro  Ser  Val  Phe  Val  Arg  Thr  Thr  Glu  Glu  Gly  Met
     690                     695                     700

Ile  Arg  Val  Arg  Lys  Ser  Lys  Gly  Lys  Tyr  Ala  Tyr  Leu  Leu  Glu  Ser
705                     710                     715                          720

Thr  Met  Asn  Glu  Tyr  Ile  Glu  Gln  Arg  Lys  Pro  Cys  Asp  Thr  Met  Lys
               725                     730                     735

Val  Gly  Gly  Asn  Leu  Asp  Ser  Lys  Gly  Tyr  Gly  Ile  Ala  Thr  Pro  Lys
               740                     745                     750

Gly  Ser  Ala  Leu  Gly  Gly  Pro  Val  Asn  Leu  Ala  Val  Leu  Lys  Leu  Ser
          755                     760                     765
```

|     |     |     |     |     |     |     |     |     |     |     |     |     |     |     |
| --- | --- | --- | --- | --- | --- | --- | --- | --- | --- | --- | --- | --- | --- | --- |
| Glu | Gln | Gly | Val | Leu | Asp | Lys | Leu | Lys | Ser | Lys | Trp | Trp | Tyr | Asp | Lys |
|     | 770 |     |     |     |     | 775 |     |     |     |     | 780 |     |     |     |     |
| Gly | Glu | Cys | Gly | Ser | Lys | Asp | Ser | Gly | Ser | Lys | Asp | Lys | Thr | Ser | Ala |
| 785 |     |     |     |     | 790 |     |     |     |     | 795 |     |     |     |     | 800 |
| Leu | Ser | Leu | Ser | Asn | Val | Ala | Gly | Val | Phe | Tyr | Ile | Leu | Ile | Gly | Gly |
|     |     |     |     | 805 |     |     |     |     | 810 |     |     |     |     | 815 |     |
| Leu | Gly | Leu | Ala | Met | Leu | Val | Ala | Leu | Ile | Glu | Phe | Cys | Tyr | Lys | Ser |
|     |     |     |     | 820 |     |     |     |     | 825 |     |     |     |     | 830 |     |
| Arg | Ser | Glu | Ser | Lys | Arg | Met | Lys | Gly | Phe | Cys | Leu | Ile | Pro | Gln | Gln |
|     |     |     | 835 |     |     |     | 840 |     |     |     |     | 845 |     |     |     |
| Ser | Ile | Asn | Glu | Ala | Ile | Arg | Thr | Ser | Thr | Leu | Pro | Arg | Asn | Ser | Gly |
|     | 850 |     |     |     |     | 855 |     |     |     |     | 860 |     |     |     |     |
| Ala | Gly | Ala | Ser | Ser | Gly | Gly | Ser | Gly | Glu | Asn | Gly | Arg | Val | Val | Ser |
| 865 |     |     |     |     | 870 |     |     |     |     | 875 |     |     |     |     | 880 |
| His | Asp | Phe | Pro | Lys | Ser | Met | Gln | Ser | Ile | Pro | Cys | Met | Ser | His | Ser |
|     |     |     |     | 885 |     |     |     |     | 890 |     |     |     |     | 895 |     |
| Ser | Gly | Met | Pro | Leu | Gly | Ala | Thr | Gly | Leu |     |     |     |     |     |     |
|     |     |     | 900 |     |     |     |     | 905 |     |     |     |     |     |     |     |

( 2 ) INFORMATION FOR SEQ ID NO: 3:

( i ) SEQUENCE CHARACTERISTICS:
        ( A ) LENGTH: 2946 base pairs
        ( B ) TYPE: nucleic acid
        ( C ) STRANDEDNESS: single
        ( D ) TOPOLOGY: linear ( i i ) MOLECULE TYPE: cDNA to mRNA ( v i ) ORIGINAL SOURCE:
        ( A ) ORGANISM: Homo sapiens
        ( B ) DEVELOPMENTAL STAGE: Adult
        ( C ) TISSUE TYPE: Brain ( i x ) FEATURE:
        ( A ) NAME/KEY: CDS
        ( B ) LOCATION: 144..2861

( x i ) SEQUENCE DESCRIPTION: SEQ ID NO: 3:

|     |     |     |     |     |     |     |     |     |     |     |     |     |     |     |     |     |
| --- | --- | --- | --- | --- | --- | --- | --- | --- | --- | --- | --- | --- | --- | --- | --- | --- |
| GAAAGGAAGG | AAGCAAGCAA | GCAAGGAAGG | AACTGCAGGA | GGAAAAGAAC | AGGCAGAACA |     |     |     |     |     |     |     |     |     |     | 60 |
| GCGAAAAGAA | TAAAGGGAAA | GGGGGGGAAA | CACCAAATCT | ATGATTGGAC | CTGGGCTTCT |     |     |     |     |     |     |     |     |     |     | 120 |
| TTTTCGCCAA | TGCAAAAAGG | AAT | ATG | CAG | CAC | ATT | TTT | GCC | TTC | TTC | TGC |     |     |     |     | 170 |
|     |     |     | Met | Gln | His | Ile | Phe | Ala | Phe | Phe | Cys |     |     |     |     |     |
|     |     |     | 1   |     |     |     | 5   |     |     |     |     |     |     |     |     |     |
| ACC | GGT | TTC | CTA | GGC | GCG | GTA | GTA | GGT | GCC | AAT | TTC | CCC | AAC | AAT | ATC | 218 |
| Thr | Gly | Phe | Leu | Gly | Ala | Val | Val | Gly | Ala | Asn | Phe | Pro | Asn | Asn | Ile |     |
| 10  |     |     |     | 15  |     |     |     |     | 20  |     |     |     |     | 25  |     |     |
| CAG | ATC | GGG | GGA | TTA | TTT | CCA | AAC | CAG | CAG | TCA | CAG | GAA | CAT | GCT | GCT | 266 |
| Gln | Ile | Gly | Gly | Leu | Phe | Pro | Asn | Gln | Gln | Ser | Gln | Glu | His | Ala | Ala |     |
|     |     |     |     | 30  |     |     |     |     | 35  |     |     |     |     | 40  |     |     |
| TTT | AGA | TTT | GCT | TTG | TCG | CAA | CTC | ACA | GAG | CCC | CCG | AAG | CTG | CTC | CCC | 314 |
| Phe | Arg | Phe | Ala | Leu | Ser | Gln | Leu | Thr | Glu | Pro | Pro | Lys | Leu | Leu | Pro |     |
|     |     |     |     | 45  |     |     |     |     | 50  |     |     |     |     | 55  |     |     |
| CAG | ATT | GAT | ATT | GTG | AAC | ATC | AGC | GAC | AGC | TTT | GAG | ATG | ACC | TAT | AGA | 362 |
| Gln | Ile | Asp | Ile | Val | Asn | Ile | Ser | Asp | Ser | Phe | Glu | Met | Thr | Tyr | Arg |     |
|     |     |     | 60  |     |     |     |     | 65  |     |     |     |     | 70  |     |     |     |
| TTC | TGT | TCC | CAG | TTC | TCC | AAA | GGA | GTC | TAT | GCC | ATC | TTT | GGG | TTT | TAT | 410 |
| Phe | Cys | Ser | Gln | Phe | Ser | Lys | Gly | Val | Tyr | Ala | Ile | Phe | Gly | Phe | Tyr |     |
|     | 75  |     |     |     |     | 80  |     |     |     |     | 85  |     |     |     |     |     |
| GAA | CGT | AGG | ACT | GTC | AAC | ATG | CTG | ACC | TCC | TTT | TGT | GGG | GCC | CTC | CAC | 458 |
| Glu | Arg | Arg | Thr | Val | Asn | Met | Leu | Thr | Ser | Phe | Cys | Gly | Ala | Leu | His |     |
| 90  |     |     |     |     | 95  |     |     |     |     | 100 |     |     |     |     | 105 |     |

| | | | | | | | | | | | | | | | | |
|---|---|---|---|---|---|---|---|---|---|---|---|---|---|---|---|---|
| GTC | TGC | TTC | ATT | ACG | CCG | AGC | TTT | CCC | GTT | GAT | ACA | TCC | AAT | CAG | TTT | 506 |
| Val | Cys | Phe | Ile | Thr | Pro | Ser | Phe | Pro | Val | Asp | Thr | Ser | Asn | Gln | Phe | |
| | | | 110 | | | | | | 115 | | | | | 120 | | |
| GTC | CTT | CAG | CTG | CGC | CCT | GAA | CTG | CAG | GAT | GCC | CTC | ATC | AGC | ATC | ATT | 554 |
| Val | Leu | Gln | Leu | Arg | Pro | Glu | Leu | Gln | Asp | Ala | Leu | Ile | Ser | Ile | Ile | |
| | | 125 | | | | | 130 | | | | | 135 | | | | |
| GAC | CAT | TAC | AAG | TGG | CAG | AAA | TTT | GTC | TAC | ATT | TAT | GAT | GCC | GAC | CGG | 602 |
| Asp | His | Tyr | Lys | Trp | Gln | Lys | Phe | Val | Tyr | Ile | Tyr | Asp | Ala | Asp | Arg | |
| | | | 140 | | | | | 145 | | | | | 150 | | | |
| GGC | TTA | TCC | GTC | CTG | CAG | AAA | GTC | CTG | GAT | ACA | GCT | GCT | GAG | AAG | AAC | 650 |
| Gly | Leu | Ser | Val | Leu | Gln | Lys | Val | Leu | Asp | Thr | Ala | Ala | Glu | Lys | Asn | |
| | 155 | | | | | 160 | | | | | 165 | | | | | |
| TGG | CAG | GTG | ACA | GCA | GTC | AAC | ATC | TTG | ACA | ACC | ACA | GAG | GAG | GGA | TAC | 698 |
| Trp | Gln | Val | Thr | Ala | Val | Asn | Ile | Leu | Thr | Thr | Thr | Glu | Glu | Gly | Tyr | |
| 170 | | | | | 175 | | | | | 180 | | | | | 185 | |
| CGG | ATG | CTC | TTT | CAG | GAC | CTG | GAG | AAG | AAA | AAG | GAG | CGG | CTG | GTG | GTG | 746 |
| Arg | Met | Leu | Phe | Gln | Asp | Leu | Glu | Lys | Lys | Lys | Glu | Arg | Leu | Val | Val | |
| | | | | 190 | | | | | 195 | | | | | 200 | | |
| GTG | GAC | TGT | GAA | TCA | GAA | CGC | CTC | AAT | GCT | ATC | TTG | GGC | CAG | ATT | ATA | 794 |
| Val | Asp | Cys | Glu | Ser | Glu | Arg | Leu | Asn | Ala | Ile | Leu | Gly | Gln | Ile | Ile | |
| | | | 205 | | | | | 210 | | | | | 215 | | | |
| AAG | CTA | GAG | AAG | AAT | GGC | ATC | GGC | TAC | CAC | TAC | ATT | CTT | GCA | AAT | CTG | 842 |
| Lys | Leu | Glu | Lys | Asn | Gly | Ile | Gly | Tyr | His | Tyr | Ile | Leu | Ala | Asn | Leu | |
| | | 220 | | | | | 225 | | | | | 230 | | | | |
| GGC | TTC | ATG | GAC | ATT | GAC | TTA | AAC | AAA | TTC | AAG | GAG | AGT | GGC | GCC | AAT | 890 |
| Gly | Phe | Met | Asp | Ile | Asp | Leu | Asn | Lys | Phe | Lys | Glu | Ser | Gly | Ala | Asn | |
| | 235 | | | | | 240 | | | | | 245 | | | | | |
| GTG | ACA | GGT | TTC | CAG | CTG | GTG | AAC | TAC | ACA | GAC | ACT | ATT | CCG | GCC | AAG | 938 |
| Val | Thr | Gly | Phe | Gln | Leu | Val | Asn | Tyr | Thr | Asp | Thr | Ile | Pro | Ala | Lys | |
| 250 | | | | | 255 | | | | | 260 | | | | | 265 | |
| ATC | ATG | CAG | CAG | TGG | AAG | AAT | AGT | GAT | GCT | CGA | GAC | CAC | ACA | CGG | GTG | 986 |
| Ile | Met | Gln | Gln | Trp | Lys | Asn | Ser | Asp | Ala | Arg | Asp | His | Thr | Arg | Val | |
| | | | | 270 | | | | | 275 | | | | | 280 | | |
| GAC | TGG | AAG | AGA | CCC | AAG | TAC | ACC | TCT | GCG | CTC | ACC | TAC | GAT | GGG | GTG | 1034 |
| Asp | Trp | Lys | Arg | Pro | Lys | Tyr | Thr | Ser | Ala | Leu | Thr | Tyr | Asp | Gly | Val | |
| | | | 285 | | | | | 290 | | | | | 295 | | | |
| AAG | GTG | ATG | GCT | GAG | GCT | TTC | CAG | AGC | CTG | CGG | AGG | CAG | AGA | ATT | GAT | 1082 |
| Lys | Val | Met | Ala | Glu | Ala | Phe | Gln | Ser | Leu | Arg | Arg | Gln | Arg | Ile | Asp | |
| | | 300 | | | | | 305 | | | | | 310 | | | | |
| ATA | TCT | CGC | CGG | GGG | AAT | GCT | GGG | GAT | TGT | CTG | GCT | AAC | CCA | GCT | GTT | 1130 |
| Ile | Ser | Arg | Arg | Gly | Asn | Ala | Gly | Asp | Cys | Leu | Ala | Asn | Pro | Ala | Val | |
| | 315 | | | | | 320 | | | | | 325 | | | | | |
| CCC | TGG | GGC | CAA | GGG | ATC | GAC | ATC | CAG | AGA | GCT | CTG | CAG | CAG | GTG | CGA | 1178 |
| Pro | Trp | Gly | Gln | Gly | Ile | Asp | Ile | Gln | Arg | Ala | Leu | Gln | Gln | Val | Arg | |
| 330 | | | | | 335 | | | | | 340 | | | | | 345 | |
| TTT | GAA | GGT | TTA | ACA | GGA | AAC | GTG | CAG | TTT | AAT | GAG | AAA | GGA | CGC | CGG | 1226 |
| Phe | Glu | Gly | Leu | Thr | Gly | Asn | Val | Gln | Phe | Asn | Glu | Lys | Gly | Arg | Arg | |
| | | | | 350 | | | | | 355 | | | | | 360 | | |
| ACC | AAC | TAC | ACG | CTC | CAC | GTG | ATT | GAA | ATG | AAA | CAT | GAC | AGC | ATC | CGA | 1274 |
| Thr | Asn | Tyr | Thr | Leu | His | Val | Ile | Glu | Met | Lys | His | Asp | Ser | Ile | Arg | |
| | | | 365 | | | | | 370 | | | | | 375 | | | |
| AAG | ATT | GGT | TAC | TGG | AAT | GAA | GAT | GAT | AAG | TTT | GTC | CCT | GCA | GCC | ACC | 1322 |
| Lys | Ile | Gly | Tyr | Trp | Asn | Glu | Asp | Asp | Lys | Phe | Val | Pro | Ala | Ala | Thr | |
| | | 380 | | | | | 385 | | | | | 390 | | | | |
| GAT | GCC | CAA | GCT | GGG | GGC | GAT | AAT | TCA | AGT | GTT | CAG | AAC | AGA | ACA | TAC | 1370 |
| Asp | Ala | Gln | Ala | Gly | Gly | Asp | Asn | Ser | Ser | Val | Gln | Asn | Arg | Thr | Tyr | |
| | 395 | | | | | 400 | | | | | 405 | | | | | |
| ATC | GTC | ACA | ACA | ATC | CTA | GAA | GAT | CCT | TAT | GTG | ATG | CTC | AAG | AAG | AAC | 1418 |
| Ile | Val | Thr | Thr | Ile | Leu | Glu | Asp | Pro | Tyr | Val | Met | Leu | Lys | Lys | Asn | |
| 410 | | | | | 415 | | | | | 420 | | | | | 425 | |

```
GCC AAT CAG TTT GAG GGC AAT GAC CGT TAC GAG GGC TAC TGT GTA GAG      1466
Ala Asn Gln Phe Glu Gly Asn Asp Arg Tyr Glu Gly Tyr Cys Val Glu
            430                     435                     440

CTG GCG GCA GAG ATT GCC AAG CAC GTG GGC TAC TCC TAC CGT CTG GAG      1514
Leu Ala Ala Glu Ile Ala Lys His Val Gly Tyr Ser Tyr Arg Leu Glu
            445                     450                     455

ATT GTC AGT GAT GGA AAA TAC GGA GCC CGA GAC CCT GAC ACG AAG GCC      1562
Ile Val Ser Asp Gly Lys Tyr Gly Ala Arg Asp Pro Asp Thr Lys Ala
            460                     465                     470

TGG AAT GGC ATG GTG GGA GAG CTG GTC TAT GGA AGA GCA GAT GTG GCT      1610
Trp Asn Gly Met Val Gly Glu Leu Val Tyr Gly Arg Ala Asp Val Ala
            475                     480                     485

GTG GCT CCC TTA ACT ATC ACT TTG GTC CGG GAA GAA GTT ATA GAT TTC      1658
Val Ala Pro Leu Thr Ile Thr Leu Val Arg Glu Glu Val Ile Asp Phe
490                     495                     500                     505

TCC AAA CCA TTT ATG AGT TTG GGG ATC TCC ATC ATG ATT AAA AAA CCA      1706
Ser Lys Pro Phe Met Ser Leu Gly Ile Ser Ile Met Ile Lys Lys Pro
                510                     515                     520

CAG AAA TCC AAG CCG GGT GTC TTC TCC TTC CTT GAT CCT TTG GCT TAT      1754
Gln Lys Ser Lys Pro Gly Val Phe Ser Phe Leu Asp Pro Leu Ala Tyr
            525                     530                     535

GAG ATT TGG ATG TGC ATT GTT TTT GCC TAC ATT GGA GTG AGT GTT GTC      1802
Glu Ile Trp Met Cys Ile Val Phe Ala Tyr Ile Gly Val Ser Val Val
            540                     545                     550

CTC TTC CTG GTC AGC CGC TTC AGT CCC TAT GAA TGG CAC AGT GAA GAG      1850
Leu Phe Leu Val Ser Arg Phe Ser Pro Tyr Glu Trp His Ser Glu Glu
            555                     560                     565

TTT GAG GAA GGA CGG GAC CAG ACA ACC AGT GAC CAG TCC AAT GAG TTT      1898
Phe Glu Glu Gly Arg Asp Gln Thr Thr Ser Asp Gln Ser Asn Glu Phe
570                     575                     580                     585

GGG ATA TTC AAC AGT TTG TGG TTC TCC CTG GGA GCC TTC ATG CAG CAA      1946
Gly Ile Phe Asn Ser Leu Trp Phe Ser Leu Gly Ala Phe Met Gln Gln
                590                     595                     600

GGA TGT GAC ATT TCT CCC AGG TCC CTG TCT GGT CGC ATC GTT GGT GGC      1994
Gly Cys Asp Ile Ser Pro Arg Ser Leu Ser Gly Arg Ile Val Gly Gly
            605                     610                     615

GTC TGG TGG TTC TTC ACC TTA ATC ATC ATC TCC TCA TAT ACA GCC AAT      2042
Val Trp Trp Phe Phe Thr Leu Ile Ile Ile Ser Ser Tyr Thr Ala Asn
            620                     625                     630

CTG GCC GCC TTC CTG ACC GTG GAG AGG ATG GTG TCT CCC ATT GAG AGT      2090
Leu Ala Ala Phe Leu Thr Val Glu Arg Met Val Ser Pro Ile Glu Ser
            635                     640                     645

GCA GAG GAC CTA GCG AAG CAG ACA GAA ATT GCC TAC GGG ACG CTG GAA      2138
Ala Glu Asp Leu Ala Lys Gln Thr Glu Ile Ala Tyr Gly Thr Leu Glu
650                     655                     660                     665

GCA GGA TCT ACT AAG GAG TTC TTC AGG AGG TCT AAA ATT GCT GTG TTT      2186
Ala Gly Ser Thr Lys Glu Phe Phe Arg Arg Ser Lys Ile Ala Val Phe
                670                     675                     680

GAG AAG ATG TGG ACA TAC ATG AAG TCA GCA GAG CCA TCA GTT TTT GTG      2234
Glu Lys Met Trp Thr Tyr Met Lys Ser Ala Glu Pro Ser Val Phe Val
            685                     690                     695

CGG ACC ACA GAG GAG GGG ATG ATT CGA GTG AGG AAA TCC AAA GGC AAA      2282
Arg Thr Thr Glu Glu Gly Met Ile Arg Val Arg Lys Ser Lys Gly Lys
            700                     705                     710

TAT GCC TAC CTC CTG GAG TCC ACC ATG AAT GAG TAC ATT GAG CAG CGG      2330
Tyr Ala Tyr Leu Leu Glu Ser Thr Met Asn Glu Tyr Ile Glu Gln Arg
            715                     720                     725

AAA CCC TGT GAC ACC ATG AAG GTG GGA GGT AAC TTG GAT TCC AAA GGC      2378
Lys Pro Cys Asp Thr Met Lys Val Gly Gly Asn Leu Asp Ser Lys Gly
730                     735                     740                     745
```

-continued

| | | | | | | | | | | | | | | | | |
|---|---|---|---|---|---|---|---|---|---|---|---|---|---|---|---|---|
| TAT | GGC | ATT | GCA | ACA | CCC | AAG | GGG | TCT | GCC | CTG | GGA | AAT | CCA | GTA | AAC | 2426 |
| Tyr | Gly | Ile | Ala | Thr | Pro | Lys | Gly | Ser | Ala | Leu | Gly | Asn | Pro | Val | Asn | |
| | | | 750 | | | | | 755 | | | | | | 760 | | |
| CTG | GCA | GTG | TTA | AAA | CTA | AAC | GAG | CAG | GGG | CTT | TTG | GAC | AAA | TTG | AAA | 2474 |
| Leu | Ala | Val | Leu | Lys | Leu | Asn | Glu | Gln | Gly | Leu | Leu | Asp | Lys | Leu | Lys | |
| | | | 765 | | | | 770 | | | | | 775 | | | | |
| AAC | AAA | TGG | TGG | TAC | GAC | AAG | GGC | GAG | TGC | GGC | AGC | GGG | GGA | GGT | GAT | 2522 |
| Asn | Lys | Trp | Trp | Tyr | Asp | Lys | Gly | Glu | Cys | Gly | Ser | Gly | Gly | Gly | Asp | |
| | | 780 | | | | | 785 | | | | | 790 | | | | |
| TCC | AAG | GAC | AAG | ACA | AGC | GCT | CTG | AGC | CTC | AGC | AAT | GTG | GCA | GGC | GTG | 2570 |
| Ser | Lys | Asp | Lys | Thr | Ser | Ala | Leu | Ser | Leu | Ser | Asn | Val | Ala | Gly | Val | |
| | 795 | | | | | 800 | | | | | 805 | | | | | |
| TTC | TAC | ATC | CTG | ATC | GGA | GGA | CTT | GGA | CTA | GCC | ATG | CTG | GTT | GCC | TTA | 2618 |
| Phe | Tyr | Ile | Leu | Ile | Gly | Gly | Leu | Gly | Leu | Ala | Met | Leu | Val | Ala | Leu | |
| 810 | | | | | 815 | | | | | 820 | | | | | 825 | |
| ATC | GAG | TTC | TGC | TAC | AAA | TCC | CGT | AGT | GAA | TCC | AAG | CGG | ATG | AAG | GGT | 2666 |
| Ile | Glu | Phe | Cys | Tyr | Lys | Ser | Arg | Ser | Glu | Ser | Lys | Arg | Met | Lys | Gly | |
| | | | | 830 | | | | | 835 | | | | | 840 | | |
| TTT | TGT | TTG | ATC | CCA | CAG | CAA | TCC | ATC | AAC | GAA | GCC | ATA | CGG | ACA | TCG | 2714 |
| Phe | Cys | Leu | Ile | Pro | Gln | Gln | Ser | Ile | Asn | Glu | Ala | Ile | Arg | Thr | Ser | |
| | | | 845 | | | | | 850 | | | | | 855 | | | |
| ACC | CTC | CCC | CGC | AAC | AGC | GGG | GCA | GGA | GCC | AGC | AGC | GGC | GGC | AGT | GGA | 2762 |
| Thr | Leu | Pro | Arg | Asn | Ser | Gly | Ala | Gly | Ala | Ser | Ser | Gly | Gly | Ser | Gly | |
| | | 860 | | | | | 865 | | | | | 870 | | | | |
| GAG | AAT | GGT | CGG | GTG | GTC | AGC | CAT | GAC | TTC | CCC | AAG | TCC | ATG | CAA | TCG | 2810 |
| Glu | Asn | Gly | Arg | Val | Val | Ser | His | Asp | Phe | Pro | Lys | Ser | Met | Gln | Ser | |
| | 875 | | | | | 880 | | | | | 885 | | | | | |
| ATT | CCT | TGC | ATG | AGC | CAC | AGT | TCA | GGG | ATG | CCC | TTG | GGA | GCC | ACG | GGA | 2858 |
| Ile | Pro | Cys | Met | Ser | His | Ser | Ser | Gly | Met | Pro | Leu | Gly | Ala | Thr | Gly | |
| 890 | | | | | 895 | | | | | 900 | | | | | 905 | |

TTG TAACTGGAGC AGATGGAGAC CCCTTGGGGA GCAGGCTCGG CTCCCCAGCC   2911
Leu

CCATCCCAAA CCCTTCAGTG CCAAAAACAA CAAAA   2946

( 2 ) INFORMATION FOR SEQ ID NO:4:

( i ) SEQUENCE CHARACTERISTICS:
        ( A ) LENGTH: 906 amino acids
        ( B ) TYPE: amino acid
        ( D ) TOPOLOGY: linear ( i i ) MOLECULE TYPE: protein ( x i ) SEQUENCE DESCRIPTION: SEQ ID NO: 4:

| | | | | | | | | | | | | | | |
|---|---|---|---|---|---|---|---|---|---|---|---|---|---|---|
| Met | Gln | His | Ile | Phe | Ala | Phe | Phe | Cys | Thr | Gly | Phe | Leu | Gly | Ala | Val |
| 1 | | | | 5 | | | | | 10 | | | | | 15 | |
| Val | Gly | Ala | Asn | Phe | Pro | Asn | Asn | Ile | Gln | Ile | Gly | Gly | Leu | Phe | Pro |
| | | | 20 | | | | | 25 | | | | | 30 | | |
| Asn | Gln | Gln | Ser | Gln | Glu | His | Ala | Ala | Phe | Arg | Phe | Ala | Leu | Ser | Gln |
| | | | 35 | | | | 40 | | | | | 45 | | | |
| Leu | Thr | Glu | Pro | Pro | Lys | Leu | Leu | Pro | Gln | Ile | Asp | Ile | Val | Asn | Ile |
| | 50 | | | | | 55 | | | | | 60 | | | | |
| Ser | Asp | Ser | Phe | Glu | Met | Thr | Tyr | Arg | Phe | Cys | Ser | Gln | Phe | Ser | Lys |
| 65 | | | | | 70 | | | | | 75 | | | | | 80 |
| Gly | Val | Tyr | Ala | Ile | Phe | Gly | Phe | Tyr | Glu | Arg | Arg | Thr | Val | Asn | Met |
| | | | | 85 | | | | | 90 | | | | | 95 | |
| Leu | Thr | Ser | Phe | Cys | Gly | Ala | Leu | His | Val | Cys | Phe | Ile | Thr | Pro | Ser |
| | | | | 100 | | | | | 105 | | | | | 110 | |
| Phe | Pro | Val | Asp | Thr | Ser | Asn | Gln | Phe | Val | Leu | Gln | Leu | Arg | Pro | Glu |

|     |     |     |     | 115 |     |     |     |     | 120 |     |     |     |     | 125 |     |     |     |
|---|---|---|---|---|---|---|---|---|---|---|---|---|---|---|---|---|---|
| Leu | Gln | Asp | Ala | Leu | Ile | Ser | Ile | Ile | Asp | His | Tyr | Lys | Trp | Gln | Lys |
|     |     | 130 |     |     |     | 135 |     |     |     | 140 |     |     |     |     |     |
| Phe | Val | Tyr | Ile | Tyr | Asp | Ala | Asp | Arg | Gly | Leu | Ser | Val | Leu | Gln | Lys |
| 145 |     |     |     |     | 150 |     |     |     |     | 155 |     |     |     |     | 160 |
| Val | Leu | Asp | Thr | Ala | Ala | Glu | Lys | Asn | Trp | Gln | Val | Thr | Ala | Val | Asn |
|     |     |     |     | 165 |     |     |     |     | 170 |     |     |     |     | 175 |     |
| Ile | Leu | Thr | Thr | Thr | Glu | Glu | Gly | Tyr | Arg | Met | Leu | Phe | Gln | Asp | Leu |
|     |     |     | 180 |     |     |     |     | 185 |     |     |     |     | 190 |     |     |
| Glu | Lys | Lys | Lys | Glu | Arg | Leu | Val | Val | Asp | Cys | Glu | Ser | Glu | Arg |     |
|     |     | 195 |     |     |     |     | 200 |     |     |     | 205 |     |     |     |     |
| Leu | Asn | Ala | Ile | Leu | Gly | Gln | Ile | Ile | Lys | Leu | Glu | Lys | Asn | Gly | Ile |
|     | 210 |     |     |     |     | 215 |     |     |     |     | 220 |     |     |     |     |
| Gly | Tyr | His | Tyr | Ile | Leu | Ala | Asn | Leu | Gly | Phe | Met | Asp | Ile | Asp | Leu |
| 225 |     |     |     |     | 230 |     |     |     |     | 235 |     |     |     |     | 240 |
| Asn | Lys | Phe | Lys | Glu | Ser | Gly | Ala | Asn | Val | Thr | Gly | Phe | Gln | Leu | Val |
|     |     |     |     | 245 |     |     |     |     | 250 |     |     |     |     | 255 |     |
| Asn | Tyr | Thr | Asp | Thr | Ile | Pro | Ala | Lys | Ile | Met | Gln | Gln | Trp | Lys | Asn |
|     |     |     | 260 |     |     |     |     | 265 |     |     |     |     | 270 |     |     |
| Ser | Asp | Ala | Arg | Asp | His | Thr | Arg | Val | Asp | Trp | Lys | Arg | Pro | Lys | Tyr |
|     |     | 275 |     |     |     |     | 280 |     |     |     |     | 285 |     |     |     |
| Thr | Ser | Ala | Leu | Thr | Tyr | Asp | Gly | Val | Lys | Val | Met | Ala | Glu | Ala | Phe |
|     | 290 |     |     |     |     | 295 |     |     |     |     | 300 |     |     |     |     |
| Gln | Ser | Leu | Arg | Arg | Gln | Arg | Ile | Asp | Ile | Ser | Arg | Arg | Gly | Asn | Ala |
| 305 |     |     |     |     | 310 |     |     |     |     | 315 |     |     |     |     | 320 |
| Gly | Asp | Cys | Leu | Ala | Asn | Pro | Ala | Val | Pro | Trp | Gly | Gln | Gly | Ile | Asp |
|     |     |     |     | 325 |     |     |     |     | 330 |     |     |     |     | 335 |     |
| Ile | Gln | Arg | Ala | Leu | Gln | Gln | Val | Arg | Phe | Glu | Gly | Leu | Thr | Gly | Asn |
|     |     |     | 340 |     |     |     |     | 345 |     |     |     |     | 350 |     |     |
| Val | Gln | Phe | Asn | Glu | Lys | Gly | Arg | Arg | Thr | Asn | Tyr | Thr | Leu | His | Val |
|     |     | 355 |     |     |     |     | 360 |     |     |     |     | 365 |     |     |     |
| Ile | Glu | Met | Lys | His | Asp | Ser | Ile | Arg | Lys | Ile | Gly | Tyr | Trp | Asn | Glu |
|     | 370 |     |     |     |     | 375 |     |     |     |     | 380 |     |     |     |     |
| Asp | Asp | Lys | Phe | Val | Pro | Ala | Ala | Thr | Asp | Ala | Gln | Ala | Gly | Gly | Asp |
| 385 |     |     |     |     | 390 |     |     |     |     | 395 |     |     |     |     | 400 |
| Asn | Ser | Ser | Val | Gln | Asn | Arg | Thr | Tyr | Ile | Val | Thr | Thr | Ile | Leu | Glu |
|     |     |     |     | 405 |     |     |     |     | 410 |     |     |     |     | 415 |     |
| Asp | Pro | Tyr | Val | Met | Leu | Lys | Lys | Asn | Ala | Asn | Gln | Phe | Glu | Gly | Asn |
|     |     |     | 420 |     |     |     |     | 425 |     |     |     |     | 430 |     |     |
| Asp | Arg | Tyr | Glu | Gly | Tyr | Cys | Val | Glu | Leu | Ala | Ala | Glu | Ile | Ala | Lys |
|     |     | 435 |     |     |     |     | 440 |     |     |     |     | 445 |     |     |     |
| His | Val | Gly | Tyr | Ser | Tyr | Arg | Leu | Glu | Ile | Val | Ser | Asp | Gly | Lys | Tyr |
|     | 450 |     |     |     |     | 455 |     |     |     |     | 460 |     |     |     |     |
| Gly | Ala | Arg | Asp | Pro | Asp | Thr | Lys | Ala | Trp | Asn | Gly | Met | Val | Gly | Glu |
| 465 |     |     |     |     | 470 |     |     |     |     | 475 |     |     |     |     | 480 |
| Leu | Val | Tyr | Gly | Arg | Ala | Asp | Val | Ala | Val | Ala | Pro | Leu | Thr | Ile | Thr |
|     |     |     |     | 485 |     |     |     |     | 490 |     |     |     |     | 495 |     |
| Leu | Val | Arg | Glu | Glu | Val | Ile | Asp | Phe | Ser | Lys | Pro | Phe | Met | Ser | Leu |
|     |     |     | 500 |     |     |     |     | 505 |     |     |     |     | 510 |     |     |
| Gly | Ile | Ser | Ile | Met | Ile | Lys | Lys | Pro | Gln | Lys | Ser | Lys | Pro | Gly | Val |
|     |     | 515 |     |     |     |     | 520 |     |     |     |     | 525 |     |     |     |
| Phe | Ser | Phe | Leu | Asp | Pro | Leu | Ala | Tyr | Glu | Ile | Trp | Met | Cys | Ile | Val |
|     | 530 |     |     |     |     | 535 |     |     |     |     | 540 |     |     |     |     |

| | | | | | | | | | | | | | | |
|---|---|---|---|---|---|---|---|---|---|---|---|---|---|---|
| Phe 545 | Ala | Tyr | Ile | Gly | Val 550 | Ser | Val | Val | Leu | Phe 555 | Leu | Val | Ser | Arg | Phe 560 |
| Ser | Pro | Tyr | Glu | Trp 565 | His | Ser | Glu | Glu | Phe 570 | Glu | Glu | Gly | Arg | Asp 575 | Gln |
| Thr | Thr | Ser | Asp 580 | Gln | Ser | Asn | Glu | Phe 585 | Gly | Ile | Phe | Asn | Ser 590 | Leu | Trp |
| Phe | Ser | Leu 595 | Gly | Ala | Phe | Met | Gln 600 | Gln | Gly | Cys | Asp | Ile 605 | Ser | Pro | Arg |
| Ser | Leu 610 | Ser | Gly | Arg | Ile | Val 615 | Gly | Gly | Val | Trp | Trp 620 | Phe | Phe | Thr | Leu |
| Ile 625 | Ile | Ile | Ser | Ser | Tyr 630 | Thr | Ala | Asn | Leu | Ala 635 | Ala | Phe | Leu | Thr | Val 640 |
| Glu | Arg | Met | Val | Ser 645 | Pro | Ile | Glu | Ser | Ala 650 | Glu | Asp | Leu | Ala | Lys 655 | Gln |
| Thr | Glu | Ile | Ala 660 | Tyr | Gly | Thr | Leu | Glu 665 | Ala | Gly | Ser | Thr | Lys 670 | Glu | Phe |
| Phe | Arg | Arg 675 | Ser | Lys | Ile | Ala | Val 680 | Phe | Glu | Lys | Met | Trp 685 | Thr | Tyr | Met |
| Lys | Ser | Ala | Glu 690 | Pro | Ser | Val 695 | Phe | Val | Arg | Thr | Thr 700 | Glu | Glu | Gly | Met |
| Ile | Arg | Val | Arg | Lys 710 | Ser | Lys | Gly | Lys | Tyr | Ala 715 | Tyr | Leu | Leu | Glu | Ser 720 |
| | | | | | | | | | | | | | | |
| Ile 705 | | | | | | | | | | | | | | | |
| Thr | Met | Asn | Glu | Tyr 725 | Ile | Glu | Gln | Arg | Lys 730 | Pro | Cys | Asp | Thr | Met 735 | Lys |
| Val | Gly | Gly | Asn 740 | Leu | Asp | Ser | Lys | Gly 745 | Tyr | Gly | Ile | Ala | Thr 750 | Pro | Lys |
| Gly | Ser | Ala 755 | Leu | Gly | Asn | Pro | Val 760 | Asn | Leu | Ala | Val | Leu 765 | Lys | Leu | Asn |
| Glu | Gln | Gly 770 | Leu | Leu | Asp | Lys 775 | Leu | Lys | Asn | Lys | Trp 780 | Trp | Tyr | Asp | Lys |
| Gly 785 | Glu | Cys | Gly | Ser | Gly 790 | Gly | Gly | Asp | Ser | Lys 795 | Asp | Lys | Thr | Ser | Ala 800 |
| Leu | Ser | Leu | Ser | Asn 805 | Val | Ala | Gly | Val | Phe 810 | Tyr | Ile | Leu | Ile 815 | Gly | Gly |
| Leu | Gly | Leu | Ala 820 | Met | Leu | Val | Ala | Leu 825 | Ile | Glu | Phe | Cys | Tyr 830 | Lys | Ser |
| Arg | Ser | Glu 835 | Ser | Lys | Arg | Met | Lys 840 | Gly | Phe | Cys | Leu | Ile 845 | Pro | Gln | Gln |
| Ser | Ile 850 | Asn | Glu | Ala | Ile | Arg 855 | Thr | Ser | Thr | Leu | Pro 860 | Arg | Asn | Ser | Gly |
| Ala 865 | Gly | Ala | Ser | Ser | Gly 870 | Gly | Ser | Gly | Glu | Asn 875 | Gly | Arg | Val | Val | Ser 880 |
| His | Asp | Phe | Pro | Lys 885 | Ser | Met | Gln | Ser | Ile 890 | Pro | Cys | Met | Ser | His 895 | Ser |
| Ser | Gly | Met | Pro 900 | Leu | Gly | Ala | Thr | Gly 905 | Leu | | | | | | |

( 2 ) INFORMATION FOR SEQ ID NO: 5:

( i ) SEQUENCE CHARACTERISTICS:
        ( A ) LENGTH: 2955 base pairs
        ( B ) TYPE: nucleic acid
        ( C ) STRANDEDNESS: single
        ( D ) TOPOLOGY: linear ( i i ) MOLECULE TYPE: cDNA to mRNA 5,756,697

-continued (v i) ORIGINAL SOURCE:
  (A) ORGANISM: Homo sapiens
  (B) DEVELOPMENTAL STAGE: Adult
  (C) TISSUE TYPE: Brain (i x) FEATURE:
  (A) NAME/KEY: CDS
  (B) LOCATION: 28..2676

(x i) SEQUENCE DESCRIPTION: SEQ ID NO: 5:

```
TTTGTCGACG CTCTACTTTT CTTGGAA ATG CAA AAG ATT ATG CAT GTT TCT              51
                               Met Gln Lys Ile Met His Val Ser
                                 1               5

GTC CTC CTT TCT CCT GTT TTA TGG GGA CTG ATT TTT GGT GTC TCT TCT            99
Val Leu Leu Ser Pro Val Leu Trp Gly Leu Ile Phe Gly Val Ser Ser
         10              15                  20

AAC AGC ATA CAG ATA GGG GGG CTA TTT CCT AGG GGC GCC GAT CAA GAA           147
Asn Ser Ile Gln Ile Gly Gly Leu Phe Pro Arg Gly Ala Asp Gln Glu
 25              30                  35                      40

TAC AGT GCA TTT CGA GTA GGG ATG GTT CAG TTT TCC ACT TCG GAG TTC           195
Tyr Ser Ala Phe Arg Val Gly Met Val Gln Phe Ser Thr Ser Glu Phe
             45                  50                  55

AGA CTG ACA CCC CAC ATC GAC AAT TTG GAG GTG GCA AAC AGC TTC GCA           243
Arg Leu Thr Pro His Ile Asp Asn Leu Glu Val Ala Asn Ser Phe Ala
                 60              65                  70

GTC ACT AAT GCT TTC TGC TCC CAG TTT TCG AGA GGA GTC TAT GCT ATT           291
Val Thr Asn Ala Phe Cys Ser Gln Phe Ser Arg Gly Val Tyr Ala Ile
             75                  80                  85

TTT GGA TTT TAT GAC AAG AAG TCT GTA AAT ACC ATC ACA TCA TTT TGC           339
Phe Gly Phe Tyr Asp Lys Lys Ser Val Asn Thr Ile Thr Ser Phe Cys
         90                  95                 100

GGA ACA CTC CAC GTC TCC TTC ATC ACT CCC AGC TTC CCA ACA GAT GGC           387
Gly Thr Leu His Val Ser Phe Ile Thr Pro Ser Phe Pro Thr Asp Gly
105                 110                 115                 120

ACA CAT CCA TTT GTC ATT CAG ATG AGA CCC GAC CTC AAA GGA GCT CTC           435
Thr His Pro Phe Val Ile Gln Met Arg Pro Asp Leu Lys Gly Ala Leu
             125                 130                 135

CTT AGC TTG ATT GAA TAC TAT CAA TGG GAC AAG TTT GCA TAC CTC TAT           483
Leu Ser Leu Ile Glu Tyr Tyr Gln Trp Asp Lys Phe Ala Tyr Leu Tyr
             140                 145                 150

GAC AGT GAC AGA GGC TTA TCA ACA CTG CAA GCT GTG CTG GAT TCT GCT           531
Asp Ser Asp Arg Gly Leu Ser Thr Leu Gln Ala Val Leu Asp Ser Ala
         155                 160                 165

GCT GAA AAG AAA TGG CAA GTG ACT GCT ATC AAT GTG GGA AAC ATT AAC           579
Ala Glu Lys Lys Trp Gln Val Thr Ala Ile Asn Val Gly Asn Ile Asn
     170                 175                 180

AAT GAC AAG AAA GAT GAG ATG TAC CGA TCA CTT TTT CAA GAT CTG GAG           627
Asn Asp Lys Lys Asp Glu Met Tyr Arg Ser Leu Phe Gln Asp Leu Glu
185                 190                 195                 200

TTA AAA AAG GAA CGG CGT GTA ATT CTG GAC TGT GAA AGG GAT AAA GTA           675
Leu Lys Lys Glu Arg Arg Val Ile Leu Asp Cys Glu Arg Asp Lys Val
                 205                 210                 215

AAC GAC ATT GTA GAC CAG GTT ATT ACC ATT GGA AAA CAC GTT AAA GGG           723
Asn Asp Ile Val Asp Gln Val Ile Thr Ile Gly Lys His Val Lys Gly
             220                 225                 230

TAC CAC TAC ATC ATT GCA AAT CTG GGA TTT ACT GAT GGA GAC CTA TTA           771
Tyr His Tyr Ile Ile Ala Asn Leu Gly Phe Thr Asp Gly Asp Leu Leu
             235                 240                 245

AAA ATC CAG TTT GGA GGT GCA AAT GTC TCT GGA TTT CAG ATA GTG GAC           819
Lys Ile Gln Phe Gly Gly Ala Asn Val Ser Gly Phe Gln Ile Val Asp
         250                 255                 260

TAT GAT GAT TCG TTG GTA TCT AAA TTT ATA GAA AGA TGG TCA ACA CTG           867
```

| | | | | | | | | | | | | | | | | |
|---|---|---|---|---|---|---|---|---|---|---|---|---|---|---|---|---|
| Tyr | Asp | Asp | Ser | Leu | Val | Ser | Lys | Phe | Ile | Glu | Arg | Trp | Ser | Thr | Leu | |
| 265 | | | | 270 | | | | | 275 | | | | | 280 | | |
| GAA | GAA | AAA | GAA | TAC | CCT | GGA | GCT | CAC | ACA | ACA | ACA | ATT | AAG | TAT | ACT | 915 |
| Glu | Glu | Lys | Glu | Tyr | Pro | Gly | Ala | His | Thr | Thr | Thr | Ile | Lys | Tyr | Thr | |
| | | | | 285 | | | | | 290 | | | | | 295 | | |
| TCT | GCT | CTG | ACC | TAT | GAT | GCC | GTT | CAA | GTG | ATG | ACT | GAA | GCC | TTC | CGC | 963 |
| Ser | Ala | Leu | Thr | Tyr | Asp | Ala | Val | Gln | Val | Met | Thr | Glu | Ala | Phe | Arg | |
| | | | 300 | | | | | 305 | | | | | 310 | | | |
| AAC | CTA | AGG | AAG | CAA | AGA | ATT | GAA | ATC | TCC | CGA | AGG | GGG | AAT | GCA | GGA | 1011 |
| Asn | Leu | Arg | Lys | Gln | Arg | Ile | Glu | Ile | Ser | Arg | Arg | Gly | Asn | Ala | Gly | |
| | | 315 | | | | | 320 | | | | | 325 | | | | |
| GAC | TGT | CTG | GCA | AAC | CCA | GCA | GTG | CCC | TGG | GGA | CAA | GGT | GTA | GAA | ATA | 1059 |
| Asp | Cys | Leu | Ala | Asn | Pro | Ala | Val | Pro | Trp | Gly | Gln | Gly | Val | Glu | Ile | |
| | 330 | | | | 335 | | | | | 340 | | | | | | |
| GAA | AGG | GCC | CTC | AAA | CAG | GTT | CAG | GTT | GAA | GGT | CTC | TCA | GGA | AAT | ATA | 1107 |
| Glu | Arg | Ala | Leu | Lys | Gln | Val | Gln | Val | Glu | Gly | Leu | Ser | Gly | Asn | Ile | |
| 345 | | | | 350 | | | | | 355 | | | | | 360 | | |
| AAG | TTT | GAC | CAG | AAT | GGA | AAA | AGA | ATA | AAC | TAT | ACA | ATT | AAC | ATC | ATG | 1155 |
| Lys | Phe | Asp | Gln | Asn | Gly | Lys | Arg | Ile | Asn | Tyr | Thr | Ile | Asn | Ile | Met | |
| | | | | 365 | | | | | 370 | | | | | 375 | | |
| GAG | CTC | AAA | ACT | AAT | GGG | CCC | CGG | AAG | ATT | GGC | TAC | TGG | AGT | GAA | GTG | 1203 |
| Glu | Leu | Lys | Thr | Asn | Gly | Pro | Arg | Lys | Ile | Gly | Tyr | Trp | Ser | Glu | Val | |
| | | | 380 | | | | | 385 | | | | | 390 | | | |
| GAC | AAA | ATG | GTT | GTT | ACC | CTT | ACT | GAG | CTC | CCT | TCT | GGA | AAT | GAC | ACC | 1251 |
| Asp | Lys | Met | Val | Val | Thr | Leu | Thr | Glu | Leu | Pro | Ser | Gly | Asn | Asp | Thr | |
| | | 395 | | | | | 400 | | | | | 405 | | | | |
| TCT | GGG | CTT | GAG | AAT | AAG | ACT | GTT | GTT | GTC | ACC | ACA | ATT | TTG | GAA | TCT | 1299 |
| Ser | Gly | Leu | Glu | Asn | Lys | Thr | Val | Val | Val | Thr | Thr | Ile | Leu | Glu | Ser | |
| | 410 | | | | 415 | | | | | 420 | | | | | | |
| CCG | TAT | GTT | ATG | ATG | AAG | AAA | AAT | CAT | GAA | ATG | CTT | GAA | GGC | AAT | GAG | 1347 |
| Pro | Tyr | Val | Met | Met | Lys | Lys | Asn | His | Glu | Met | Leu | Glu | Gly | Asn | Glu | |
| 425 | | | | 430 | | | | | 435 | | | | | 440 | | |
| CGC | TAT | GAG | GGC | TAC | TGT | GTT | GAC | CTG | GCT | GCA | GAA | ATC | GCC | AAA | CAT | 1395 |
| Arg | Tyr | Glu | Gly | Tyr | Cys | Val | Asp | Leu | Ala | Ala | Glu | Ile | Ala | Lys | His | |
| | | | | 445 | | | | | 450 | | | | | 455 | | |
| TGT | GGG | TTC | AAG | TAC | AAG | TTG | ACA | ATT | GTT | GGT | GAT | GGC | AAG | TAT | GGG | 1443 |
| Cys | Gly | Phe | Lys | Tyr | Lys | Leu | Thr | Ile | Val | Gly | Asp | Gly | Lys | Tyr | Gly | |
| | | | 460 | | | | | 465 | | | | | 470 | | | |
| GCC | AGG | GAT | GCA | GAC | ACG | AAA | ATT | TGG | AAT | GGG | ATG | GTT | GGA | GAA | CTT | 1491 |
| Ala | Arg | Asp | Ala | Asp | Thr | Lys | Ile | Trp | Asn | Gly | Met | Val | Gly | Glu | Leu | |
| | 475 | | | | | 480 | | | | | 485 | | | | | |
| GTA | TAT | GGG | AAA | GCT | GAT | ATT | GCA | ATT | GCT | CCA | TTA | ACT | ATT | ACC | CTT | 1539 |
| Val | Tyr | Gly | Lys | Ala | Asp | Ile | Ala | Ile | Ala | Pro | Leu | Thr | Ile | Thr | Leu | |
| | 490 | | | | 495 | | | | | 500 | | | | | | |
| GTG | AGA | GAA | GAG | GTG | ATT | GAC | TTC | TCA | AAG | CCC | TTC | ATG | AGC | CTC | GGG | 1587 |
| Val | Arg | Glu | Glu | Val | Ile | Asp | Phe | Ser | Lys | Pro | Phe | Met | Ser | Leu | Gly | |
| 505 | | | | 510 | | | | | 515 | | | | | 520 | | |
| ATA | TCT | ATC | ATG | ATC | AAG | AAG | CCT | CAG | AAG | TCC | AAA | CCA | GGA | GTG | TTT | 1635 |
| Ile | Ser | Ile | Met | Ile | Lys | Lys | Pro | Gln | Lys | Ser | Lys | Pro | Gly | Val | Phe | |
| | | | 525 | | | | | 530 | | | | | 535 | | | |
| TCC | TTT | CTT | GAT | CCT | TTA | GCC | TAT | GAG | ATC | TGG | ATG | TGC | ATT | GTT | TTT | 1683 |
| Ser | Phe | Leu | Asp | Pro | Leu | Ala | Tyr | Glu | Ile | Trp | Met | Cys | Ile | Val | Phe | |
| | | | 540 | | | | | 545 | | | | | 550 | | | |
| GCC | TAC | ATT | GGG | GTC | AGT | GTA | GTT | TTA | TTC | CTG | GTC | AGC | AGA | TTT | AGC | 1731 |
| Ala | Tyr | Ile | Gly | Val | Ser | Val | Val | Leu | Phe | Leu | Val | Ser | Arg | Phe | Ser | |
| | | 555 | | | | | 560 | | | | | 565 | | | | |
| CCC | TAC | GAG | TGG | CAC | ACT | GAG | GAG | TTT | GAA | GAT | GGA | AGA | GAA | ACA | CAA | 1779 |
| Pro | Tyr | Glu | Trp | His | Thr | Glu | Glu | Phe | Glu | Asp | Gly | Arg | Glu | Thr | Gln | |
| | | 570 | | | | | 575 | | | | | 580 | | | | |
| AGT | AGT | GAA | TCA | ACT | AAT | GAA | TTT | GGG | ATT | TTT | AAT | AGT | CTC | TGG | TTT | 1827 |

|       |       |       |       |       |       |       |       |       |       |       |       |       |       |       |      |
|-------|-------|-------|-------|-------|-------|-------|-------|-------|-------|-------|-------|-------|-------|-------|------|
| Ser   | Ser   | Glu   | Ser   | Thr   | Asn   | Glu   | Phe   | Gly   | Ile   | Phe   | Asn   | Ser   | Leu   | Trp   | Phe  |
| 585   |       |       |       |       | 590   |       |       |       | 595   |       |       |       |       | 600   |      |
| TCC   | TTG   | GGT   | GCC   | TTT   | ATG   | CGG   | CAA   | GGA   | TGC   | GAT   | ATT   | TCG   | CCA   | AGA   | TCC  | 1875 |
| Ser   | Leu   | Gly   | Ala   | Phe   | Met   | Arg   | Gln   | Gly   | Cys   | Asp   | Ile   | Ser   | Pro   | Arg   | Ser  |
|       |       |       |       | 605   |       |       |       |       | 610   |       |       |       |       | 615   |      |
| CTC   | TCT   | GGG   | CGC   | ATT   | GTT   | GGA   | GGT   | GTG   | TGG   | TGG   | TTC   | TTT   | ACC   | CTG   | ATC  | 1923 |
| Leu   | Ser   | Gly   | Arg   | Ile   | Val   | Gly   | Gly   | Val   | Trp   | Trp   | Phe   | Phe   | Thr   | Leu   | Ile  |
|       |       |       | 620   |       |       |       |       | 625   |       |       |       |       | 630   |       |      |
| ATA   | ATC   | TCC   | TCC   | TAC   | ACG   | GCT   | AAC   | TTA   | GCT   | GCC   | TTC   | CTG   | ACT   | GTA   | GAG  | 1971 |
| Ile   | Ile   | Ser   | Ser   | Tyr   | Thr   | Ala   | Asn   | Leu   | Ala   | Ala   | Phe   | Leu   | Thr   | Val   | Glu  |
|       |       | 635   |       |       |       |       | 640   |       |       |       |       | 645   |       |       |      |
| AGG   | ATG   | GTG   | TCT   | CCC   | ATC   | GAA   | AGT   | GCT   | GAG   | GAT   | CTT   | TCT   | AAG   | CAA   | ACA  | 2019 |
| Arg   | Met   | Val   | Ser   | Pro   | Ile   | Glu   | Ser   | Ala   | Glu   | Asp   | Leu   | Ser   | Lys   | Gln   | Thr  |
|       | 650   |       |       |       | 655   |       |       |       |       | 660   |       |       |       |       |      |
| GAA   | ATT   | GCT   | TAT   | GGA   | ACA   | TTA   | GAC   | TCT   | GGC   | TCC   | ACT   | AAA   | GAG   | TTT   | TTC  | 2067 |
| Glu   | Ile   | Ala   | Tyr   | Gly   | Thr   | Leu   | Asp   | Ser   | Gly   | Ser   | Thr   | Lys   | Glu   | Phe   | Phe  |
| 665   |       |       |       | 670   |       |       |       |       | 675   |       |       |       |       | 680   |      |
| AGG   | AGA   | TCT   | AAA   | ATT   | GCA   | GTG   | TTT   | GAT   | AAA   | ATG   | TGG   | ACC   | TAC   | ATG   | CGG  | 2115 |
| Arg   | Arg   | Ser   | Lys   | Ile   | Ala   | Val   | Phe   | Asp   | Lys   | Met   | Trp   | Thr   | Tyr   | Met   | Arg  |
|       |       |       |       | 685   |       |       |       |       | 690   |       |       |       |       | 695   |      |
| AGT   | GCG   | GAG   | CCC   | TCT   | GTG   | TTT   | GTG   | AGG   | ACT   | ACG   | GCC   | GAA   | GGG   | GTG   | GCT  | 2163 |
| Ser   | Ala   | Glu   | Pro   | Ser   | Val   | Phe   | Val   | Arg   | Thr   | Thr   | Ala   | Glu   | Gly   | Val   | Ala  |
|       |       |       | 700   |       |       |       |       | 705   |       |       |       |       | 710   |       |      |
| AGA   | GTG   | CGG   | AAG   | TCC   | AAA   | GGG   | AAA   | TAT   | GCC   | TAC   | TTG   | TTG   | GAG   | TCC   | ACG  | 2211 |
| Arg   | Val   | Arg   | Lys   | Ser   | Lys   | Gly   | Lys   | Tyr   | Ala   | Tyr   | Leu   | Leu   | Glu   | Ser   | Thr  |
|       |       | 715   |       |       |       |       | 720   |       |       |       |       | 725   |       |       |      |
| ATG   | AAC   | GAG   | TAC   | ATT   | GAG   | CAA   | AGG   | AAG   | CCT   | TGC   | GAC   | ACC   | ATG   | AAA   | GTT  | 2259 |
| Met   | Asn   | Glu   | Tyr   | Ile   | Glu   | Gln   | Arg   | Lys   | Pro   | Cys   | Asp   | Thr   | Met   | Lys   | Val  |
|       | 730   |       |       |       |       | 735   |       |       |       |       | 740   |       |       |       |      |
| GGT   | GGA   | AAC   | CTG   | GAT   | TCC   | AAA   | GGC   | TAT   | GGC   | ATC   | GCA   | ACA   | CCT   | AAA   | GGA  | 2307 |
| Gly   | Gly   | Asn   | Leu   | Asp   | Ser   | Lys   | Gly   | Tyr   | Gly   | Ile   | Ala   | Thr   | Pro   | Lys   | Gly  |
| 745   |       |       |       |       | 750   |       |       |       |       | 755   |       |       |       |       | 760  |
| TCC   | TCA   | TTA   | GGA   | ACC   | CCA   | GTA   | AAT   | CTT   | GCA   | GTA   | TTG   | AAA   | CTC   | AGT   | GAG  | 2355 |
| Ser   | Ser   | Leu   | Gly   | Thr   | Pro   | Val   | Asn   | Leu   | Ala   | Val   | Leu   | Lys   | Leu   | Ser   | Glu  |
|       |       |       |       | 765   |       |       |       |       | 770   |       |       |       |       | 775   |      |
| CAA   | GGC   | GTC   | TTA   | GAC   | AAG   | CTG   | AAA   | AAC   | AAA   | TGG   | TGG   | TAC   | GAT   | AAA   | GGT  | 2403 |
| Gln   | Gly   | Val   | Leu   | Asp   | Lys   | Leu   | Lys   | Asn   | Lys   | Trp   | Trp   | Tyr   | Asp   | Lys   | Gly  |
|       |       |       | 780   |       |       |       |       | 785   |       |       |       |       | 790   |       |      |
| GAA   | TGT   | GGA   | GCC   | AAG   | GAC   | TCT   | GGA   | AGT   | AAG   | GAA   | AAG   | ACC   | AGT   | GCC   | CTC  | 2451 |
| Glu   | Cys   | Gly   | Ala   | Lys   | Asp   | Ser   | Gly   | Ser   | Lys   | Glu   | Lys   | Thr   | Ser   | Ala   | Leu  |
|       |       | 795   |       |       |       |       | 800   |       |       |       |       | 805   |       |       |      |
| AGT   | CTG   | AGC   | AAC   | GTT   | GCT   | GGA   | GTA   | TTC   | TAC   | ATC   | CTT   | GTC   | GGG   | GGC   | CTT  | 2499 |
| Ser   | Leu   | Ser   | Asn   | Val   | Ala   | Gly   | Val   | Phe   | Tyr   | Ile   | Leu   | Val   | Gly   | Gly   | Leu  |
|       | 810   |       |       |       |       | 815   |       |       |       |       | 820   |       |       |       |      |
| GGT   | TTG   | GCA   | ATG   | CTG   | GTG   | GCT   | TTG   | ATT   | GAG   | TTC   | TGT   | TAC   | AAG   | TCA   | AGG  | 2547 |
| Gly   | Leu   | Ala   | Met   | Leu   | Val   | Ala   | Leu   | Ile   | Glu   | Phe   | Cys   | Tyr   | Lys   | Ser   | Arg  |
| 825   |       |       |       |       | 830   |       |       |       |       | 835   |       |       |       |       | 840  |
| GCC   | GAG   | GCG   | AAA   | CGA   | ATG   | AAG   | GTG   | GCA   | AAG   | AAT   | GCA   | CAG   | AAT   | ATT   | AAC  | 2595 |
| Ala   | Glu   | Ala   | Lys   | Arg   | Met   | Lys   | Val   | Ala   | Lys   | Asn   | Ala   | Gln   | Asn   | Ile   | Asn  |
|       |       |       |       | 845   |       |       |       |       | 850   |       |       |       |       | 855   |      |
| CCA   | TCT   | TCC   | TCG   | CAG   | AAT   | TCA   | CAG   | AAT   | TTT   | GCA   | ACT   | TAT   | AAG   | GAA   | GGT  | 2643 |
| Pro   | Ser   | Ser   | Ser   | Gln   | Asn   | Ser   | Gln   | Asn   | Phe   | Ala   | Thr   | Tyr   | Lys   | Glu   | Gly  |
|       |       |       | 860   |       |       |       |       | 865   |       |       |       |       | 870   |       |      |
| TAC   | AAC   | GTA   | TAT   | GGC   | ATC   | GAA   | AGT   | GTT   | AAA   | ATT   | TAGGGGATGA | CCTTGAAATG | | | | 2696 |
| Tyr   | Asn   | Val   | Tyr   | Gly   | Ile   | Glu   | Ser   | Val   | Lys   | Ile   |       |       |       |       |      |
|       |       | 875   |       |       |       |       | 880   |       |       |       |       |       |       |       |      |

ATGCCATGAG GAACAAGGCA AGGCTGTCAA TTACAGGAAG TACTGGAGAA AATGGACGTG   2756

TTATGACTCC AGAATTTCCC AAAGCAGTGC ATGCTGTCCC TTACGTGAGT CCTGGCATGG   2816

GAATGAATGT CAGTGTGACT GATCTCTCGT GATTGATAAG AACCTTTTGA GTGCCTTACA   2876

```
CAATGGTTTT CTTGTGTTTA TTGTCAAAGT GGTGAGAGGC ATCCAGTATC TTGAAGACTT    2936

TTCTTTCAGC CAAGAATTC                                                 2955
```

( 2 ) INFORMATION FOR SEQ ID NO:6:

( i ) SEQUENCE CHARACTERISTICS:
        ( A ) LENGTH: 883 amino acids
        ( B ) TYPE: amino acid
        ( D ) TOPOLOGY: linear ( i i ) MOLECULE TYPE: protein ( x i ) SEQUENCE DESCRIPTION: SEQ ID NO: 6:

```
Met Gln Lys Ile Met His Val Ser Val Leu Leu Ser Pro Val Leu Trp
 1               5                  10                  15

Gly Leu Ile Phe Gly Val Ser Ser Asn Ser Ile Gln Ile Gly Gly Leu
            20                  25                  30

Phe Pro Arg Gly Ala Asp Gln Glu Tyr Ser Ala Phe Arg Val Gly Met
        35                  40                  45

Val Gln Phe Ser Thr Ser Glu Phe Arg Leu Thr Pro His Ile Asp Asn
 50                  55                  60

Leu Glu Val Ala Asn Ser Phe Ala Val Thr Asn Ala Phe Cys Ser Gln
 65                  70                  75                  80

Phe Ser Arg Gly Val Tyr Ala Ile Phe Gly Phe Tyr Asp Lys Lys Ser
                 85                  90                  95

Val Asn Thr Ile Thr Ser Phe Cys Gly Thr Leu His Val Ser Phe Ile
            100                 105                 110

Thr Pro Ser Phe Pro Thr Asp Gly Thr His Pro Phe Val Ile Gln Met
        115                 120                 125

Arg Pro Asp Leu Lys Gly Ala Leu Leu Ser Leu Ile Glu Tyr Tyr Gln
130                 135                 140

Trp Asp Lys Phe Ala Tyr Leu Tyr Asp Ser Asp Arg Gly Leu Ser Thr
145                 150                 155                 160

Leu Gln Ala Val Leu Asp Ser Ala Ala Lys Lys Trp Gln Val Thr
                165                 170                 175

Ala Ile Asn Val Gly Asn Ile Asn Asn Asp Lys Lys Asp Glu Met Tyr
            180                 185                 190

Arg Ser Leu Phe Gln Asp Leu Glu Leu Lys Lys Glu Arg Arg Val Ile
        195                 200                 205

Leu Asp Cys Glu Arg Asp Lys Val Asn Asp Ile Val Asp Gln Val Ile
210                 215                 220

Thr Ile Gly Lys His Val Lys Gly Tyr His Tyr Ile Ile Ala Asn Leu
225                 230                 235                 240

Gly Phe Thr Asp Gly Asp Leu Leu Lys Ile Gln Phe Gly Gly Ala Asn
                245                 250                 255

Val Ser Gly Phe Gln Ile Val Asp Tyr Asp Asp Ser Leu Val Ser Lys
            260                 265                 270

Phe Ile Glu Arg Trp Ser Thr Leu Glu Glu Lys Glu Tyr Pro Gly Ala
        275                 280                 285

His Thr Thr Thr Ile Lys Tyr Thr Ser Ala Leu Thr Tyr Asp Ala Val
290                 295                 300

Gln Val Met Thr Glu Ala Phe Arg Asn Leu Arg Lys Gln Arg Ile Glu
305                 310                 315                 320

Ile Ser Arg Arg Gly Asn Ala Gly Asp Cys Leu Ala Asn Pro Ala Val
                325                 330                 335
```

-continued

| | | | | | | | | | | | | | |
|---|---|---|---|---|---|---|---|---|---|---|---|---|---|
|Pro|Trp|Gly|Gln 340|Gly|Val|Glu|Ile|Glu 345|Arg|Ala|Leu|Lys|Gln 350|Val|Gln|
|Val|Glu|Gly 355|Leu|Ser|Gly|Asn 360|Ile|Lys|Phe|Asp|Gln 365|Asn|Gly|Lys|Arg|
|Ile|Asn 370|Tyr|Thr|Ile|Asn 375|Ile|Met|Glu|Leu|Lys 380|Thr|Asn|Gly|Pro|Arg|
|Lys 385|Ile|Gly|Tyr|Trp|Ser 390|Glu|Val|Asp|Lys|Met 395|Val|Val|Thr|Leu|Thr 400|
|Glu|Leu|Pro|Ser|Gly 405|Asn|Asp|Thr|Ser|Gly 410|Leu|Glu|Asn|Lys|Thr 415|Val|
|Val|Val|Thr|Thr 420|Ile|Leu|Glu|Ser|Pro 425|Tyr|Val|Met|Met|Lys 430|Lys|Asn|
|His|Glu|Met 435|Leu|Glu|Gly|Asn 440|Glu|Arg|Tyr|Glu|Gly 445|Tyr|Cys|Val|Asp|
|Leu|Ala 450|Ala|Glu|Ile|Ala 455|Lys|His|Cys|Gly|Phe 460|Lys|Tyr|Lys|Leu|Thr|
|Ile 465|Val|Gly|Asp|Gly|Lys 470|Tyr|Gly|Ala|Arg|Asp 475|Ala|Asp|Thr|Lys|Ile 480|
|Trp|Asn|Gly|Met|Val 485|Gly|Glu|Leu|Val|Tyr 490|Gly|Lys|Ala|Asp|Ile 495|Ala|
|Ile|Ala|Pro|Leu 500|Thr|Ile|Thr|Leu|Val 505|Arg|Glu|Glu|Val|Ile 510|Asp|Phe|
|Ser|Lys|Pro 515|Phe|Met|Ser|Leu|Gly 520|Ile|Ser|Ile|Met|Ile 525|Lys|Lys|Pro|
|Gln|Lys 530|Ser|Lys|Pro|Gly|Val 535|Phe|Ser|Phe|Leu|Asp 540|Pro|Leu|Ala|Tyr|
|Glu 545|Ile|Trp|Met|Cys|Ile 550|Val|Phe|Ala|Tyr|Ile 555|Gly|Val|Ser|Val|Val 560|
|Leu|Phe|Leu|Val|Ser 565|Arg|Phe|Ser|Pro|Tyr 570|Glu|Trp|His|Thr|Glu 575|Glu|
|Phe|Glu|Asp|Gly 580|Arg|Glu|Thr|Gln|Ser 585|Ser|Glu|Ser|Thr|Asn 590|Glu|Phe|
|Gly|Ile|Phe 595|Asn|Ser|Leu|Trp|Phe 600|Ser|Leu|Gly|Ala|Phe 605|Met|Arg|Gln|
|Gly|Cys 610|Asp|Ile|Ser|Pro|Arg 615|Ser|Leu|Ser|Gly|Arg 620|Ile|Val|Gly|Gly|
|Val 625|Trp|Trp|Phe|Phe|Thr 630|Leu|Ile|Ile|Ile|Ser 635|Ser|Tyr|Thr|Ala|Asn 640|
|Leu|Ala|Ala|Phe|Leu 645|Thr|Val|Glu|Arg|Met 650|Val|Ser|Pro|Ile|Glu 655|Ser|
|Ala|Glu|Asp|Leu 660|Ser|Lys|Gln|Thr|Glu 665|Ile|Ala|Tyr|Gly|Thr 670|Leu|Asp|
|Ser|Gly|Ser 675|Thr|Lys|Glu|Phe|Phe 680|Arg|Arg|Ser|Lys|Ile 685|Ala|Val|Phe|
|Asp|Lys|Met 690|Trp|Thr|Tyr|Met|Arg 695|Ser|Ala|Glu|Pro|Ser 700|Val|Phe|Val|
|Arg 705|Thr|Thr|Ala|Glu|Gly 710|Val|Ala|Arg|Val|Arg 715|Lys|Ser|Lys|Gly|Lys 720|
|Tyr|Ala|Tyr|Leu|Leu 725|Glu|Ser|Thr|Met|Asn 730|Glu|Tyr|Ile|Glu|Gln 735|Arg|
|Lys|Pro|Cys|Asp 740|Thr|Met|Lys|Val|Gly 745|Gly|Asn|Leu|Asp|Ser 750|Lys|Gly|
|Tyr|Gly|Ile 755|Ala|Thr|Pro|Lys|Gly 760|Ser|Ser|Leu|Gly|Thr 765|Pro|Val|Asn|

```
Leu  Ala  Val  Leu  Lys  Leu  Ser  Glu  Gln  Gly  Val  Leu  Asp  Lys  Leu  Lys
     770            775                      780
Asn  Lys  Trp  Trp  Tyr  Asp  Lys  Gly  Glu  Cys  Gly  Ala  Lys  Asp  Ser  Gly
785            790                      795                           800
Ser  Lys  Glu  Lys  Thr  Ser  Ala  Leu  Ser  Leu  Ser  Asn  Val  Ala  Gly  Val
               805                      810                      815
Phe  Tyr  Ile  Leu  Val  Gly  Gly  Leu  Gly  Leu  Ala  Met  Leu  Val  Ala  Leu
               820                 825                      830
Ile  Glu  Phe  Cys  Tyr  Lys  Ser  Arg  Ala  Glu  Ala  Lys  Arg  Met  Lys  Val
          835                      840                 845
Ala  Lys  Asn  Ala  Gln  Asn  Ile  Asn  Pro  Ser  Ser  Ser  Gln  Asn  Ser  Gln
     850                      855                      860
Asn  Phe  Ala  Thr  Tyr  Lys  Glu  Gly  Tyr  Asn  Val  Tyr  Gly  Ile  Glu  Ser
865                 870                      875                           880
Val  Lys  Ile
```

( 2 ) INFORMATION FOR SEQ ID NO: 7:

( i ) SEQUENCE CHARACTERISTICS:
        ( A ) LENGTH: 2955 base pairs
        ( B ) TYPE: nucleic acid
        ( C ) STRANDEDNESS: single
        ( D ) TOPOLOGY: linear ( i i ) MOLECULE TYPE: cDNA to mRNA ( v i ) ORIGINAL SOURCE:
        ( A ) ORGANISM: Homo sapiens
        ( B ) DEVELOPMENTAL STAGE: Adult
        ( C ) TISSUE TYPE: Brain ( i x ) FEATURE:
        ( A ) NAME/KEY: CDS
        ( B ) LOCATION: 28..2676

( x i ) SEQUENCE DESCRIPTION: SEQ ID NO: 7:

```
TTTGTCGACG  CTCTACTTTT  CTTGGAA ATG  CAA  AAG  ATT  ATG  CAT  GTT  TCT          51
                                Met  Gln  Lys  Ile  Met  His  Val  Ser
                                  1                    5

GTC  CTC  CTT  TCT  CCT  GTT  TTA  TGG  GGA  CTG  ATT  TTT  GGT  GTC  TCT  TCT   99
Val  Leu  Leu  Ser  Pro  Val  Leu  Trp  Gly  Leu  Ile  Phe  Gly  Val  Ser  Ser
          10                      15                      20

AAC  AGC  ATA  CAG  ATA  GGG  GGG  CTA  TTT  CCT  AGG  GGC  GCC  GAT  CAA  GAA  147
Asn  Ser  Ile  Gln  Ile  Gly  Gly  Leu  Phe  Pro  Arg  Gly  Ala  Asp  Gln  Glu
 25                      30                      35                        40

TAC  AGT  GCA  TTT  CGA  GTA  GGG  ATG  GTT  CAG  TTT  TCC  ACT  TCG  GAG  TTC  195
Tyr  Ser  Ala  Phe  Arg  Val  Gly  Met  Val  Gln  Phe  Ser  Thr  Ser  Glu  Phe
                    45                      50                      55

AGA  CTG  ACA  CCC  CAC  ATC  GAC  AAT  TTG  GAG  GTG  GCA  AAC  AGC  TTC  GCA  243
Arg  Leu  Thr  Pro  His  Ile  Asp  Asn  Leu  Glu  Val  Ala  Asn  Ser  Phe  Ala
               60                      65                      70

GTC  ACT  AAT  GCT  TTC  TGC  TCC  CAG  TTT  TCG  AGA  GGA  GTC  TAT  GCT  ATT  291
Val  Thr  Asn  Ala  Phe  Cys  Ser  Gln  Phe  Ser  Arg  Gly  Val  Tyr  Ala  Ile
          75                      80                      85

TTT  GGA  TTT  TAT  GAC  AAG  AAG  TCT  GTA  AAT  ACC  ATC  ACA  TCA  TTT  TGC  339
Phe  Gly  Phe  Tyr  Asp  Lys  Lys  Ser  Val  Asn  Thr  Ile  Thr  Ser  Phe  Cys
     90                      95                     100

GGA  ACA  CTC  CAC  GTC  TCC  TTC  ATC  ACT  CCC  AGC  TTC  CCA  ACA  GAT  GGC  387
Gly  Thr  Leu  His  Val  Ser  Phe  Ile  Thr  Pro  Ser  Phe  Pro  Thr  Asp  Gly
105                     110                     115                       120

ACA  CAT  CCA  TTT  GTC  ATT  CAG  ATG  AGA  CCC  GAC  CTC  AAA  GGA  GCT  CTC  435
Thr  His  Pro  Phe  Val  Ile  Gln  Met  Arg  Pro  Asp  Leu  Lys  Gly  Ala  Leu
```

|  |  |  |  |  | 125 |  |  |  |  | 130 |  |  |  |  | 135 |  |  |  |
|---|---|---|---|---|---|---|---|---|---|---|---|---|---|---|---|---|---|---|

| CTT | AGC | TTG | ATT | GAA | TAC | TAT | CAA | TGG | GAC | AAG | TTT | GCA | TAC | CTC | TAT | 483 |
|---|---|---|---|---|---|---|---|---|---|---|---|---|---|---|---|---|
| Leu | Ser | Leu | Ile | Glu | Tyr | Tyr | Gln | Trp | Asp | Lys | Phe | Ala | Tyr | Leu | Tyr | |
| | | | 140 | | | | 145 | | | | | | 150 | | | |

| GAC | AGT | GAC | AGA | GGC | TTA | TCA | ACA | CTG | CAA | GCT | GTG | CTG | GAT | TCT | GCT | 531 |
|---|---|---|---|---|---|---|---|---|---|---|---|---|---|---|---|---|
| Asp | Ser | Asp | Arg | Gly | Leu | Ser | Thr | Leu | Gln | Ala | Val | Leu | Asp | Ser | Ala | |
| | | 155 | | | | 160 | | | | | 165 | | | | | |

| GCT | GAA | AAG | AAA | TGG | CAA | GTG | ACT | GCT | ATC | AAT | GTG | GGA | AAC | ATT | AAC | 579 |
|---|---|---|---|---|---|---|---|---|---|---|---|---|---|---|---|---|
| Ala | Glu | Lys | Lys | Trp | Gln | Val | Thr | Ala | Ile | Asn | Val | Gly | Asn | Ile | Asn | |
| | 170 | | | | 175 | | | | | 180 | | | | | | |

| AAT | GAC | AAG | AAA | GAT | GAG | ATG | TAC | CGA | TCA | CTT | TTT | CAA | GAT | CTG | GAG | 627 |
|---|---|---|---|---|---|---|---|---|---|---|---|---|---|---|---|---|
| Asn | Asp | Lys | Lys | Asp | Glu | Met | Tyr | Arg | Ser | Leu | Phe | Gln | Asp | Leu | Glu | |
| 185 | | | | | 190 | | | | | 195 | | | | | 200 | |

| TTA | AAA | AAG | GAA | CGG | CGT | GTA | ATT | CTG | GAC | TGT | GAA | AGG | GAT | AAA | GTA | 675 |
|---|---|---|---|---|---|---|---|---|---|---|---|---|---|---|---|---|
| Leu | Lys | Lys | Glu | Arg | Arg | Val | Ile | Leu | Asp | Cys | Glu | Arg | Asp | Lys | Val | |
| | | | | 205 | | | | | 210 | | | | | 215 | | |

| AAC | GAC | ATT | GTA | GAC | CAG | GTT | ATT | ACC | ATT | GGA | AAA | CAC | GTT | AAA | GGG | 723 |
|---|---|---|---|---|---|---|---|---|---|---|---|---|---|---|---|---|
| Asn | Asp | Ile | Val | Asp | Gln | Val | Ile | Thr | Ile | Gly | Lys | His | Val | Lys | Gly | |
| | | | 220 | | | | | 225 | | | | | 230 | | | |

| TAC | CAC | TAC | ATC | ATT | GCA | AAT | CTG | GGA | TTT | ACT | GAT | GGA | GAC | CTA | TTA | 771 |
|---|---|---|---|---|---|---|---|---|---|---|---|---|---|---|---|---|
| Tyr | His | Tyr | Ile | Ile | Ala | Asn | Leu | Gly | Phe | Thr | Asp | Gly | Asp | Leu | Leu | |
| | | 235 | | | | | 240 | | | | | 245 | | | | |

| AAA | ATC | CAG | TTT | GGA | GGT | GCA | AAT | GTC | TCT | GGA | TTT | CAG | ATA | GTG | GAC | 819 |
|---|---|---|---|---|---|---|---|---|---|---|---|---|---|---|---|---|
| Lys | Ile | Gln | Phe | Gly | Gly | Ala | Asn | Val | Ser | Gly | Phe | Gln | Ile | Val | Asp | |
| | 250 | | | | | 255 | | | | | 260 | | | | | |

| TAT | GAT | GAT | TCG | TTG | GTA | TCT | AAA | TTT | ATA | GAA | AGA | TGG | TCA | ACA | CTG | 867 |
|---|---|---|---|---|---|---|---|---|---|---|---|---|---|---|---|---|
| Tyr | Asp | Asp | Ser | Leu | Val | Ser | Lys | Phe | Ile | Glu | Arg | Trp | Ser | Thr | Leu | |
| 265 | | | | | 270 | | | | | 275 | | | | | 280 | |

| GAA | GAA | AAA | GAA | TAC | CCT | GGA | GCT | CAC | ACA | ACA | ACA | ATT | AAG | TAT | ACT | 915 |
|---|---|---|---|---|---|---|---|---|---|---|---|---|---|---|---|---|
| Glu | Glu | Lys | Glu | Tyr | Pro | Gly | Ala | His | Thr | Thr | Thr | Ile | Lys | Tyr | Thr | |
| | | | | 285 | | | | | 290 | | | | | 295 | | |

| TCT | GCT | CTG | ACC | TAT | GAT | GCC | GTT | CAA | GTG | ATG | ACT | GAA | GCC | TTC | CGC | 963 |
|---|---|---|---|---|---|---|---|---|---|---|---|---|---|---|---|---|
| Ser | Ala | Leu | Thr | Tyr | Asp | Ala | Val | Gln | Val | Met | Thr | Glu | Ala | Phe | Arg | |
| | | | 300 | | | | | 305 | | | | | 310 | | | |

| AAC | CTA | AGG | AAG | CAA | AGA | ATT | GAA | ATC | TCC | CGA | AGG | GGG | AAT | GCA | GGA | 1011 |
|---|---|---|---|---|---|---|---|---|---|---|---|---|---|---|---|---|
| Asn | Leu | Arg | Lys | Gln | Arg | Ile | Glu | Ile | Ser | Arg | Arg | Gly | Asn | Ala | Gly | |
| | | 315 | | | | | 320 | | | | | 325 | | | | |

| GAC | TGT | CTG | GCA | AAC | CCA | GCA | GTG | CCC | TGG | GGA | CAA | GGT | GTA | GAA | ATA | 1059 |
|---|---|---|---|---|---|---|---|---|---|---|---|---|---|---|---|---|
| Asp | Cys | Leu | Ala | Asn | Pro | Ala | Val | Pro | Trp | Gly | Gln | Gly | Val | Glu | Ile | |
| | 330 | | | | | 335 | | | | | 340 | | | | | |

| GAA | AGG | GCC | CTC | AAA | CAG | GTT | CAG | GTT | GAA | GGT | CTC | TCA | GGA | AAT | ATA | 1107 |
|---|---|---|---|---|---|---|---|---|---|---|---|---|---|---|---|---|
| Glu | Arg | Ala | Leu | Lys | Gln | Val | Gln | Val | Glu | Gly | Leu | Ser | Gly | Asn | Ile | |
| 345 | | | | | 350 | | | | | 355 | | | | | 360 | |

| AAG | TTT | GAC | CAG | AAT | GGA | AAA | AGA | ATA | AAC | TAT | ACA | ATT | AAC | ATC | ATG | 1155 |
|---|---|---|---|---|---|---|---|---|---|---|---|---|---|---|---|---|
| Lys | Phe | Asp | Gln | Asn | Gly | Lys | Arg | Ile | Asn | Tyr | Thr | Ile | Asn | Ile | Met | |
| | | | | 365 | | | | | 370 | | | | | 375 | | |

| GAG | CTC | AAA | ACT | AAT | GGG | CCC | CGG | AAG | ATT | GGC | TAC | TGG | AGT | GAA | GTG | 1203 |
|---|---|---|---|---|---|---|---|---|---|---|---|---|---|---|---|---|
| Glu | Leu | Lys | Thr | Asn | Gly | Pro | Arg | Lys | Ile | Gly | Tyr | Trp | Ser | Glu | Val | |
| | | | 380 | | | | | 385 | | | | | 390 | | | |

| GAC | AAA | ATG | GTT | GTT | ACC | CTT | ACT | GAG | CTC | CCT | TCT | GGA | AAT | GAC | ACC | 1251 |
|---|---|---|---|---|---|---|---|---|---|---|---|---|---|---|---|---|
| Asp | Lys | Met | Val | Val | Thr | Leu | Thr | Glu | Leu | Pro | Ser | Gly | Asn | Asp | Thr | |
| | | 395 | | | | | 400 | | | | | 405 | | | | |

| TCT | GGG | CTT | GAG | AAT | AAG | ACT | GTT | GTT | GTC | ACC | ACA | ATT | TTG | GAA | TCT | 1299 |
|---|---|---|---|---|---|---|---|---|---|---|---|---|---|---|---|---|
| Ser | Gly | Leu | Glu | Asn | Lys | Thr | Val | Val | Val | Thr | Thr | Ile | Leu | Glu | Ser | |
| | 410 | | | | | 415 | | | | | 420 | | | | | |

| CCG | TAT | GTT | ATG | ATG | AAG | AAA | AAT | CAT | GAA | ATG | CTT | GAA | GGC | AAT | GAG | 1347 |
|---|---|---|---|---|---|---|---|---|---|---|---|---|---|---|---|---|
| Pro | Tyr | Val | Met | Met | Lys | Lys | Asn | His | Glu | Met | Leu | Glu | Gly | Asn | Glu | |
| 425 | | | | | 430 | | | | | 435 | | | | | 440 | |

| CGC | TAT | GAG | GGC | TAC | TGT | GTT | GAC | CTG | GCT | GCA | GAA | ATC | GCC | AAA | CAT | 1395 |
|---|---|---|---|---|---|---|---|---|---|---|---|---|---|---|---|---|
| Arg | Tyr | Glu | Gly | Tyr | Cys | Val | Asp | Leu | Ala | Ala | Glu | Ile | Ala | Lys | His | |

|     |     |     |     |     |     |     |     |     |     |     |     |     |     |     |     |      |
|-----|-----|-----|-----|-----|-----|-----|-----|-----|-----|-----|-----|-----|-----|-----|-----|------|
|     |     |     |     | 445 |     |     |     | 450 |     |     |     |     |     | 455 |     |      |
| TGT | GGG | TTC | AAG | TAC | AAG | TTG | ACA | ATT | GTT | GGT | GAT | GGC | AAG | TAT | GGG | 1443 |
| Cys | Gly | Phe | Lys 460 | Tyr | Lys | Leu | Thr | Ile 465 | Val | Gly | Asp | Gly | Lys 470 | Tyr | Gly |      |
| GCC | AGG | GAT | GCA | GAC | ACG | AAA | ATT | TGG | AAT | GGG | ATG | GTT | GGA | GAA | CTT | 1491 |
| Ala | Arg | Asp | Ala | Asp 475 | Thr | Lys | Ile | Trp 480 | Asn | Gly | Met | Val 485 | Gly | Glu | Leu |      |
| GTA | TAT | GGG | AAA | GCT | GAT | ATT | GCA | ATT | GCT | CCA | TTA | ACT | ATT | ACC | CTT | 1539 |
| Val | Tyr 490 | Gly | Lys | Ala | Asp | Ile 495 | Ala | Ile | Ala | Pro | Leu 500 | Thr | Ile | Thr | Leu |      |
| GTG | AGA | GAA | GAG | GTG | ATT | GAC | TTC | TCA | AAG | CCC | TTC | ATG | AGC | CTC | GGG | 1587 |
| Val 505 | Arg | Glu | Glu | Val | Ile 510 | Asp | Phe | Ser | Lys | Pro 515 | Phe | Met | Ser | Leu | Gly 520 |      |
| ATA | TCT | ATC | ATG | ATC | AAG | AAG | CCT | CAG | AAG | TCC | AAA | CCA | GGA | GTG | TTT | 1635 |
| Ile | Ser | Ile | Met | Ile 525 | Lys | Lys | Pro | Gln | Lys 530 | Ser | Lys | Pro | Gly | Val 535 | Phe |      |
| TCC | TTT | CTT | GAT | CCT | TTA | GCC | TAT | GAG | ATC | TGG | ATG | TGC | ATT | GTT | TTT | 1683 |
| Ser | Phe | Leu | Asp 540 | Pro | Leu | Ala | Tyr | Glu 545 | Ile | Trp | Met | Cys | Ile 550 | Val | Phe |      |
| GCC | TAC | ATT | GGG | GTC | AGT | GTA | GTT | TTA | TTC | CTG | GTC | AGC | AGA | TTT | AGC | 1731 |
| Ala | Tyr | Ile 555 | Gly | Val | Ser | Val | Val 560 | Leu | Phe | Leu | Val | Ser 565 | Arg | Phe | Ser |      |
| CCC | TAC | GAG | TGG | CAC | ACT | GAG | GAG | TTT | GAA | GAT | GGA | AGA | GAA | ACA | CAA | 1779 |
| Pro | Tyr 570 | Glu | Trp | His | Thr | Glu 575 | Glu | Phe | Glu | Asp | Gly 580 | Arg | Glu | Thr | Gln |      |
| AGT | AGT | GAA | TCA | ACT | AAT | GAA | TTT | GGG | ATT | TTT | AAT | AGT | CTC | TGG | TTT | 1827 |
| Ser 585 | Ser | Glu | Ser | Thr | Asn 590 | Glu | Phe | Gly | Ile | Phe 595 | Asn | Ser | Leu | Trp | Phe 600 |      |
| TCC | TTG | GGT | GCC | TTT | ATG | CGG | CAA | GGA | TGC | GAT | ATT | TCG | CCA | AGA | TCC | 1875 |
| Ser | Leu | Gly | Ala | Phe 605 | Met | Arg | Gln | Gly | Cys 610 | Asp | Ile | Ser | Pro | Arg 615 | Ser |      |
| CTC | TCT | GGG | CGC | ATT | GTT | GGA | GGT | GTG | TGG | TGG | TTC | TTT | ACC | CTG | ATC | 1923 |
| Leu | Ser | Gly | Arg 620 | Ile | Val | Gly | Gly | Val 625 | Trp | Trp | Phe | Phe | Thr 630 | Leu | Ile |      |
| ATA | ATC | TCC | TCC | TAC | ACG | GCT | AAC | TTA | GCT | GCC | TTC | CTG | ACT | GTA | GAG | 1971 |
| Ile | Ile | Ser 635 | Ser | Tyr | Thr | Ala | Asn 640 | Leu | Ala | Ala | Phe | Leu 645 | Thr | Val | Glu |      |
| AGG | ATG | GTG | TCT | CCC | ATC | GAA | AGT | GCT | GAG | GAT | CTT | TCT | AAG | CAA | ACA | 2019 |
| Arg | Met | Val 650 | Ser | Pro | Ile | Glu | Ser 655 | Ala | Glu | Asp | Leu | Ser 660 | Lys | Gln | Thr |      |
| GAA | ATT | GCT | TAT | GGA | ACA | TTA | GAC | TCT | GGC | TCC | ACT | AAA | GAG | TTT | TTC | 2067 |
| Glu | Ile | Ala | Tyr | Gly 665 | Thr | Leu | Asp | Ser | Gly 670 | Ser | Thr | Lys | Glu | Phe 675 | Phe 680 |      |
| AGG | AGA | TCT | AAA | ATT | GCA | GTG | TTT | GAT | AAA | ATG | TGG | ACC | TAC | ATG | CGG | 2115 |
| Arg | Arg | Ser | Lys | Ile 685 | Ala | Val | Phe | Asp | Lys 690 | Met | Trp | Thr | Tyr | Met 695 | Arg |      |
| AGT | GCG | GAG | CCC | TCT | GTG | TTT | GTG | AGG | ACT | ACG | GCC | GAA | GGG | GTG | GCT | 2163 |
| Ser | Ala | Glu | Pro 700 | Ser | Val | Phe | Val | Arg 705 | Thr | Thr | Ala | Glu | Gly 710 | Val | Ala |      |
| AGA | GTG | CGG | AAG | TCC | AAA | GGG | AAA | TAT | GCC | TAC | TTG | TTG | GAG | TCC | ACG | 2211 |
| Arg | Val | Arg 715 | Lys | Ser | Lys | Gly | Lys 720 | Tyr | Ala | Tyr | Leu | Leu 725 | Glu | Ser | Thr |      |
| ATG | AAC | GAG | TAC | ATT | GAG | CAA | AGG | AAG | CCT | TGC | GAC | ACC | ATG | AAA | GTT | 2259 |
| Met | Asn | Glu 730 | Tyr | Ile | Glu | Gln | Arg 735 | Lys | Pro | Cys | Asp | Thr 740 | Met | Lys | Val |      |
| GGT | GGA | AAC | CTG | GAT | TCC | AAA | GGC | TAT | GGC | ATC | GCA | ACA | CCT | AAA | GGA | 2307 |
| Gly | Gly 745 | Asn | Leu | Asp | Ser | Lys 750 | Gly | Tyr | Gly | Ile | Ala 755 | Thr | Pro | Lys | Gly 760 |      |
| TCC | TCA | TTA | AGA | AAT | GCG | GTT | AAC | CTC | GCA | GTA | CTA | AAA | CTG | AAT | GAA | 2355 |
| Ser | Ser | Leu | Arg | Asn | Ala | Val | Asn | Leu | Ala | Val | Leu | Lys | Leu | Asn | Glu |      |

-continued

|  |  |  | 765 |  |  |  | 770 |  |  |  | 775 |  |  |  |  |
|---|---|---|---|---|---|---|---|---|---|---|---|---|---|---|---|
| CAA | GGC | CTG | TTG | GAC | AAA | TTG | AAA | AAC | AAA | TGG | TGG | TAC | GAC | AAA | GGA | 2403
| Gln | Gly | Leu | Leu | Asp | Lys | Leu | Lys | Asn | Lys | Trp | Trp | Tyr | Asp | Lys | Gly |
|  |  |  | 780 |  |  |  | 785 |  |  |  |  | 790 |  |  |  |
| GAG | TGC | GGC | AGC | GGG | GGA | GGT | GAT | TCC | AAG | GAA | AAG | ACC | AGT | GCC | CTC | 2451
| Glu | Cys | Gly | Ser | Gly | Gly | Gly | Asp | Ser | Lys | Glu | Lys | Thr | Ser | Ala | Leu |
|  |  | 795 |  |  |  |  | 800 |  |  |  |  | 805 |  |  |  |
| AGT | CTG | AGC | AAC | GTT | GCT | GGA | GTA | TTC | TAC | ATC | CTT | GTC | GGG | GGC | CTT | 2499
| Ser | Leu | Ser | Asn | Val | Ala | Gly | Val | Phe | Tyr | Ile | Leu | Val | Gly | Gly | Leu |
|  | 810 |  |  |  |  |  | 815 |  |  |  |  | 820 |  |  |  |
| GGT | TTG | GCA | ATG | CTG | GTG | GCT | TTG | ATT | GAG | TTC | TGT | TAC | AAG | TCA | AGG | 2547
| Gly | Leu | Ala | Met | Leu | Val | Ala | Leu | Ile | Glu | Phe | Cys | Tyr | Lys | Ser | Arg |
| 825 |  |  |  |  | 830 |  |  |  |  | 835 |  |  |  |  | 840 |
| GCC | GAG | GCG | AAA | CGA | ATG | AAG | GTG | GCA | AAG | AAT | GCA | CAG | AAT | ATT | AAC | 2595
| Ala | Glu | Ala | Lys | Arg | Met | Lys | Val | Ala | Lys | Asn | Ala | Gln | Asn | Ile | Asn |
|  |  |  |  | 845 |  |  |  |  | 850 |  |  |  |  | 855 |  |
| CCA | TCT | TCC | TCG | CAG | AAT | TCA | CAG | AAT | TTT | GCA | ACT | TAT | AAG | GAA | GGT | 2643
| Pro | Ser | Ser | Ser | Gln | Asn | Ser | Gln | Asn | Phe | Ala | Thr | Tyr | Lys | Glu | Gly |
|  |  |  | 860 |  |  |  |  | 865 |  |  |  |  | 870 |  |  |
| TAC | AAC | GTA | TAT | GGC | ATC | GAA | AGT | GTT | AAA | ATT | TAGGGGATGA | | | CCTTGAAATG | | 2696
| Tyr | Asn | Val | Tyr | Gly | Ile | Glu | Ser | Val | Lys | Ile |  |  |  |  |  |
|  |  | 875 |  |  |  |  | 880 |  |  |  |  |  |  |  |  |
| ATGCCATGAG | GAACAAGGCA | AGGCTGTCAA | TTACAGGAAG | TACTGGAGAA | AATGGACGTG | | | | | | | | | | | 2756
| TTATGACTCC | AGAATTTCCC | AAAGCAGTGC | ATGCTGTCCC | TTACGTGAGT | CCTGGCATGG | | | | | | | | | | | 2816
| GAATGAATGT | CAGTGTGACT | GATCTCTCGT | GATTGATAAG | AACCTTTTGA | GTGCCTTACA | | | | | | | | | | | 2876
| CAATGGTTTT | CTTGTGTTTA | TTGTCAAAGT | GGTGAGAGGC | ATCCAGTATC | TTGAAGACTT | | | | | | | | | | | 2936
| TTCTTTCAGC | CAAGAATTC | | | | | | | | | | | | | | | 2955

(2) INFORMATION FOR SEQ ID NO:8:

(i) SEQUENCE CHARACTERISTICS:
    (A) LENGTH: 883 amino acids
    (B) TYPE: amino acid
    (D) TOPOLOGY: linear (ii) MOLECULE TYPE: protein (xi) SEQUENCE DESCRIPTION: SEQ ID NO: 8:

| Met | Gln | Lys | Ile | Met | His | Val | Ser | Val | Leu | Leu | Ser | Pro | Val | Leu | Trp |
|---|---|---|---|---|---|---|---|---|---|---|---|---|---|---|---|
| 1 |  |  |  | 5 |  |  |  |  | 10 |  |  |  |  | 15 |  |

| Gly | Leu | Ile | Phe | Gly | Val | Ser | Ser | Asn | Ser | Ile | Gln | Ile | Gly | Gly | Leu |
|---|---|---|---|---|---|---|---|---|---|---|---|---|---|---|---|
|  |  |  | 20 |  |  |  |  | 25 |  |  |  |  | 30 |  |  |

| Phe | Pro | Arg | Gly | Ala | Asp | Gln | Glu | Tyr | Ser | Ala | Phe | Arg | Val | Gly | Met |
|---|---|---|---|---|---|---|---|---|---|---|---|---|---|---|---|
|  |  | 35 |  |  |  |  | 40 |  |  |  |  | 45 |  |  |  |

| Val | Gln | Phe | Ser | Thr | Ser | Glu | Phe | Arg | Leu | Thr | Pro | His | Ile | Asp | Asn |
|---|---|---|---|---|---|---|---|---|---|---|---|---|---|---|---|
|  | 50 |  |  |  |  | 55 |  |  |  |  | 60 |  |  |  |  |

| Leu | Glu | Val | Ala | Asn | Ser | Phe | Ala | Val | Thr | Asn | Ala | Phe | Cys | Ser | Gln |
|---|---|---|---|---|---|---|---|---|---|---|---|---|---|---|---|
| 65 |  |  |  |  | 70 |  |  |  |  | 75 |  |  |  |  | 80 |

| Phe | Ser | Arg | Gly | Val | Tyr | Ala | Ile | Phe | Gly | Phe | Tyr | Asp | Lys | Lys | Ser |
|---|---|---|---|---|---|---|---|---|---|---|---|---|---|---|---|
|  |  |  |  | 85 |  |  |  |  | 90 |  |  |  |  | 95 |  |

| Val | Asn | Thr | Ile | Thr | Ser | Phe | Cys | Gly | Thr | Leu | His | Val | Ser | Phe | Ile |
|---|---|---|---|---|---|---|---|---|---|---|---|---|---|---|---|
|  |  |  | 100 |  |  |  |  | 105 |  |  |  |  | 110 |  |  |

| Thr | Pro | Ser | Phe | Pro | Thr | Asp | Gly | Thr | His | Pro | Phe | Val | Ile | Gln | Met |
|---|---|---|---|---|---|---|---|---|---|---|---|---|---|---|---|
|  |  | 115 |  |  |  |  | 120 |  |  |  |  | 125 |  |  |  |

| Arg | Pro | Asp | Leu | Lys | Gly | Ala | Leu | Leu | Ser | Leu | Ile | Glu | Tyr | Tyr | Gln |
|---|---|---|---|---|---|---|---|---|---|---|---|---|---|---|---|
|  | 130 |  |  |  |  | 135 |  |  |  |  | 140 |  |  |  |  |

| Trp | Asp | Lys | Phe | Ala | Tyr | Leu | Tyr | Asp | Ser | Asp | Arg | Gly | Leu | Ser | Thr |
|---|---|---|---|---|---|---|---|---|---|---|---|---|---|---|---|

-continued

| 145 | | | | | 150 | | | | | 155 | | | | | 160 |
|---|---|---|---|---|---|---|---|---|---|---|---|---|---|---|---|
| Leu | Gln | Ala | Val | Leu 165 | Asp | Ser | Ala | Ala | Glu 170 | Lys | Lys | Trp | Gln | Val 175 | Thr |
| Ala | Ile | Asn | Val 180 | Gly | Asn | Ile | Asn 185 | Asn | Asp | Lys | Lys | Asp 190 | Glu | Met | Tyr |
| Arg | Ser | Leu 195 | Phe | Gln | Asp | Leu 200 | Glu | Leu | Lys | Lys | Glu 205 | Arg | Arg | Val | Ile |
| Leu | Asp 210 | Cys | Glu | Arg | Asp 215 | Lys | Val | Asn | Asp | Ile 220 | Val | Asp | Gln | Val | Ile |
| Thr 225 | Ile | Gly | Lys | His | Val 230 | Lys | Gly | Tyr | His | Tyr 235 | Ile | Ile | Ala | Asn | Leu 240 |
| Gly | Phe | Thr | Asp | Gly 245 | Asp | Leu | Leu | Lys | Ile 250 | Gln | Phe | Gly | Gly | Ala 255 | Asn |
| Val | Ser | Gly | Phe 260 | Gln | Ile | Val | Asp | Tyr 265 | Asp | Asp | Ser | Leu | Val 270 | Ser | Lys |
| Phe | Ile | Glu 275 | Arg | Trp | Ser | Thr | Leu 280 | Glu | Glu | Lys | Glu | Tyr 285 | Pro | Gly | Ala |
| His | Thr 290 | Thr | Thr | Ile | Lys | Tyr 295 | Thr | Ser | Ala | Leu | Thr 300 | Tyr | Asp | Ala | Val |
| Gln 305 | Val | Met | Thr | Glu | Ala 310 | Phe | Arg | Asn | Leu | Arg 315 | Lys | Gln | Arg | Ile | Glu 320 |
| Ile | Ser | Arg | Arg | Gly 325 | Asn | Ala | Gly | Asp | Cys 330 | Leu | Ala | Asn | Pro | Ala 335 | Val |
| Pro | Trp | Gly | Gln 340 | Gly | Val | Glu | Ile | Glu 345 | Arg | Ala | Leu | Lys | Gln 350 | Val | Gln |
| Val | Glu | Gly 355 | Leu | Ser | Gly | Asn | Ile 360 | Lys | Phe | Asp | Gln | Asn 365 | Gly | Lys | Arg |
| Ile | Asn 370 | Tyr | Thr | Ile | Asn | Ile 375 | Met | Glu | Leu | Lys | Thr 380 | Asn | Gly | Pro | Arg |
| Lys 385 | Ile | Gly | Tyr | Trp | Ser 390 | Glu | Val | Asp | Lys | Met 395 | Val | Val | Thr | Leu | Thr 400 |
| Glu | Leu | Pro | Ser | Gly 405 | Asn | Asp | Thr | Ser | Gly 410 | Leu | Glu | Asn | Lys | Thr 415 | Val |
| Val | Val | Thr | Thr 420 | Ile | Leu | Glu | Ser | Pro 425 | Tyr | Val | Met | Met | Lys 430 | Lys | Asn |
| His | Glu | Met 435 | Leu | Glu | Gly | Asn | Glu 440 | Arg | Tyr | Glu | Gly | Tyr 445 | Cys | Val | Asp |
| Leu | Ala 450 | Ala | Glu | Ile | Ala | Lys 455 | His | Cys | Gly | Phe | Lys 460 | Tyr | Lys | Leu | Thr |
| Ile 465 | Val | Gly | Asp | Gly | Lys 470 | Tyr | Gly | Ala | Arg | Asp 475 | Ala | Asp | Thr | Lys | Ile 480 |
| Trp | Asn | Gly | Met | Val 485 | Gly | Glu | Leu | Val | Tyr 490 | Gly | Lys | Ala | Asp | Ile 495 | Ala |
| Ile | Ala | Pro | Leu 500 | Thr | Ile | Thr | Leu | Val 505 | Arg | Glu | Glu | Val | Ile 510 | Asp | Phe |
| Ser | Lys | Pro 515 | Phe | Met | Ser | Leu | Gly 520 | Ile | Ser | Ile | Met | Ile 525 | Lys | Lys | Pro |
| Gln | Lys 530 | Ser | Lys | Pro | Gly | Val 535 | Phe | Ser | Phe | Leu | Asp 540 | Pro | Leu | Ala | Tyr |
| Glu 545 | Ile | Trp | Met | Cys | Ile 550 | Val | Phe | Ala | Tyr | Ile 555 | Gly | Val | Ser | Val | Val 560 |
| Leu | Phe | Leu | Val | Ser 565 | Arg | Phe | Ser | Pro | Tyr 570 | Glu | Trp | His | Thr | Glu 575 | Glu |

| | | | | | | | | | | | | | | |
|---|---|---|---|---|---|---|---|---|---|---|---|---|---|---|
| Phe | Glu | Asp | Gly | Arg | Glu | Thr | Gln | Ser | Ser | Glu | Ser | Thr | Asn | Glu | Phe |
| | | | 580 | | | | 585 | | | | | 590 | | |
| Gly | Ile | Phe | Asn | Ser | Leu | Trp | Phe | Ser | Leu | Gly | Ala | Phe | Met | Arg | Gln |
| | | 595 | | | | 600 | | | | | 605 | | | | |
| Gly | Cys | Asp | Ile | Ser | Pro | Arg | Ser | Leu | Ser | Gly | Arg | Ile | Val | Gly | Gly |
| | 610 | | | | 615 | | | | | 620 | | | | | |
| Val | Trp | Trp | Phe | Phe | Thr | Leu | Ile | Ile | Ile | Ser | Ser | Tyr | Thr | Ala | Asn |
| 625 | | | | | 630 | | | | | 635 | | | | | 640 |
| Leu | Ala | Ala | Phe | Leu | Thr | Val | Glu | Arg | Met | Val | Ser | Pro | Ile | Glu | Ser |
| | | | 645 | | | | | 650 | | | | | 655 | | |
| Ala | Glu | Asp | Leu | Ser | Lys | Gln | Thr | Glu | Ile | Ala | Tyr | Gly | Thr | Leu | Asp |
| | | | 660 | | | | 665 | | | | | 670 | | | |
| Ser | Gly | Ser | Thr | Lys | Glu | Phe | Phe | Arg | Arg | Ser | Lys | Ile | Ala | Val | Phe |
| | | 675 | | | | 680 | | | | | | 685 | | | |
| Asp | Lys | Met | Trp | Thr | Tyr | Met | Arg | Ser | Ala | Glu | Pro | Ser | Val | Phe | Val |
| | 690 | | | | | 695 | | | | | 700 | | | | |
| Arg | Thr | Thr | Ala | Glu | Gly | Val | Ala | Arg | Val | Arg | Lys | Ser | Lys | Gly | Lys |
| 705 | | | | | 710 | | | | | 715 | | | | | 720 |
| Tyr | Ala | Tyr | Leu | Leu | Glu | Ser | Thr | Met | Asn | Glu | Tyr | Ile | Glu | Gln | Arg |
| | | | | 725 | | | | | 730 | | | | | 735 | |
| Lys | Pro | Cys | Asp | Thr | Met | Lys | Val | Gly | Gly | Asn | Leu | Asp | Ser | Lys | Gly |
| | | | 740 | | | | | 745 | | | | | 750 | | |
| Tyr | Gly | Ile | Ala | Thr | Pro | Lys | Gly | Ser | Ser | Leu | Arg | Asn | Ala | Val | Asn |
| | | 755 | | | | | 760 | | | | | 765 | | | |
| Leu | Ala | Val | Leu | Lys | Leu | Asn | Glu | Gln | Gly | Leu | Leu | Asp | Lys | Leu | Lys |
| | 770 | | | | | 775 | | | | | 780 | | | | |
| Asn | Lys | Trp | Trp | Tyr | Asp | Lys | Gly | Glu | Cys | Gly | Ser | Gly | Gly | Gly | Asp |
| 785 | | | | | 790 | | | | | 795 | | | | | 800 |
| Ser | Lys | Glu | Lys | Thr | Ser | Ala | Leu | Ser | Leu | Ser | Asn | Val | Ala | Gly | Val |
| | | | | 805 | | | | | 810 | | | | | 815 | |
| Phe | Tyr | Ile | Leu | Val | Gly | Gly | Leu | Gly | Leu | Ala | Met | Leu | Val | Ala | Leu |
| | | | 820 | | | | | 825 | | | | | 830 | | |
| Ile | Glu | Phe | Cys | Tyr | Lys | Ser | Arg | Ala | Glu | Ala | Lys | Arg | Met | Lys | Val |
| | | 835 | | | | | 840 | | | | | 845 | | | |
| Ala | Lys | Asn | Ala | Gln | Asn | Ile | Asn | Pro | Ser | Ser | Ser | Gln | Asn | Ser | Gln |
| | 850 | | | | | 855 | | | | | 860 | | | | |
| Asn | Phe | Ala | Thr | Tyr | Lys | Glu | Gly | Tyr | Asn | Val | Tyr | Gly | Ile | Glu | Ser |
| 865 | | | | | 870 | | | | | 875 | | | | | 880 |
| Val | Lys | Ile | | | | | | | | | | | | | |

( 2 ) INFORMATION FOR SEQ ID NO: 9:

( i ) SEQUENCE CHARACTERISTICS:
        ( A ) LENGTH: 2989 base pairs
        ( B ) TYPE: nucleic acid
        ( C ) STRANDEDNESS: single
        ( D ) TOPOLOGY: linear ( i i ) MOLECULE TYPE: cDNA to mRNA ( v i ) ORIGINAL SOURCE:
        ( A ) ORGANISM: Homo sapiens
        ( B ) DEVELOPMENTAL STAGE: adult
        ( C ) TISSUE TYPE: brain ( i x ) FEATURE:
        ( A ) NAME/KEY: CDS
        ( B ) LOCATION: 73..2736

( x i ) SEQUENCE DESCRIPTION: SEQ ID NO: 9:

| | | | | | | | | | | |
|---|---|---|---|---|---|---|---|---|---|---|
| CTGACGACTC | CTGAGTTGCG | CCCATGCTCT | TGTCAGCTTC | GTTTAGGCG | TAGCATGGCC | | | | | 60 |

AGGCAGAAGA AA ATG GGG CAA AGC GTG CTC CGG GCG GTC TTC TTT TTA     108
                  Met Gly Gln Ser Val Leu Arg Ala Val Phe Phe Leu
                   1              5                   10

GTC CTG GGG CTT TTG GGT CAT TCT CAC GGA GGA TTC CCC AAC ACC ATC     156
Val Leu Gly Leu Leu Gly His Ser His Gly Gly Phe Pro Asn Thr Ile
        15                  20                   25

AGC ATA GGT GGA CTT TTC ATG AGA AAC ACA GTG CAG GAG CAC AGC GCT     204
Ser Ile Gly Gly Leu Phe Met Arg Asn Thr Val Gln Glu His Ser Ala
        30                  35                   40

TTC CGC TTT GCC GTG CAG TTA TAC AAC ACC AAC CAG AAC ACC ACC GAG     252
Phe Arg Phe Ala Val Gln Leu Tyr Asn Thr Asn Gln Asn Thr Thr Glu
45                  50                   55                   60

AAG CCC TTC CAT TTG AAT TAC CAC GTA GAT CAC TTG GAT TCC TCC AAT     300
Lys Pro Phe His Leu Asn Tyr His Val Asp His Leu Asp Ser Ser Asn
                  65                  70                   75

AGT TTT TCC GTG ACA AAT GCT TTC TGC TCC CAG TTC TCG AGA GGG GTG     348
Ser Phe Ser Val Thr Asn Ala Phe Cys Ser Gln Phe Ser Arg Gly Val
                80                  85                   90

TAT GCC ATC TTT GGA TTC TAT GAC CAG ATG TCA ATG AAC ACC CTG ACC     396
Tyr Ala Ile Phe Gly Phe Tyr Asp Gln Met Ser Met Asn Thr Leu Thr
                95                  100               105

TCC TTC TGT GGG GCC CTG CAC ACA TCC TTT GTT ACG CCT AGC TTC CCC     444
Ser Phe Cys Gly Ala Leu His Thr Ser Phe Val Thr Pro Ser Phe Pro
110                  115                 120

ACT GAC GCA GAT GTG CAG TTT GTC ATC CAG ATG CGC CCA GCC TTG AAG     492
Thr Asp Ala Asp Val Gln Phe Val Ile Gln Met Arg Pro Ala Leu Lys
125                  130                  135               140

GGC GCT ATT CTG AGT CTT CTG GGT CAT TAC AAG TGG GAG AAG TTT GTG     540
Gly Ala Ile Leu Ser Leu Leu Gly His Tyr Lys Trp Glu Lys Phe Val
                  145                  150               155

TAC CTC TAT GAC ACA GAA CGA GGA TTT TCC ATC CTC CAA GCG ATT ATG     588
Tyr Leu Tyr Asp Thr Glu Arg Gly Phe Ser Ile Leu Gln Ala Ile Met
                160                  165               170

GAA GCA GCA GTG CAA AAC AAC TGG CAA GTA ACA GCA AGG TCT GTG GGA     636
Glu Ala Ala Val Gln Asn Asn Trp Gln Val Thr Ala Arg Ser Val Gly
                175                  180               185

AAC ATA AAG GAC GTC CAA GAA TTC AGG CGC ATC ATT GAA GAA ATG GAC     684
Asn Ile Lys Asp Val Gln Glu Phe Arg Arg Ile Ile Glu Glu Met Asp
        190                  195                  200

AGG AGG CAG GAA AAG CGA TAC TTG ATT GAC TGC GAA GTC GAA AGG ATT     732
Arg Arg Gln Glu Lys Arg Tyr Leu Ile Asp Cys Glu Val Glu Arg Ile
205                  210                  215               220

AAC ACA ATT TTG GAA CAG GTT GTG ATC CTA GGG AAA CAC TCA AGA GGT     780
Asn Thr Ile Leu Glu Gln Val Val Ile Leu Gly Lys His Ser Arg Gly
                225                  230               235

TAT CAC TAC ATG CTC GCT AAC CTG GGT TTT ACT GAT ATT TTA CTG GAA     828
Tyr His Tyr Met Leu Ala Asn Leu Gly Phe Thr Asp Ile Leu Leu Glu
                240                  245               250

AGA GTC ATG CAT GGG GGA GCC AAC ATT ACA GGT TTC CAG ATT GTC AAC     876
Arg Val Met His Gly Gly Ala Asn Ile Thr Gly Phe Gln Ile Val Asn
                255                  260               265

AAT GAA AAC CCT ATG GTT CAG CAG TTC ATA CAG CGC TGG GTG AGG CTG     924
Asn Glu Asn Pro Met Val Gln Gln Phe Ile Gln Arg Trp Val Arg Leu
        270                  275                  280

GAT GAA AGG GAA TTC CCT GAA GCC AAG AAT GCA CCA CTA AAG TAT ACA     972
Asp Glu Arg Glu Phe Pro Glu Ala Lys Asn Ala Pro Leu Lys Tyr Thr
285                  290                  295               300

TCT GCA TTG ACA CAC GAC GCA ATA CTG GTC ATA GCA GAA GCT TTC CGC     1020

|     |     |     |     |     |     |     |     |     |     |     |     |     |     |     |      |
|-----|-----|-----|-----|-----|-----|-----|-----|-----|-----|-----|-----|-----|-----|-----|------|
| Ser | Ala | Leu | Thr | His | Asp | Ala | Ile | Leu | Val | Ile | Ala | Glu | Ala | Phe | Arg  |
|     |     |     |     | 305 |     |     |     |     | 310 |     |     |     |     | 315 |      |

| TAC | CTG | AGG | AGG | CAG | CGA | GTA | GAT | GTG | TCC | CGG | AGA | GGA | AGT | GCT | GGA | 1068 |
|-----|-----|-----|-----|-----|-----|-----|-----|-----|-----|-----|-----|-----|-----|-----|-----|------|
| Tyr | Leu | Arg | Arg | Gln | Arg | Val | Asp | Val | Ser | Arg | Arg | Gly | Ser | Ala | Gly |      |
|     |     |     | 320 |     |     |     |     | 325 |     |     |     |     | 330 |     |     |      |

| GAC | TGC | TTA | GCA | AAT | CCT | GCT | GTG | CCC | TGG | AGT | CAA | GGA | ATT | GAT | ATT | 1116 |
|-----|-----|-----|-----|-----|-----|-----|-----|-----|-----|-----|-----|-----|-----|-----|-----|------|
| Asp | Cys | Leu | Ala | Asn | Pro | Ala | Val | Pro | Trp | Ser | Gln | Gly | Ile | Asp | Ile |      |
|     |     |     | 335 |     |     |     | 340 |     |     |     |     | 345 |     |     |     |      |

| GAG | AGA | GCT | CTG | AAA | ATG | GTG | CAA | GTA | CAA | GGA | ATG | ACT | GGA | AAT | ATT | 1164 |
|-----|-----|-----|-----|-----|-----|-----|-----|-----|-----|-----|-----|-----|-----|-----|-----|------|
| Glu | Arg | Ala | Leu | Lys | Met | Val | Gln | Val | Gln | Gly | Met | Thr | Gly | Asn | Ile |      |
|     |     | 350 |     |     |     | 355 |     |     |     |     | 360 |     |     |     |     |      |

| CAA | TTT | GAC | ACT | TAT | GGA | CGT | AGG | ACA | AAT | TAT | ACC | ATC | GAT | GTG | TAT | 1212 |
|-----|-----|-----|-----|-----|-----|-----|-----|-----|-----|-----|-----|-----|-----|-----|-----|------|
| Gln | Phe | Asp | Thr | Tyr | Gly | Arg | Arg | Thr | Asn | Tyr | Thr | Ile | Asp | Val | Tyr |      |
| 365 |     |     |     |     | 370 |     |     |     |     | 375 |     |     |     |     | 380 |      |

| GAA | ATG | AAA | GTC | AGT | GGC | TCT | CGA | AAA | GCT | GGC | TAC | TGG | AAC | GAG | TAT | 1260 |
|-----|-----|-----|-----|-----|-----|-----|-----|-----|-----|-----|-----|-----|-----|-----|-----|------|
| Glu | Met | Lys | Val | Ser | Gly | Ser | Arg | Lys | Ala | Gly | Tyr | Trp | Asn | Glu | Tyr |      |
|     |     |     |     | 385 |     |     |     |     | 390 |     |     |     |     | 395 |     |      |

| GAA | AGG | TTT | GTG | CCT | TTC | TCA | GAT | CAG | CAA | ATC | AGC | AAT | GAC | AGT | GCA | 1308 |
|-----|-----|-----|-----|-----|-----|-----|-----|-----|-----|-----|-----|-----|-----|-----|-----|------|
| Glu | Arg | Phe | Val | Pro | Phe | Ser | Asp | Gln | Gln | Ile | Ser | Asn | Asp | Ser | Ala |      |
|     |     |     | 400 |     |     |     | 405 |     |     |     |     | 410 |     |     |     |      |

| TCC | TCA | GAG | AAT | CGG | ACC | ATA | GTA | GTG | ACT | ACC | ATT | CTG | GAA | TCA | CCA | 1356 |
|-----|-----|-----|-----|-----|-----|-----|-----|-----|-----|-----|-----|-----|-----|-----|-----|------|
| Ser | Ser | Glu | Asn | Arg | Thr | Ile | Val | Val | Thr | Thr | Ile | Leu | Glu | Ser | Pro |      |
|     |     | 415 |     |     |     | 420 |     |     |     |     | 425 |     |     |     |     |      |

| TAT | GTA | ATG | TAC | AAG | AAG | AAC | CAT | GAG | CAA | CTG | GAA | GGA | AAT | GAA | CGA | 1404 |
|-----|-----|-----|-----|-----|-----|-----|-----|-----|-----|-----|-----|-----|-----|-----|-----|------|
| Tyr | Val | Met | Tyr | Lys | Lys | Asn | His | Glu | Gln | Leu | Glu | Gly | Asn | Glu | Arg |      |
|     |     | 430 |     |     |     | 435 |     |     |     |     | 440 |     |     |     |     |      |

| TAT | GAA | GGC | TAT | TGT | GTA | GAC | CTA | GCC | TAT | GAA | ATA | GCC | AAA | CAT | GTA | 1452 |
|-----|-----|-----|-----|-----|-----|-----|-----|-----|-----|-----|-----|-----|-----|-----|-----|------|
| Tyr | Glu | Gly | Tyr | Cys | Val | Asp | Leu | Ala | Tyr | Glu | Ile | Ala | Lys | His | Val |      |
| 445 |     |     |     | 450 |     |     |     |     | 455 |     |     |     |     | 460 |     |      |

| AGG | ATC | AAA | TAC | AAA | TTG | TCC | ATC | GTT | GGT | GAC | GGG | AAA | TAT | GGT | GCA | 1500 |
|-----|-----|-----|-----|-----|-----|-----|-----|-----|-----|-----|-----|-----|-----|-----|-----|------|
| Arg | Ile | Lys | Tyr | Lys | Leu | Ser | Ile | Val | Gly | Asp | Gly | Lys | Tyr | Gly | Ala |      |
|     |     |     |     | 465 |     |     |     |     | 470 |     |     |     |     | 475 |     |      |

| AGG | GAT | CCA | GAG | ACT | AAA | ATA | TGG | AAC | GGC | ATG | GTT | GGG | GAA | CTT | GTC | 1548 |
|-----|-----|-----|-----|-----|-----|-----|-----|-----|-----|-----|-----|-----|-----|-----|-----|------|
| Arg | Asp | Pro | Glu | Thr | Lys | Ile | Trp | Asn | Gly | Met | Val | Gly | Glu | Leu | Val |      |
|     |     |     | 480 |     |     |     |     | 485 |     |     |     |     | 490 |     |     |      |

| TAT | GGG | AGA | GCT | GAT | ATA | GCT | GTT | GCT | CCA | CTC | ACT | ATA | ACA | TTG | GTC | 1596 |
|-----|-----|-----|-----|-----|-----|-----|-----|-----|-----|-----|-----|-----|-----|-----|-----|------|
| Tyr | Gly | Arg | Ala | Asp | Ile | Ala | Val | Ala | Pro | Leu | Thr | Ile | Thr | Leu | Val |      |
|     |     | 495 |     |     |     |     | 500 |     |     |     |     | 505 |     |     |     |      |

| CGT | GAA | GAA | GTC | ATA | GAT | TTT | TCA | AAG | CCA | TTC | ATG | AGC | CTG | GGC | ATC | 1644 |
|-----|-----|-----|-----|-----|-----|-----|-----|-----|-----|-----|-----|-----|-----|-----|-----|------|
| Arg | Glu | Glu | Val | Ile | Asp | Phe | Ser | Lys | Pro | Phe | Met | Ser | Leu | Gly | Ile |      |
| 510 |     |     |     |     | 515 |     |     |     |     | 520 |     |     |     |     |     |      |

| TCC | ATC | ATG | ATA | AAG | AAG | CCT | CAG | AAA | TCA | AAA | CCA | GGC | GTA | TTC | TCA | 1692 |
|-----|-----|-----|-----|-----|-----|-----|-----|-----|-----|-----|-----|-----|-----|-----|-----|------|
| Ser | Ile | Met | Ile | Lys | Lys | Pro | Gln | Lys | Ser | Lys | Pro | Gly | Val | Phe | Ser |      |
| 525 |     |     |     | 530 |     |     |     |     | 535 |     |     |     |     | 540 |     |      |

| TTT | CTG | GAT | CCC | CTG | GCT | TAT | GAA | ATC | TGG | ATG | TGC | ATT | GTC | TTT | GCT | 1740 |
|-----|-----|-----|-----|-----|-----|-----|-----|-----|-----|-----|-----|-----|-----|-----|-----|------|
| Phe | Leu | Asp | Pro | Leu | Ala | Tyr | Glu | Ile | Trp | Met | Cys | Ile | Val | Phe | Ala |      |
|     |     |     |     | 545 |     |     |     |     | 550 |     |     |     |     | 555 |     |      |

| TAC | ATT | GGA | GTC | AGC | GTA | GTT | CTT | TTC | CTA | GTC | AGC | AGG | TTC | AGT | CCT | 1788 |
|-----|-----|-----|-----|-----|-----|-----|-----|-----|-----|-----|-----|-----|-----|-----|-----|------|
| Tyr | Ile | Gly | Val | Ser | Val | Val | Leu | Phe | Leu | Val | Ser | Arg | Phe | Ser | Pro |      |
|     |     |     | 560 |     |     |     |     | 565 |     |     |     |     | 570 |     |     |      |

| TAT | GAA | TGG | CAC | TTG | GAA | GAC | AAC | AAT | GAA | GAA | CCT | CGT | GAC | CCA | CAA | 1836 |
|-----|-----|-----|-----|-----|-----|-----|-----|-----|-----|-----|-----|-----|-----|-----|-----|------|
| Tyr | Glu | Trp | His | Leu | Glu | Asp | Asn | Asn | Glu | Glu | Pro | Arg | Asp | Pro | Gln |      |
|     |     | 575 |     |     |     |     | 580 |     |     |     |     | 585 |     |     |     |      |

| AGT | CCT | CCT | GAT | CCT | CCA | AAT | GAA | TTT | GGA | ATA | TTT | AAC | AGT | CTT | TGG | 1884 |
|-----|-----|-----|-----|-----|-----|-----|-----|-----|-----|-----|-----|-----|-----|-----|-----|------|
| Ser | Pro | Pro | Asp | Pro | Pro | Asn | Glu | Phe | Gly | Ile | Phe | Asn | Ser | Leu | Trp |      |
|     | 590 |     |     |     |     | 595 |     |     |     |     | 600 |     |     |     |     |      |

| TTT | TCC | TTG | GGT | GCC | TTT | ATG | CAG | CAA | GGA | TGT | GAT | ATT | TCT | CCA | AGA | 1932 |
|-----|-----|-----|-----|-----|-----|-----|-----|-----|-----|-----|-----|-----|-----|-----|-----|------|
| Phe | Ser | Leu | Gly | Ala | Phe | Met | Gln | Gln | Gly | Cys | Asp | Ile | Ser | Pro | Arg |      |
| 605 |     |     |     |     | 610 |     |     |     |     | 615 |     |     |     |     | 620 |      |

| TCA | CTC | TCC | GGG | CGC | ATT | GTT | GGA | GGG | GTT | TGG | TGG | TTC | TTC | ACC | CTG | 1980 |

|     |     |     |     |     |     |     |     |     |     |     |     |     |     |     |     |
| --- | --- | --- | --- | --- | --- | --- | --- | --- | --- | --- | --- | --- | --- | --- | --- |
| Ser | Leu | Ser | Gly | Arg<br>625 | Ile | Val | Gly | Gly<br>630 | Val | Trp | Trp | Phe | Phe<br>635 | Thr | Leu |

| ATC | ATA | ATT | TCT | TCC | TAT | ACT | GCC | AAT | CTC | GCT | GCT | TTC | CTG | ACT | GTG | 2028 |
|---|---|---|---|---|---|---|---|---|---|---|---|---|---|---|---|---|
| Ile | Ile | Ile | Ser<br>640 | Ser | Tyr | Thr | Ala | Asn<br>645 | Leu | Ala | Ala | Phe | Leu<br>650 | Thr | Val |  |

| GAG | AGG | ATG | GTT | TCT | CCC | ATA | GAG | AGT | GCT | GAA | GAC | TTA | GCT | AAA | CAG | 2076 |
|---|---|---|---|---|---|---|---|---|---|---|---|---|---|---|---|---|
| Glu | Arg | Met<br>655 | Val | Ser | Pro | Ile | Glu<br>660 | Ser | Ala | Glu | Asp | Leu<br>665 | Ala | Lys | Gln |  |

| ACT | GAA | ATT | GCA | TAT | GGG | ACC | CTG | GAC | TCC | GGT | TCA | ACA | AAA | GAA | TTT | 2124 |
|---|---|---|---|---|---|---|---|---|---|---|---|---|---|---|---|---|
| Thr | Glu<br>670 | Ile | Ala | Tyr | Gly | Thr<br>675 | Leu | Asp | Ser | Gly | Ser<br>680 | Thr | Lys | Glu | Phe |  |

| TTC | AGA | AGA | TCC | AAA | ATT | GCT | GTG | TAC | GAG | AAA | ATG | TGG | TCT | TAC | ATG | 2172 |
|---|---|---|---|---|---|---|---|---|---|---|---|---|---|---|---|---|
| Phe<br>685 | Arg | Arg | Ser | Lys | Ile<br>690 | Ala | Val | Tyr | Glu | Lys<br>695 | Met | Trp | Ser | Tyr | Met<br>700 |  |

| AAA | TCA | GCG | GAG | CCA | TCT | GTG | TTT | ACC | AAA | ACA | ACA | GCA | GAC | GGA | GTG | 2220 |
|---|---|---|---|---|---|---|---|---|---|---|---|---|---|---|---|---|
| Lys | Ser | Ala | Glu | Pro<br>705 | Ser | Val | Phe | Thr | Lys<br>710 | Thr | Thr | Ala | Asp | Gly<br>715 | Val |  |

| GCC | CGA | GTG | CGA | AAG | TCC | AAG | GGA | AAG | TTC | GCC | TTC | CTG | CTG | GAG | TCA | 2268 |
|---|---|---|---|---|---|---|---|---|---|---|---|---|---|---|---|---|
| Ala | Arg | Val | Arg<br>720 | Lys | Ser | Lys | Gly | Lys<br>725 | Phe | Ala | Phe | Leu | Leu<br>730 | Glu | Ser |  |

| ACC | ATG | AAT | GAG | TAC | ATT | GAG | CAG | AGA | AAA | CCA | TGT | GAT | ACG | ATG | AAA | 2316 |
|---|---|---|---|---|---|---|---|---|---|---|---|---|---|---|---|---|
| Thr | Met | Asn<br>735 | Glu | Tyr | Ile | Glu | Gln<br>740 | Arg | Lys | Pro | Cys | Asp<br>745 | Thr | Met | Lys |  |

| GTT | GGT | GGA | AAT | CTG | GAT | TCC | AAA | GGC | TAT | GGT | GTG | GCA | ACC | CCT | AAA | 2364 |
|---|---|---|---|---|---|---|---|---|---|---|---|---|---|---|---|---|
| Val | Gly<br>750 | Gly | Asn | Leu | Asp | Ser<br>755 | Lys | Gly | Tyr | Gly | Val<br>760 | Ala | Thr | Pro | Lys |  |

| GGC | TCA | GCA | TTA | GGA | ACG | CCT | GTA | AAC | CTT | GCA | GTA | TTG | AAA | CTC | AGT | 2412 |
|---|---|---|---|---|---|---|---|---|---|---|---|---|---|---|---|---|
| Gly<br>765 | Ser | Ala | Leu | Gly | Thr<br>770 | Pro | Val | Asn | Leu | Ala<br>775 | Val | Leu | Lys | Leu | Ser<br>780 |  |

| GAA | CAA | GGC | ATC | TTA | GAC | AAG | CTG | AAA | AAC | AAA | TGG | TGG | TAC | GAT | AAG | 2460 |
|---|---|---|---|---|---|---|---|---|---|---|---|---|---|---|---|---|
| Glu | Gln | Gly | Ile | Leu<br>785 | Asp | Lys | Leu | Lys | Asn<br>790 | Lys | Trp | Trp | Tyr | Asp<br>795 | Lys |  |

| GGG | GAA | TGT | GGA | GCC | AAG | GAC | TCC | GGG | AGT | AAG | GAC | AAG | ACC | AGC | GCT | 2508 |
|---|---|---|---|---|---|---|---|---|---|---|---|---|---|---|---|---|
| Gly | Glu | Cys | Gly<br>800 | Ala | Lys | Asp | Ser | Gly<br>805 | Ser | Lys | Asp | Lys | Thr<br>810 | Ser | Ala |  |

| CTG | AGC | CTG | AGC | AAT | GTG | GCA | GGC | GTT | TTC | TAT | ATA | CTT | GTC | GGA | GGT | 2556 |
|---|---|---|---|---|---|---|---|---|---|---|---|---|---|---|---|---|
| Leu | Ser | Leu | Ser<br>815 | Asn | Val | Ala | Gly | Val<br>820 | Phe | Tyr | Ile | Leu | Val<br>825 | Gly | Gly |  |

| CTG | GGG | CTG | GCC | ATG | ATG | GTG | GCT | TTG | ATA | GAA | TTC | TGT | TAC | AAA | TCA | 2604 |
|---|---|---|---|---|---|---|---|---|---|---|---|---|---|---|---|---|
| Leu | Gly<br>830 | Leu | Ala | Met | Met | Val<br>835 | Ala | Leu | Ile | Glu | Phe<br>840 | Cys | Tyr | Lys | Ser |  |

| CGG | GCA | GAG | TCC | AAA | CGC | ATG | AAA | CTC | ACA | AAG | AAC | ACC | CAA | AAC | TTT | 2652 |
|---|---|---|---|---|---|---|---|---|---|---|---|---|---|---|---|---|
| Arg<br>845 | Ala | Glu | Ser | Lys | Arg<br>850 | Met | Lys | Leu | Thr | Lys<br>855 | Asn | Thr | Gln | Asn | Phe<br>860 |  |

| AAG | CCT | GCT | CCT | GCC | ACC | AAC | ACT | CAG | AAT | TAT | GCT | ACA | TAC | AGA | GAA | 2700 |
|---|---|---|---|---|---|---|---|---|---|---|---|---|---|---|---|---|
| Lys | Pro | Ala | Pro | Ala<br>865 | Thr | Asn | Thr | Gln | Asn<br>870 | Tyr | Ala | Thr | Tyr | Arg<br>875 | Glu |  |

| GGC | TAC | AAC | GTG | TAT | GGA | ACA | GAG | AGT | GTT | AAG | ATC | TAGGGATCCC | 2746 |
|---|---|---|---|---|---|---|---|---|---|---|---|---|---|
| Gly | Tyr | Asn | Val<br>880 | Tyr | Gly | Thr | Glu | Ser<br>885 | Val | Lys | Ile |  |  |

| TTCCCACTGG | AGGCATGTGA | TGAGAGGAAA | TCACCGAAAA | CGTGGCTGCT | TCAAGGATCC | 2806 |
|---|---|---|---|---|---|---|
| TGAGCCAGAT | TTCACTCTCC | TTGGTGTCGG | GCATGACACG | AATATTGCTG | ATGGTGCAAT | 2866 |
| GACCTTTCAA | TAGGAAAAAC | TGGTTTTTTT | TTCCTTCAGT | GCCTTATGGA | ACACTCTGAG | 2926 |
| ACTCGCGACA | ATGCAAACCA | TCATTGAAAT | CTTTTTGCTT | TGCTTGAAAA | AAAAAAAAA | 2986 |
| AAA |  |  |  |  |  | 2989 |

( 2 ) INFORMATION FOR SEQ ID NO:10:

( i ) SEQUENCE CHARACTERISTICS:
    ( A ) LENGTH: 888 amino acids
    ( B ) TYPE: amino acid
    ( D ) TOPOLOGY: linear ( i i ) MOLECULE TYPE: protein ( x i ) SEQUENCE DESCRIPTION: SEQ ID NO: 10:

| Met | Gly | Gln | Ser | Val | Leu | Arg | Ala | Val | Phe | Phe | Leu | Val | Leu | Gly | Leu |
|---|---|---|---|---|---|---|---|---|---|---|---|---|---|---|---|
| 1 | | | | 5 | | | | | 10 | | | | | 15 | |
| Leu | Gly | His | Ser | His | Gly | Gly | Phe | Pro | Asn | Thr | Ile | Ser | Ile | Gly | Gly |
| | | | 20 | | | | | 25 | | | | | 30 | | |
| Leu | Phe | Met | Arg | Asn | Thr | Val | Gln | Glu | His | Ser | Ala | Phe | Arg | Phe | Ala |
| | | 35 | | | | | 40 | | | | | 45 | | | |
| Val | Gln | Leu | Tyr | Asn | Thr | Asn | Gln | Asn | Thr | Thr | Glu | Lys | Pro | Phe | His |
| | 50 | | | | | 55 | | | | | 60 | | | | |
| Leu | Asn | Tyr | His | Val | Asp | His | Leu | Asp | Ser | Ser | Asn | Ser | Phe | Ser | Val |
| 65 | | | | | 70 | | | | 75 | | | | | | 80 |
| Thr | Asn | Ala | Phe | Cys | Ser | Gln | Phe | Ser | Arg | Gly | Val | Tyr | Ala | Ile | Phe |
| | | | | 85 | | | | | 90 | | | | | 95 | |
| Gly | Phe | Tyr | Asp | Gln | Met | Ser | Met | Asn | Thr | Leu | Thr | Ser | Phe | Cys | Gly |
| | | | 100 | | | | | 105 | | | | | 110 | | |
| Ala | Leu | His | Thr | Ser | Phe | Val | Thr | Pro | Ser | Phe | Pro | Thr | Asp | Ala | Asp |
| | | 115 | | | | | 120 | | | | | 125 | | | |
| Val | Gln | Phe | Val | Ile | Gln | Met | Arg | Pro | Ala | Leu | Lys | Gly | Ala | Ile | Leu |
| | 130 | | | | | 135 | | | | | 140 | | | | |
| Ser | Leu | Leu | Gly | His | Tyr | Lys | Trp | Glu | Lys | Phe | Val | Tyr | Leu | Tyr | Asp |
| 145 | | | | | 150 | | | | 155 | | | | | | 160 |
| Thr | Glu | Arg | Gly | Phe | Ser | Ile | Leu | Gln | Ala | Ile | Met | Glu | Ala | Ala | Val |
| | | | | 165 | | | | 170 | | | | | 175 | | |
| Gln | Asn | Asn | Trp | Gln | Val | Thr | Ala | Arg | Ser | Val | Gly | Asn | Ile | Lys | Asp |
| | | | 180 | | | | | 185 | | | | | 190 | | |
| Val | Gln | Glu | Phe | Arg | Arg | Ile | Ile | Glu | Glu | Met | Asp | Arg | Arg | Gln | Glu |
| | | 195 | | | | | 200 | | | | | 205 | | | |
| Lys | Arg | Tyr | Leu | Ile | Asp | Cys | Glu | Val | Glu | Arg | Ile | Asn | Thr | Ile | Leu |
| | 210 | | | | | 215 | | | | | 220 | | | | |
| Glu | Gln | Val | Val | Ile | Leu | Gly | Lys | His | Ser | Arg | Gly | Tyr | His | Tyr | Met |
| 225 | | | | | 230 | | | | 235 | | | | | | 240 |
| Leu | Ala | Asn | Leu | Gly | Phe | Thr | Asp | Ile | Leu | Leu | Glu | Arg | Val | Met | His |
| | | | | 245 | | | | 250 | | | | | 255 | | |
| Gly | Gly | Ala | Asn | Ile | Thr | Gly | Phe | Gln | Ile | Val | Asn | Asn | Glu | Asn | Pro |
| | | | 260 | | | | | 265 | | | | | 270 | | |
| Met | Val | Gln | Gln | Phe | Ile | Gln | Arg | Trp | Val | Arg | Leu | Asp | Glu | Arg | Glu |
| | | 275 | | | | | 280 | | | | | 285 | | | |
| Phe | Pro | Glu | Ala | Lys | Asn | Ala | Pro | Leu | Lys | Tyr | Thr | Ser | Ala | Leu | Thr |
| | 290 | | | | | 295 | | | | | 300 | | | | |
| His | Asp | Ala | Ile | Leu | Val | Ile | Ala | Glu | Ala | Phe | Arg | Tyr | Leu | Arg | Arg |
| 305 | | | | | 310 | | | | 315 | | | | | | 320 |
| Gln | Arg | Val | Asp | Val | Ser | Arg | Arg | Gly | Ser | Ala | Gly | Asp | Cys | Leu | Ala |
| | | | | 325 | | | | 330 | | | | | 335 | | |
| Asn | Pro | Ala | Val | Pro | Trp | Ser | Gln | Gly | Ile | Asp | Ile | Glu | Arg | Ala | Leu |
| | | | 340 | | | | | 345 | | | | | 350 | | |
| Lys | Met | Val | Gln | Val | Gln | Gly | Met | Thr | Gly | Asn | Ile | Gln | Phe | Asp | Thr |
| | | 355 | | | | | 360 | | | | | 365 | | | |
| Tyr | Gly | Arg | Arg | Thr | Asn | Tyr | Thr | Ile | Asp | Val | Tyr | Glu | Met | Lys | Val |
| | 370 | | | | | 375 | | | | | 380 | | | | |

| Ser | Gly | Ser | Arg | Lys | Ala | Gly | Tyr | Trp | Asn | Glu | Tyr | Glu | Arg | Phe | Val |
| 385 | | | | 390 | | | | | 395 | | | | | | 400 |

Pro Phe Ser Asp Gln Gln Ile Ser Asn Asp Ser Ala Ser Ser Glu Asn
            405              410                415

Arg Thr Ile Val Val Thr Thr Ile Leu Glu Ser Pro Tyr Val Met Tyr
        420              425              430

Lys Lys Asn His Glu Gln Leu Glu Gly Asn Glu Arg Tyr Glu Gly Tyr
            435              440              445

Cys Val Asp Leu Ala Tyr Glu Ile Ala Lys His Val Arg Ile Lys Tyr
        450              455              460

Lys Leu Ser Ile Val Gly Asp Gly Lys Tyr Gly Ala Arg Asp Pro Glu
465              470              475              480

Thr Lys Ile Trp Asn Gly Met Val Gly Glu Leu Val Tyr Gly Arg Ala
            485              490              495

Asp Ile Ala Val Ala Pro Leu Thr Ile Thr Leu Val Arg Glu Glu Val
            500              505              510

Ile Asp Phe Ser Lys Pro Phe Met Ser Leu Gly Ile Ser Ile Met Ile
        515              520              525

Lys Lys Pro Gln Lys Ser Lys Pro Gly Val Phe Ser Phe Leu Asp Pro
530              535              540

Leu Ala Tyr Glu Ile Trp Met Cys Ile Val Phe Ala Tyr Ile Gly Val
545              550              555              560

Ser Val Val Leu Phe Leu Val Ser Arg Phe Ser Pro Tyr Glu Trp His
            565              570              575

Leu Glu Asp Asn Asn Glu Glu Pro Arg Asp Pro Gln Ser Pro Pro Asp
            580              585              590

Pro Pro Asn Glu Phe Gly Ile Phe Asn Ser Leu Trp Phe Ser Leu Gly
        595              600              605

Ala Phe Met Gln Gln Gly Cys Asp Ile Ser Pro Arg Ser Leu Ser Gly
        610              615              620

Arg Ile Val Gly Gly Val Trp Trp Phe Phe Thr Leu Ile Ile Ile Ser
625              630              635              640

Ser Tyr Thr Ala Asn Leu Ala Ala Phe Leu Thr Val Glu Arg Met Val
            645              650              655

Ser Pro Ile Glu Ser Ala Glu Asp Leu Ala Lys Gln Thr Glu Ile Ala
            660              665              670

Tyr Gly Thr Leu Asp Ser Gly Ser Thr Lys Glu Phe Phe Arg Arg Ser
        675              680              685

Lys Ile Ala Val Tyr Glu Lys Met Trp Ser Tyr Met Lys Ser Ala Glu
690              695              700

Pro Ser Val Phe Thr Lys Thr Thr Ala Asp Gly Val Ala Arg Val Arg
705              710              715              720

Lys Ser Lys Gly Lys Phe Ala Phe Leu Leu Glu Ser Thr Met Asn Glu
            725              730              735

Tyr Ile Glu Gln Arg Lys Pro Cys Asp Thr Met Lys Val Gly Gly Asn
        740              745              750

Leu Asp Ser Lys Gly Tyr Gly Val Ala Thr Pro Lys Gly Ser Ala Leu
        755              760              765

Gly Thr Pro Val Asn Leu Ala Val Leu Lys Leu Ser Glu Gln Gly Ile
    770              775              780

Leu Asp Lys Leu Lys Asn Lys Trp Trp Tyr Asp Lys Gly Glu Cys Gly
785              790              795              800

Ala Lys Asp Ser Gly Ser Lys Asp Lys Thr Ser Ala Leu Ser Leu Ser

|  | 805 |  | 810 |  | 815 |  |
|---|---|---|---|---|---|---|
| Asn Val Ala Gly Val Phe Tyr Ile Leu Val Gly Gly Leu Gly Leu Ala |  |  |  |  |  |  |
| 820 | 825 | 830 |
| Met Met Val Ala Leu Ile Glu Phe Cys Tyr Lys Ser Arg Ala Glu Ser |
| 835 | 840 | 845 |
| Lys Arg Met Lys Leu Thr Lys Asn Thr Gln Asn Phe Lys Pro Ala Pro |
| 850 | 855 | 860 |
| Ala Thr Asn Thr Gln Asn Tyr Ala Thr Tyr Arg Glu Gly Tyr Asn Val |
| 865 | 870 | 875 | 880 |
| Tyr Gly Thr Glu Ser Val Lys Ile |
| 885 |

( 2 ) INFORMATION FOR SEQ ID NO: 11:

( i ) SEQUENCE CHARACTERISTICS:
        ( A ) LENGTH: 2989 base pairs
        ( B ) TYPE: nucleic acid
        ( C ) STRANDEDNESS: single
        ( D ) TOPOLOGY: linear ( i i ) MOLECULE TYPE: cDNA to mRNA ( v i ) ORIGINAL SOURCE:
        ( A ) ORGANISM: Homo sapiens
        ( B ) DEVELOPMENTAL STAGE: adult
        ( C ) TISSUE TYPE: brain ( i x ) FEATURE:
        ( A ) NAME/KEY: CDS
        ( B ) LOCATION: 73..2736

( x i ) SEQUENCE DESCRIPTION: SEQ ID NO: 11:

| | | | | |
|---|---|---|---|---|
| CTGACGACTC CTGAGTTGCG CCCATGCTCT TGTCAGCTTC GTTTTAGGCG TAGCATGGCC | | | | 60 |
| AGGCAGAAGA AA ATG GGG CAA AGC GTG CTC CGG GCG GTC TTC TTT TTA | | | | 108 |
|               Met Gly Gln Ser Val Leu Arg Ala Val Phe Phe Leu | | | | |
|                 1             5               10 | | | | |
| GTC CTG GGG CTT TTG GGT CAT TCT CAC GGA GGA TTC CCC AAC ACC ATC | | | | 156 |
| Val Leu Gly Leu Leu Gly His Ser His Gly Gly Phe Pro Asn Thr Ile | | | | |
|          15                  20                25 | | | | |
| AGC ATA GGT GGA CTT TTC ATG AGA AAC ACA GTG CAG GAG CAC AGC GCT | | | | 204 |
| Ser Ile Gly Gly Leu Phe Met Arg Asn Thr Val Gln Glu His Ser Ala | | | | |
|  30                  35                40 | | | | |
| TTC CGC TTT GCC GTG CAG TTA TAC AAC ACC AAC CAG AAC ACC ACC GAG | | | | 252 |
| Phe Arg Phe Ala Val Gln Leu Tyr Asn Thr Asn Gln Asn Thr Thr Glu | | | | |
| 45                  50                55                60 | | | | |
| AAG CCC TTC CAT TTG AAT TAC CAC GTA GAT CAC TTG GAT TCC TCC AAT | | | | 300 |
| Lys Pro Phe His Leu Asn Tyr His Val Asp His Leu Asp Ser Ser Asn | | | | |
|                65                70                75 | | | | |
| AGT TTT TCC GTG ACA AAT GCT TTC TGC TCC CAG TTC TCG AGA GGG GTG | | | | 348 |
| Ser Phe Ser Val Thr Asn Ala Phe Cys Ser Gln Phe Ser Arg Gly Val | | | | |
|             80                   85                90 | | | | |
| TAT GCC ATC TTT GGA TTC TAT GAC CAG ATG TCA ATG AAC ACC CTG ACC | | | | 396 |
| Tyr Ala Ile Phe Gly Phe Tyr Asp Gln Met Ser Met Asn Thr Leu Thr | | | | |
|         95                  100              105 | | | | |
| TCC TTC TGT GGG GCC CTG CAC ACA TCC TTT GTT ACG CCT AGC TTC CCC | | | | 444 |
| Ser Phe Cys Gly Ala Leu His Thr Ser Phe Val Thr Pro Ser Phe Pro | | | | |
|     110                  115              120 | | | | |
| ACT GAC GCA GAT GTG CAG TTT GTC ATC CAG ATG CGC CCA GCC TTG AAG | | | | 492 |
| Thr Asp Ala Asp Val Gln Phe Val Ile Gln Met Arg Pro Ala Leu Lys | | | | |
| 125                  130                135              140 | | | | |
| GGC GCT ATT CTG AGT CTT CTG GGT CAT TAC AAG TGG GAG AAG TTT GTG | | | | 540 |
| Gly Ala Ile Leu Ser Leu Leu Gly His Tyr Lys Trp Glu Lys Phe Val | | | | |
|                145                150                155 | | | | |

| | | | | | | | | | | | | | | | | |
|---|---|---|---|---|---|---|---|---|---|---|---|---|---|---|---|---|
| TAC | CTC | TAT | GAC | ACA | GAA | CGA | GGA | TTT | TCC | ATC | CTC | CAA | GCG | ATT | ATG | 588 |
| Tyr | Leu | Tyr | Asp | Thr | Glu | Arg | Gly | Phe | Ser | Ile | Leu | Gln | Ala | Ile | Met | |
| | | | 160 | | | | 165 | | | | | | 170 | | | |
| GAA | GCA | GCA | GTG | CAA | AAC | AAC | TGG | CAA | GTA | ACA | GCA | AGG | TCT | GTG | GGA | 636 |
| Glu | Ala | Ala | Val | Gln | Asn | Asn | Trp | Gln | Val | Thr | Ala | Arg | Ser | Val | Gly | |
| | | 175 | | | | | 180 | | | | | 185 | | | | |
| AAC | ATA | AAG | GAC | GTC | CAA | GAA | TTC | AGG | CGC | ATC | ATT | GAA | GAA | ATG | GAC | 684 |
| Asn | Ile | Lys | Asp | Val | Gln | Glu | Phe | Arg | Arg | Ile | Ile | Glu | Glu | Met | Asp | |
| | 190 | | | | | 195 | | | | | 200 | | | | | |
| AGG | AGG | CAG | GAA | AAG | CGA | TAC | TTG | ATT | GAC | TGC | GAA | GTC | GAA | AGG | ATT | 732 |
| Arg | Arg | Gln | Glu | Lys | Arg | Tyr | Leu | Ile | Asp | Cys | Glu | Val | Glu | Arg | Ile | |
| 205 | | | | | 210 | | | | | 215 | | | | | 220 | |
| AAC | ACA | ATT | TTG | GAA | CAG | GTT | GTG | ATC | CTA | GGG | AAA | CAC | TCA | AGA | GGT | 780 |
| Asn | Thr | Ile | Leu | Glu | Gln | Val | Val | Ile | Leu | Gly | Lys | His | Ser | Arg | Gly | |
| | | | | 225 | | | | | 230 | | | | | 235 | | |
| TAT | CAC | TAC | ATG | CTC | GCT | AAC | CTG | GGT | TTT | ACT | GAT | ATT | TTA | CTG | GAA | 828 |
| Tyr | His | Tyr | Met | Leu | Ala | Asn | Leu | Gly | Phe | Thr | Asp | Ile | Leu | Leu | Glu | |
| | | | 240 | | | | | 245 | | | | | 250 | | | |
| AGA | GTC | ATG | CAT | GGG | GGA | GCC | AAC | ATT | ACA | GGT | TTC | CAG | ATT | GTC | AAC | 876 |
| Arg | Val | Met | His | Gly | Gly | Ala | Asn | Ile | Thr | Gly | Phe | Gln | Ile | Val | Asn | |
| | | 255 | | | | | 260 | | | | | 265 | | | | |
| AAT | GAA | AAC | CCT | ATG | GTT | CAG | CAG | TTC | ATA | CAG | CGC | TGG | GTG | AGG | CTG | 924 |
| Asn | Glu | Asn | Pro | Met | Val | Gln | Gln | Phe | Ile | Gln | Arg | Trp | Val | Arg | Leu | |
| | 270 | | | | | 275 | | | | | 280 | | | | | |
| GAT | GAA | AGG | GAA | TTC | CCT | GAA | GCC | AAG | AAT | GCA | CCA | CTA | AAG | TAT | ACA | 972 |
| Asp | Glu | Arg | Glu | Phe | Pro | Glu | Ala | Lys | Asn | Ala | Pro | Leu | Lys | Tyr | Thr | |
| 285 | | | | | 290 | | | | | 295 | | | | | 300 | |
| TCT | GCA | TTG | ACA | CAC | GAC | GCA | ATA | CTG | GTC | ATA | GCA | GAA | GCT | TTC | CGC | 1020 |
| Ser | Ala | Leu | Thr | His | Asp | Ala | Ile | Leu | Val | Ile | Ala | Glu | Ala | Phe | Arg | |
| | | | | 305 | | | | | 310 | | | | | 315 | | |
| TAC | CTG | AGG | AGG | CAG | CGA | GTA | GAT | GTG | TCC | CGG | AGA | GGA | AGT | GCT | GGA | 1068 |
| Tyr | Leu | Arg | Arg | Gln | Arg | Val | Asp | Val | Ser | Arg | Arg | Gly | Ser | Ala | Gly | |
| | | | 320 | | | | | 325 | | | | | 330 | | | |
| GAC | TGC | TTA | GCA | AAT | CCT | GCT | GTG | CCC | TGG | AGT | CAA | GGA | ATT | GAT | ATT | 1116 |
| Asp | Cys | Leu | Ala | Asn | Pro | Ala | Val | Pro | Trp | Ser | Gln | Gly | Ile | Asp | Ile | |
| | | 335 | | | | | 340 | | | | | 345 | | | | |
| GAG | AGA | GCT | CTG | AAA | ATG | GTG | CAA | GTA | CAA | GGA | ATG | ACT | GGA | AAT | ATT | 1164 |
| Glu | Arg | Ala | Leu | Lys | Met | Val | Gln | Val | Gln | Gly | Met | Thr | Gly | Asn | Ile | |
| | 350 | | | | | 355 | | | | | 360 | | | | | |
| CAA | TTT | GAC | ACT | TAT | GGA | CGT | AGG | ACA | AAT | TAT | ACC | ATC | GAT | GTG | TAT | 1212 |
| Gln | Phe | Asp | Thr | Tyr | Gly | Arg | Arg | Thr | Asn | Tyr | Thr | Ile | Asp | Val | Tyr | |
| 365 | | | | | 370 | | | | | 375 | | | | | 380 | |
| GAA | ATG | AAA | GTC | AGT | GGC | TCT | CGA | AAA | GCT | GGC | TAC | TGG | AAC | GAG | TAT | 1260 |
| Glu | Met | Lys | Val | Ser | Gly | Ser | Arg | Lys | Ala | Gly | Tyr | Trp | Asn | Glu | Tyr | |
| | | | | 385 | | | | | 390 | | | | | 395 | | |
| GAA | AGG | TTT | GTG | CCT | TTC | TCA | GAT | CAG | CAA | ATC | AGC | AAT | GAC | AGT | GCA | 1308 |
| Glu | Arg | Phe | Val | Pro | Phe | Ser | Asp | Gln | Gln | Ile | Ser | Asn | Asp | Ser | Ala | |
| | | | 400 | | | | | 405 | | | | | 410 | | | |
| TCC | TCA | GAG | AAT | CGG | ACC | ATA | GTA | GTG | ACT | ACC | ATT | CTG | GAA | TCA | CCA | 1356 |
| Ser | Ser | Glu | Asn | Arg | Thr | Ile | Val | Val | Thr | Thr | Ile | Leu | Glu | Ser | Pro | |
| | | 415 | | | | | 420 | | | | | 425 | | | | |
| TAT | GTA | ATG | TAC | AAG | AAG | AAC | CAT | GAG | CAA | CTG | GAA | GGA | AAT | GAA | CGA | 1404 |
| Tyr | Val | Met | Tyr | Lys | Lys | Asn | His | Glu | Gln | Leu | Glu | Gly | Asn | Glu | Arg | |
| | 430 | | | | | 435 | | | | | 440 | | | | | |
| TAT | GAA | GGC | TAT | TGT | GTA | GAC | CTA | GCC | TAT | GAA | ATA | GCC | AAA | CAT | GTA | 1452 |
| Tyr | Glu | Gly | Tyr | Cys | Val | Asp | Leu | Ala | Tyr | Glu | Ile | Ala | Lys | His | Val | |
| 445 | | | | | 450 | | | | | 455 | | | | | 460 | |
| AGG | ATC | AAA | TAC | AAA | TTG | TCC | ATC | GTT | GGT | GAC | GGG | AAA | TAT | GGT | GCA | 1500 |
| Arg | Ile | Lys | Tyr | Lys | Leu | Ser | Ile | Val | Gly | Asp | Gly | Lys | Tyr | Gly | Ala | |
| | | | | 465 | | | | | 470 | | | | | 475 | | |

-continued

| | | | | | | | | | | | | | | | | |
|---|---|---|---|---|---|---|---|---|---|---|---|---|---|---|---|---|
| AGG | GAT | CCA | GAG | ACT | AAA | ATA | TGG | AAC | GGC | ATG | GTT | GGG | GAA | CTT | GTC | 1548 |
| Arg | Asp | Pro | Glu 480 | Thr | Lys | Ile | Trp | Asn 485 | Gly | Met | Val | Gly | Glu 490 | Leu | Val | |
| TAT | GGG | AGA | GCT | GAT | ATA | GCT | GTT | GCT | CCA | CTC | ACT | ATA | ACA | TTG | GTC | 1596 |
| Tyr | Gly | Arg 495 | Ala | Asp | Ile | Ala | Val 500 | Ala | Pro | Leu | Thr | Ile 505 | Thr | Leu | Val | |
| CGT | GAA | GAA | GTC | ATA | GAT | TTT | TCA | AAG | CCA | TTC | ATG | AGC | CTG | GGC | ATC | 1644 |
| Arg | Glu 510 | Glu | Val | Ile | Asp | Phe 515 | Ser | Lys | Pro | Phe | Met 520 | Ser | Leu | Gly | Ile | |
| TCC | ATC | ATG | ATA | AAG | AAG | CCT | CAG | AAA | TCA | AAA | CCA | GGC | GTA | TTC | TCA | 1692 |
| Ser 525 | Ile | Met | Ile | Lys | Lys 530 | Pro | Gln | Lys | Ser | Lys 535 | Pro | Gly | Val | Phe | Ser 540 | |
| TTT | CTG | GAT | CCC | CTG | GCT | TAT | GAA | ATC | TGG | ATG | TGC | ATT | GTC | TTT | GCT | 1740 |
| Phe | Leu | Asp | Pro | Leu 545 | Ala | Tyr | Glu | Ile | Trp 550 | Met | Cys | Ile | Val | Phe 555 | Ala | |
| TAC | ATT | GGA | GTC | AGC | GTA | GTT | CTT | TTC | CTA | GTC | AGC | AGG | TTC | AGT | CCT | 1788 |
| Tyr | Ile | Gly | Val 560 | Ser | Val | Val | Leu | Phe 565 | Leu | Val | Ser | Arg | Phe 570 | Ser | Pro | |
| TAT | GAA | TGG | CAC | TTG | GAA | GAC | AAC | AAT | GAA | GAA | CCT | CGT | GAC | CCA | CAA | 1836 |
| Tyr | Glu | Trp 575 | His | Leu | Glu | Asp | Asn 580 | Asn | Glu | Glu | Pro | Arg 585 | Asp | Pro | Gln | |
| AGT | CCT | CCT | GAT | CCT | CCA | AAT | GAA | TTT | GGA | ATA | TTT | AAC | AGT | CTT | TGG | 1884 |
| Ser | Pro 590 | Pro | Asp | Pro | Pro | Asn 595 | Glu | Phe | Gly | Ile | Phe 600 | Asn | Ser | Leu | Trp | |
| TTT | TCC | TTG | GGT | GCC | TTT | ATG | CAG | CAA | GGA | TGT | GAT | ATT | TCT | CCA | AGA | 1932 |
| Phe 605 | Ser | Leu | Gly | Ala | Phe 610 | Met | Gln | Gln | Gly | Cys 615 | Asp | Ile | Ser | Pro | Arg 620 | |
| TCA | CTC | TCC | GGG | CGC | ATT | GTT | GGA | GGG | GTT | TGG | TGG | TTC | TTC | ACC | CTG | 1980 |
| Ser | Leu | Ser | Gly | Arg 625 | Ile | Val | Gly | Gly | Val 630 | Trp | Trp | Phe | Phe | Thr 635 | Leu | |
| ATC | ATA | ATT | TCT | TCC | TAT | ACT | GCC | AAT | CTC | GCT | GCT | TTC | CTG | ACT | GTG | 2028 |
| Ile | Ile | Ile | Ser | Ser 640 | Tyr | Thr | Ala | Asn | Leu 645 | Ala | Ala | Phe | Leu | Thr 650 | Val | |
| GAG | AGG | ATG | GTT | TCT | CCC | ATA | GAG | AGT | GCT | GAA | GAC | TTA | GCT | AAA | CAG | 2076 |
| Glu | Arg | Met 655 | Val | Ser | Pro | Ile | Glu 660 | Ser | Ala | Glu | Asp | Leu 665 | Ala | Lys | Gln | |
| ACT | GAA | ATT | GCA | TAT | GGG | ACC | CTG | GAC | TCC | GGT | TCA | ACA | AAA | GAA | TTT | 2124 |
| Thr | Glu 670 | Ile | Ala | Tyr | Gly | Thr 675 | Leu | Asp | Ser | Gly | Ser 680 | Thr | Lys | Glu | Phe | |
| TTC | AGA | AGA | TCC | AAA | ATT | GCT | GTG | TAC | GAG | AAA | ATG | TGG | TCT | TAC | ATG | 2172 |
| Phe 685 | Arg | Arg | Ser | Lys | Ile 690 | Ala | Val | Tyr | Glu | Lys 695 | Met | Trp | Ser | Tyr | Met 700 | |
| AAA | TCA | GCG | GAG | CCA | TCT | GTG | TTT | ACC | AAA | ACA | ACA | GCA | GAC | GGA | GTG | 2220 |
| Lys | Ser | Ala | Glu | Pro 705 | Ser | Val | Phe | Thr | Lys 710 | Thr | Thr | Ala | Asp | Gly 715 | Val | |
| GCC | CGA | GTG | CGA | AAG | TCC | AAG | GGA | AAG | TTC | GCC | TTC | CTG | CTG | GAG | TCA | 2268 |
| Ala | Arg | Val | Arg 720 | Lys | Ser | Lys | Gly | Lys 725 | Phe | Ala | Phe | Leu | Leu 730 | Glu | Ser | |
| ACC | ATG | AAT | GAG | TAC | ATT | GAG | CAG | AGA | AAA | CCA | TGT | GAT | ACG | ATG | AAA | 2316 |
| Thr | Met | Asn 735 | Glu | Tyr | Ile | Glu | Gln 740 | Arg | Lys | Pro | Cys | Asp 745 | Thr | Met | Lys | |
| GTT | GGT | GGA | AAT | CTG | GAT | TCC | AAA | GGC | TAT | GGT | GTG | GCA | ACC | CCT | AAA | 2364 |
| Val | Gly | Gly | Asn | Leu 750 | Asp | Ser | Lys | Gly | Tyr 755 | Gly | Val | Ala | Thr | Pro 760 | Lys | |
| GGC | TCA | GCA | TTA | GGA | AAT | GCT | GTT | AAC | CTG | GCA | GTA | TTA | AAA | CTG | AAT | 2412 |
| Gly | Ser 765 | Ala | Leu | Gly | Asn | Ala 770 | Val | Asn | Leu | Ala | Val 775 | Leu | Lys | Leu | Asn 780 | |
| GAG | CAA | GGC | CTC | TTG | GAC | AAA | TTG | AAA | AAC | AAA | TGG | TGG | TAC | GAC | AAA | 2460 |
| Glu | Gln | Gly | Leu | Leu 785 | Asp | Lys | Leu | Lys | Asn 790 | Lys | Trp | Trp | Tyr | Asp 795 | Lys | |

| | | | | | | | | | | | | | | | | |
|---|---|---|---|---|---|---|---|---|---|---|---|---|---|---|---|---|
| GGA | GAG | TGC | GGC | AGC | GGG | GGC | GGT | GAC | TCC | AAG | GAC | AAG | ACC | AGC | GCT | 2508 |
| Gly | Glu | Cys | Gly | Ser | Gly | Gly | Gly | Asp | Ser | Lys | Asp | Lys | Thr | Ser | Ala | |
| | | | 800 | | | | | 805 | | | | 810 | | | | |
| CTG | AGC | CTG | AGC | AAT | GTG | GCA | GGC | GTT | TTC | TAT | ATA | CTT | GTC | GGA | GGT | 2556 |
| Leu | Ser | Leu | Ser | Asn | Val | Ala | Gly | Val | Phe | Tyr | Ile | Leu | Val | Gly | Gly | |
| | | | 815 | | | | 820 | | | | | 825 | | | | |
| CTG | GGG | CTG | GCC | ATG | ATG | GTG | GCT | TTG | ATA | GAA | TTC | TGT | TAC | AAA | TCA | 2604 |
| Leu | Gly | Leu | Ala | Met | Met | Val | Ala | Leu | Ile | Glu | Phe | Cys | Tyr | Lys | Ser | |
| | 830 | | | | 835 | | | | | 840 | | | | | | |
| CGG | GCA | GAG | TCC | AAA | CGC | ATG | AAA | CTC | ACA | AAG | AAC | ACC | CAA | AAC | TTT | 2652 |
| Arg | Ala | Glu | Ser | Lys | Arg | Met | Lys | Leu | Thr | Lys | Asn | Thr | Gln | Asn | Phe | |
| 845 | | | | | 850 | | | | 855 | | | | | 860 | | |
| AAG | CCT | GCT | CCT | GCC | ACC | AAC | ACT | CAG | AAT | TAT | GCT | ACA | TAC | AGA | GAA | 2700 |
| Lys | Pro | Ala | Pro | Ala | Thr | Asn | Thr | Gln | Asn | Tyr | Ala | Thr | Tyr | Arg | Glu | |
| | | | 865 | | | | | 870 | | | | | 875 | | | |
| GGC | TAC | AAC | GTG | TAT | GGA | ACA | GAG | AGT | GTT | AAG | ATC | TAGGGATCCC | | | | 2746 |
| Gly | Tyr | Asn | Val | Tyr | Gly | Thr | Glu | Ser | Val | Lys | Ile | | | | | |
| | | | 880 | | | | | 885 | | | | | | | | |

| | | | | | |
|---|---|---|---|---|---|
| TTCCCACTGG | AGGCATGTGA | TGAGAGGAAA | TCACCGAAAA | CGTGGCTGCT | TCAAGGATCC | 2806 |
| TGAGCCAGAT | TTCACTCTCC | TTGGTGTCGG | GCATGACACG | AATATTGCTG | ATGGTGCAAT | 2866 |
| GACCTTTCAA | TAGGAAAAAC | TGGTTTTTTT | TTCCTTCAGT | GCCTTATGGA | ACACTCTGAG | 2926 |
| ACTCGCGACA | ATGCAAACCA | TCATTGAAAT | CTTTTGCTT | TGCTTGAAAA | AAAAAAAAA | 2986 |
| AAA | | | | | | 2989 |

( 2 ) INFORMATION FOR SEQ ID NO:12:

( i ) SEQUENCE CHARACTERISTICS:
        ( A ) LENGTH: 888 amino acids
        ( B ) TYPE: amino acid
        ( D ) TOPOLOGY: linear ( i i ) MOLECULE TYPE: protein ( x i ) SEQUENCE DESCRIPTION: SEQ ID NO: 12:

| | | | | | | | | | | | | | | |
|---|---|---|---|---|---|---|---|---|---|---|---|---|---|---|
| Met | Gly | Gln | Ser | Val | Leu | Arg | Ala | Val | Phe | Phe | Leu | Val | Leu | Gly | Leu |
| 1 | | | | 5 | | | | | 10 | | | | | 15 | |
| Leu | Gly | His | Ser | His | Gly | Gly | Phe | Pro | Asn | Thr | Ile | Ser | Ile | Gly | Gly |
| | | | 20 | | | | | 25 | | | | | 30 | | |
| Leu | Phe | Met | Arg | Asn | Thr | Val | Gln | Glu | His | Ser | Ala | Phe | Arg | Phe | Ala |
| | | | 35 | | | | 40 | | | | | 45 | | | |
| Val | Gln | Leu | Tyr | Asn | Thr | Asn | Gln | Asn | Thr | Thr | Glu | Lys | Pro | Phe | His |
| | 50 | | | | | 55 | | | | | 60 | | | | |
| Leu | Asn | Tyr | His | Val | Asp | His | Leu | Asp | Ser | Ser | Asn | Ser | Phe | Ser | Val |
| 65 | | | | | 70 | | | | | 75 | | | | | 80 |
| Thr | Asn | Ala | Phe | Cys | Ser | Gln | Phe | Ser | Arg | Gly | Val | Tyr | Ala | Ile | Phe |
| | | | | 85 | | | | | 90 | | | | | 95 | |
| Gly | Phe | Tyr | Asp | Gln | Met | Ser | Met | Asn | Thr | Leu | Thr | Ser | Phe | Cys | Gly |
| | | | 100 | | | | | 105 | | | | | 110 | | |
| Ala | Leu | His | Thr | Ser | Phe | Val | Thr | Pro | Ser | Phe | Pro | Thr | Asp | Ala | Asp |
| | | 115 | | | | | 120 | | | | | 125 | | | |
| Val | Gln | Phe | Val | Ile | Gln | Met | Arg | Pro | Ala | Leu | Lys | Gly | Ala | Ile | Leu |
| | 130 | | | | | 135 | | | | | 140 | | | | |
| Ser | Leu | Leu | Gly | His | Tyr | Lys | Trp | Glu | Lys | Phe | Val | Tyr | Leu | Tyr | Asp |
| 145 | | | | | 150 | | | | | 155 | | | | | 160 |
| Thr | Glu | Arg | Gly | Phe | Ser | Ile | Leu | Gln | Ala | Ile | Met | Glu | Ala | Ala | Val |
| | | | | 165 | | | | | 170 | | | | | 175 | |

-continued

| Gln | Asn | Asn | Trp | Gln | Val | Thr | Ala | Arg | Ser | Val | Gly | Asn | Ile | Lys | Asp |
|     |     |     | 180 |     |     |     |     | 185 |     |     |     | 190 |     |     |     |

| Val | Gln | Glu | Phe | Arg | Arg | Ile | Ile | Glu | Glu | Met | Asp | Arg | Gln | Glu |
|     |     | 195 |     |     |     |     | 200 |     |     |     |     | 205 |     |     |

| Lys | Arg | Tyr | Leu | Ile | Asp | Cys | Glu | Val | Glu | Arg | Ile | Asn | Thr | Ile | Leu |
|     | 210 |     |     |     |     | 215 |     |     |     |     | 220 |     |     |     |     |

| Glu | Gln | Val | Val | Ile | Leu | Gly | Lys | His | Ser | Arg | Gly | Tyr | His | Tyr | Met |
| 225 |     |     |     |     | 230 |     |     |     |     | 235 |     |     |     |     | 240 |

| Leu | Ala | Asn | Leu | Gly | Phe | Thr | Asp | Ile | Leu | Leu | Glu | Arg | Val | Met | His |
|     |     |     |     | 245 |     |     |     |     | 250 |     |     |     |     | 255 |     |

| Gly | Gly | Ala | Asn | Ile | Thr | Gly | Phe | Gln | Ile | Val | Asn | Asn | Glu | Asn | Pro |
|     |     |     | 260 |     |     |     |     | 265 |     |     |     |     | 270 |     |     |

| Met | Val | Gln | Gln | Phe | Ile | Gln | Arg | Trp | Val | Arg | Leu | Asp | Glu | Arg | Glu |
|     |     | 275 |     |     |     |     | 280 |     |     |     |     | 285 |     |     |     |

| Phe | Pro | Glu | Ala | Lys | Asn | Ala | Pro | Leu | Lys | Tyr | Thr | Ser | Ala | Leu | Thr |
|     | 290 |     |     |     |     | 295 |     |     |     |     | 300 |     |     |     |     |

| His | Asp | Ala | Ile | Leu | Val | Ile | Ala | Glu | Ala | Phe | Arg | Tyr | Leu | Arg | Arg |
| 305 |     |     |     |     | 310 |     |     |     |     | 315 |     |     |     |     | 320 |

| Gln | Arg | Val | Asp | Val | Ser | Arg | Arg | Gly | Ser | Ala | Gly | Asp | Cys | Leu | Ala |
|     |     |     |     | 325 |     |     |     |     | 330 |     |     |     |     | 335 |     |

| Asn | Pro | Ala | Val | Pro | Trp | Ser | Gln | Gly | Ile | Asp | Ile | Glu | Arg | Ala | Leu |
|     |     |     | 340 |     |     |     |     | 345 |     |     |     |     | 350 |     |     |

| Lys | Met | Val | Gln | Val | Gln | Gly | Met | Thr | Gly | Asn | Ile | Gln | Phe | Asp | Thr |
|     |     | 355 |     |     |     |     | 360 |     |     |     |     | 365 |     |     |     |

| Tyr | Gly | Arg | Arg | Thr | Asn | Tyr | Thr | Ile | Asp | Val | Tyr | Glu | Met | Lys | Val |
|     | 370 |     |     |     |     | 375 |     |     |     |     | 380 |     |     |     |     |

| Ser | Gly | Ser | Arg | Lys | Ala | Gly | Tyr | Trp | Asn | Glu | Tyr | Glu | Arg | Phe | Val |
| 385 |     |     |     |     | 390 |     |     |     |     | 395 |     |     |     |     | 400 |

| Pro | Phe | Ser | Asp | Gln | Gln | Ile | Ser | Asn | Asp | Ser | Ala | Ser | Ser | Glu | Asn |
|     |     |     |     | 405 |     |     |     |     | 410 |     |     |     |     | 415 |     |

| Arg | Thr | Ile | Val | Val | Thr | Thr | Ile | Leu | Glu | Ser | Pro | Tyr | Val | Met | Tyr |
|     |     |     | 420 |     |     |     |     | 425 |     |     |     |     | 430 |     |     |

| Lys | Lys | Asn | His | Glu | Gln | Leu | Glu | Gly | Asn | Glu | Arg | Tyr | Glu | Gly | Tyr |
|     |     | 435 |     |     |     |     | 440 |     |     |     |     | 445 |     |     |     |

| Cys | Val | Asp | Leu | Ala | Tyr | Glu | Ile | Ala | Lys | His | Val | Arg | Ile | Lys | Tyr |
|     | 450 |     |     |     |     | 455 |     |     |     |     | 460 |     |     |     |     |

| Lys | Leu | Ser | Ile | Val | Gly | Asp | Gly | Lys | Tyr | Gly | Ala | Arg | Asp | Pro | Glu |
| 465 |     |     |     |     | 470 |     |     |     |     | 475 |     |     |     |     | 480 |

| Thr | Lys | Ile | Trp | Asn | Gly | Met | Val | Gly | Glu | Leu | Val | Tyr | Gly | Arg | Ala |
|     |     |     |     | 485 |     |     |     |     | 490 |     |     |     |     | 495 |     |

| Asp | Ile | Ala | Val | Ala | Pro | Leu | Thr | Ile | Thr | Leu | Val | Arg | Glu | Glu | Val |
|     |     |     | 500 |     |     |     |     | 505 |     |     |     |     | 510 |     |     |

| Ile | Asp | Phe | Ser | Lys | Pro | Phe | Met | Ser | Leu | Gly | Ile | Ser | Ile | Met | Ile |
|     |     | 515 |     |     |     |     | 520 |     |     |     |     | 525 |     |     |     |

| Lys | Lys | Pro | Gln | Lys | Ser | Lys | Pro | Gly | Val | Phe | Ser | Phe | Leu | Asp | Pro |
|     |     | 530 |     |     |     |     | 535 |     |     |     |     | 540 |     |     |     |

| Leu | Ala | Tyr | Glu | Ile | Trp | Met | Cys | Ile | Val | Phe | Ala | Tyr | Ile | Gly | Val |
| 545 |     |     |     |     | 550 |     |     |     |     | 555 |     |     |     |     | 560 |

| Ser | Val | Val | Leu | Phe | Leu | Val | Ser | Arg | Phe | Ser | Pro | Tyr | Glu | Trp | His |
|     |     |     |     | 565 |     |     |     |     | 570 |     |     |     |     | 575 |     |

| Leu | Glu | Asp | Asn | Asn | Glu | Glu | Pro | Arg | Asp | Pro | Gln | Ser | Pro | Pro | Asp |
|     |     |     | 580 |     |     |     |     | 585 |     |     |     |     | 590 |     |     |

| Pro | Pro | Asn | Glu | Phe | Gly | Ile | Phe | Asn | Ser | Leu | Trp | Phe | Ser | Leu | Gly |
|     |     |     | 595 |     |     |     |     | 600 |     |     |     |     | 605 |     |     |

| | | | | | | | | | | | | | | |
|---|---|---|---|---|---|---|---|---|---|---|---|---|---|---|
| Ala | Phe | Met | Gln | Gln | Gly | Cys | Asp | Ile | Ser | Pro | Arg | Ser | Leu | Ser | Gly |
| 610 | | | | | 615 | | | | | 620 | | | | | |
| Arg | Ile | Val | Gly | Gly | Val | Trp | Trp | Phe | Phe | Thr | Leu | Ile | Ile | Ile | Ser |
| 625 | | | | 630 | | | | | 635 | | | | | 640 | |
| Ser | Tyr | Thr | Ala | Asn | Leu | Ala | Ala | Phe | Leu | Thr | Val | Glu | Arg | Met | Val |
| | | | | 645 | | | | | 650 | | | | | 655 | |
| Ser | Pro | Ile | Glu | Ser | Ala | Glu | Asp | Leu | Ala | Lys | Gln | Thr | Glu | Ile | Ala |
| | | | 660 | | | | | 665 | | | | | 670 | | |
| Tyr | Gly | Thr | Leu | Asp | Ser | Gly | Ser | Thr | Lys | Glu | Phe | Phe | Arg | Arg | Ser |
| | | 675 | | | | | 680 | | | | | 685 | | | |
| Lys | Ile | Ala | Val | Tyr | Glu | Lys | Met | Trp | Ser | Tyr | Met | Lys | Ser | Ala | Glu |
| | 690 | | | | | 695 | | | | | 700 | | | | |
| Pro | Ser | Val | Phe | Thr | Lys | Thr | Thr | Ala | Asp | Gly | Val | Ala | Arg | Val | Arg |
| 705 | | | | | 710 | | | | | 715 | | | | | 720 |
| Lys | Ser | Lys | Gly | Lys | Phe | Ala | Phe | Leu | Leu | Glu | Ser | Thr | Met | Asn | Glu |
| | | | | 725 | | | | | 730 | | | | | 735 | |
| Tyr | Ile | Glu | Gln | Arg | Lys | Pro | Cys | Asp | Thr | Met | Lys | Val | Gly | Gly | Asn |
| | | | 740 | | | | | 745 | | | | | 750 | | |
| Leu | Asp | Ser | Lys | Gly | Tyr | Gly | Val | Ala | Thr | Pro | Lys | Gly | Ser | Ala | Leu |
| | | 755 | | | | | 760 | | | | | 765 | | | |
| Gly | Asn | Ala | Val | Asn | Leu | Ala | Val | Leu | Lys | Leu | Asn | Glu | Gln | Gly | Leu |
| | 770 | | | | | 775 | | | | | 780 | | | | |
| Leu | Asp | Lys | Leu | Lys | Asn | Lys | Trp | Trp | Tyr | Asp | Lys | Gly | Glu | Cys | Gly |
| 785 | | | | | 790 | | | | | 795 | | | | | 800 |
| Ser | Gly | Gly | Gly | Asp | Ser | Lys | Asp | Lys | Thr | Ser | Ala | Leu | Ser | Leu | Ser |
| | | | | 805 | | | | | 810 | | | | | 815 | |
| Asn | Val | Ala | Gly | Val | Phe | Tyr | Ile | Leu | Val | Gly | Gly | Leu | Gly | Leu | Ala |
| | | | 820 | | | | | 825 | | | | | 830 | | |
| Met | Met | Val | Ala | Leu | Ile | Glu | Phe | Cys | Tyr | Lys | Ser | Arg | Ala | Glu | Ser |
| | | 835 | | | | | 840 | | | | | 845 | | | |
| Lys | Arg | Met | Lys | Leu | Thr | Lys | Asn | Thr | Gln | Asn | Phe | Lys | Pro | Ala | Pro |
| 850 | | | | | 855 | | | | | 860 | | | | | |
| Ala | Thr | Asn | Thr | Gln | Asn | Tyr | Ala | Thr | Tyr | Arg | Glu | Gly | Tyr | Asn | Val |
| 865 | | | | 870 | | | | | 875 | | | | | 880 | |
| Tyr | Gly | Thr | Glu | Ser | Val | Lys | Ile | | | | | | | | |
| | | | | 885 | | | | | | | | | | | |

(2) INFORMATION FOR SEQ ID NO: 13:

(i) SEQUENCE CHARACTERISTICS:
        (A) LENGTH: 1191 base pairs
        (B) TYPE: nucleic acid
        (C) STRANDEDNESS: single
        (D) TOPOLOGY: linear (ii) MOLECULE TYPE: cDNA to mRNA (vi) ORIGINAL SOURCE:
        (A) ORGANISM: Homo sapiens
        (B) DEVELOPMENTAL STAGE: adult
        (C) TISSUE TYPE: brain (ix) FEATURE:
        (A) NAME/KEY: CDS
        (B) LOCATION: 317..1191

(xi) SEQUENCE DESCRIPTION: SEQ ID NO: 13:

```
CGGGTCCTGA CAGCCCCTTG GCCTCCCAGC ATGGGGAAGC GTGAGGAGTT GCCCAGCAGT      60

GAGCAGCCCC CCTCACTCCT GGCCCCATGA GCCGCAGCCA CAGGCAGCAG AGGAGGGCTA     120
```

-continued

```
AGGAGAACTA GTCATAATCT TAAACCACCG AAACCTCTTT CCTTTTTTTT CTTTCTTTTC    180

TTTCTTTTCT TTTTTTTTTT TTTTTTTGG TTGATTTTAA TTTTAGCGCC ATCGTCTTCA    240

ATGCTTCTCT GAACAGCCTT TAGGAAGAGT GCGAGAGAAA GAGAGAGAGC GCGCGCCAGG    300

GAGAGGAGAA AAGAAG ATG AGG ATT ATT TCC AGA CAG ATT GTC TTG TTA       349
               Met Arg Ile Ile Ser Arg Gln Ile Val Leu Leu
                1                 5                      10

TTT TCT GGA TTT TGG GGA CTC GCC ATG GGA GCC TTT CCG AGC AGC GTG    397
Phe Ser Gly Phe Trp Gly Leu Ala Met Gly Ala Phe Pro Ser Ser Val
             15              20                  25

CAA ATA GGT GGT CTC TTC ATC CGA AAC ACA GAT CAG GAA TAC ACT GCT    445
Gln Ile Gly Gly Leu Phe Ile Arg Asn Thr Asp Gln Glu Tyr Thr Ala
         30              35                  40

TTT CGA TTA GCA ATT TTT CTT CAT AAC ACC AGC CCC AAT GCG TCG GAA    493
Phe Arg Leu Ala Ile Phe Leu His Asn Thr Ser Pro Asn Ala Ser Glu
     45              50                  55

GCT CCT TTT AAT TTG GTA CCT CAT GTG GAC AAC ATT GAG ACA GCC AAC    541
Ala Pro Phe Asn Leu Val Pro His Val Asp Asn Ile Glu Thr Ala Asn
 60              65                  70                      75

AGT TTT GCT GTA ACA AAC GCC TTC TGT TCC CAG TAT TCT AGA GGA GTA    589
Ser Phe Ala Val Thr Asn Ala Phe Cys Ser Gln Tyr Ser Arg Gly Val
             80                  85                  90

TTT GCC ATT TTT GGA CTC TAT GAT AAG AGG TCG GTA CAT ACC TTG ACC    637
Phe Ala Ile Phe Gly Leu Tyr Asp Lys Arg Ser Val His Thr Leu Thr
             95                  100                 105

TCA TTC TGC AGC GCC TTA CAT ATC TCC CTC ATC ACA CCA AGT TTC CCT    685
Ser Phe Cys Ser Ala Leu His Ile Ser Leu Ile Thr Pro Ser Phe Pro
         110                 115                 120

ACT GAG GGG GAG AGC CAG TTT GTG CTG CAA CTA AGA CCT TCG TTA CGA    733
Thr Glu Gly Glu Ser Gln Phe Val Leu Gln Leu Arg Pro Ser Leu Arg
     125                 130                 135

GGA GCA CTC TTG AGT TTG CTG GAT CAC TAC GAA TGG AAC TGT TTT GTC    781
Gly Ala Leu Leu Ser Leu Leu Asp His Tyr Glu Trp Asn Cys Phe Val
 140                 145                 150                 155

TTC CTG TAT GAC ACA GAC AGG GGA TAC TCG ATA CTC CAA GCT ATT TTG    829
Phe Leu Tyr Asp Thr Asp Arg Gly Tyr Ser Ile Leu Gln Ala Ile Leu
             160                 165                 170

GAA AAA GCA GGA CAA AAT GGT TGG CAT GTC AGC GCT ATA TGT GTG GAA    877
Glu Lys Ala Gly Gln Asn Gly Trp His Val Ser Ala Ile Cys Val Glu
             175                 180                 185

AAT TTT AAT GAT GTC AGC TAT AGG CAA CTT CTA GAA GAA CTT GAC AGA    925
Asn Phe Asn Asp Val Ser Tyr Arg Gln Leu Leu Glu Glu Leu Asp Arg
         190                 195                 200

AGA CAA GAG AAG AAG TTT GTA ATA GAC TGT GAG ATA GAG AGA CTT CAA    973
Arg Gln Glu Lys Lys Phe Val Ile Asp Cys Glu Ile Glu Arg Leu Gln
 205                 210                 215

AAC ATA TTA GAA CAG ATT GTA AGT GTT GGA AAG CAT GTT AAA GGC TAC    1021
Asn Ile Leu Glu Gln Ile Val Ser Val Gly Lys His Val Lys Gly Tyr
 220                 225                 230                 235

CAT TAT ATC ATT GCA AAC TTG GGA TTC AAG GAT ATT TCT CTT GAG AGG    1069
His Tyr Ile Ile Ala Asn Leu Gly Phe Lys Asp Ile Ser Leu Glu Arg
             240                 245                 250

TTT ATA CAT GGT GGA GCC AAT GTT ACT GGA TTC CAG TTG GTG GAT TTT    1117
Phe Ile His Gly Gly Ala Asn Val Thr Gly Phe Gln Leu Val Asp Phe
             255                 260                 265

AAT ACA CCT ATG GTA ATC AAA CTA ATG GAT CGC TGG AAG AAA CTA GAT    1165
Asn Thr Pro Met Val Ile Lys Leu Met Asp Arg Trp Lys Lys Leu Asp
         270                 275                 280

CAG AGA GAG TAT CCA GGA TCT GAG CC                                  1191
```

```
Gln  Arg  Glu  Tyr  Pro  Gly  Ser  Glu
     285                 290
```

( 2 ) INFORMATION FOR SEQ ID NO:14:

( i ) SEQUENCE CHARACTERISTICS:
        ( A ) LENGTH: 291 amino acids
        ( B ) TYPE: amino acid
        ( D ) TOPOLOGY: linear ( i i ) MOLECULE TYPE: protein ( x i ) SEQUENCE DESCRIPTION: SEQ ID NO: 14:

```
Met  Arg  Ile  Ile  Ser  Arg  Gln  Ile  Val  Leu  Leu  Phe  Ser  Gly  Phe  Trp
 1             5                      10                       15

Gly  Leu  Ala  Met  Gly  Ala  Phe  Pro  Ser  Ser  Val  Gln  Ile  Gly  Gly  Leu
              20                      25                       30

Phe  Ile  Arg  Asn  Thr  Asp  Gln  Glu  Tyr  Thr  Ala  Phe  Arg  Leu  Ala  Ile
              35                      40                  45

Phe  Leu  His  Asn  Thr  Ser  Pro  Asn  Ala  Ser  Glu  Ala  Pro  Phe  Asn  Leu
         50                 55                       60

Val  Pro  His  Val  Asp  Asn  Ile  Glu  Thr  Ala  Asn  Ser  Phe  Ala  Val  Thr
 65                      70                  75                           80

Asn  Ala  Phe  Cys  Ser  Gln  Tyr  Ser  Arg  Gly  Val  Phe  Ala  Ile  Phe  Gly
                   85                      90                            95

Leu  Tyr  Asp  Lys  Arg  Ser  Val  His  Thr  Leu  Thr  Ser  Phe  Cys  Ser  Ala
               100                     105                  110

Leu  His  Ile  Ser  Leu  Ile  Thr  Pro  Ser  Phe  Pro  Thr  Glu  Gly  Glu  Ser
          115                     120                 125

Gln  Phe  Val  Leu  Gln  Leu  Arg  Pro  Ser  Leu  Arg  Gly  Ala  Leu  Leu  Ser
     130                     135                 140

Leu  Leu  Asp  His  Tyr  Glu  Trp  Asn  Cys  Phe  Val  Phe  Leu  Tyr  Asp  Thr
145                      150                     155                      160

Asp  Arg  Gly  Tyr  Ser  Ile  Leu  Gln  Ala  Ile  Leu  Glu  Lys  Ala  Gly  Gln
               165                     170                 175

Asn  Gly  Trp  His  Val  Ser  Ala  Ile  Cys  Val  Glu  Asn  Phe  Asn  Asp  Val
              180                     185                     190

Ser  Tyr  Arg  Gln  Leu  Leu  Glu  Glu  Leu  Asp  Arg  Arg  Gln  Glu  Lys  Lys
          195                     200                 205

Phe  Val  Ile  Asp  Cys  Glu  Ile  Glu  Arg  Leu  Gln  Asn  Ile  Leu  Glu  Gln
     210                     215                 220

Ile  Val  Ser  Val  Gly  Lys  His  Val  Lys  Gly  Tyr  His  Tyr  Ile  Ile  Ala
225                      230                 235                           240

Asn  Leu  Gly  Phe  Lys  Asp  Ile  Ser  Leu  Glu  Arg  Phe  Ile  His  Gly  Gly
               245                     250                     255

Ala  Asn  Val  Thr  Gly  Phe  Gln  Leu  Val  Asp  Phe  Asn  Thr  Pro  Met  Val
              260                     265                 270

Ile  Lys  Leu  Met  Asp  Arg  Trp  Lys  Lys  Leu  Asp  Gln  Arg  Glu  Tyr  Pro
          275                     280                 285

Gly  Ser  Glu
     290
```

( 2 ) INFORMATION FOR SEQ ID NO: 15:

( i ) SEQUENCE CHARACTERISTICS:
        ( A ) LENGTH: 1191 base pairs
        ( B ) TYPE: nucleic acid
        ( C ) STRANDEDNESS: single
        ( D ) TOPOLOGY: linear ( i i ) MOLECULE TYPE: cDNA to mRNA ( v i ) ORIGINAL SOURCE:
    ( A ) ORGANISM: Homo sapiens
    ( B ) DEVELOPMENTAL STAGE: adult
    ( C ) TISSUE TYPE: brain ( i x ) FEATURE:
    ( A ) NAME/KEY: CDS
    ( B ) LOCATION: 317..1191

( x i ) SEQUENCE DESCRIPTION: SEQ ID NO: 15:

```
CGGGTCCTGA  CAGCCCCTTG  GCCTCCAGC   ATGGGGAAGC  GTGAGGAGTT  GCCCAGCAGT       60

GAGCAGCCCC  CCTCACTCCT  GGCCCCATGA  GCCGCAGCCA  CAGGCAGCAG  AGGAGGGCTA      120

AGGAGAACTA  GTCATAATCT  TAAACCACCG  AAACCTCTTT  CCTTTTTTT   CTTTCTTTTC      180

TTTCTTTTCT  TTTTTTTTT   TTTTTTTGG   TTGATTTTAA  TTTTAGCGCC  ATCGTCTTCA      240

ATGCTTCTCT  GAACAGCCTT  TAGGAAGAGT  GCGAGAGAAA  GAGAGAGAGC  GCGCGCCAGG      300

GAGAGGAGAA  AAGAAG ATG AGG ATT ATT TCC AGA CAG ATT GTC TTG TTA             349
                   Met Arg Ile Ile Ser Arg Gln Ile Val Leu Leu
                    1               5                      10

TTT TCT GGA TTT TGG GGA CTC GCC ATG GGA GCC TTT CCG AGC AGC GTG            397
Phe Ser Gly Phe Trp Gly Leu Ala Met Gly Ala Phe Pro Ser Ser Val
            15                  20                  25

CAA ATA GGT GGT CTC TTC ATC CGA AAC ACA GAT CAG GAA TAC ACT GCT            445
Gln Ile Gly Gly Leu Phe Ile Arg Asn Thr Asp Gln Glu Tyr Thr Ala
        30                  35                  40

TTT CGA TTA GCA ATT TTT CTT CAT AAC ACC AGC CCC AAT GCG TCG GAA            493
Phe Arg Leu Ala Ile Phe Leu His Asn Thr Ser Pro Asn Ala Ser Glu
    45                  50                  55

GCT CCT TTT AAT TTG GTA CCT CAT GTG GAC AAC ATT GAG ACA GCC AAC            541
Ala Pro Phe Asn Leu Val Pro His Val Asp Asn Ile Glu Thr Ala Asn
60                  65                  70                  75

AGT TTT GCT GTA ACA AAC GCC TTC TGT TCC CAG TAT TCT AGA GGA GTA            589
Ser Phe Ala Val Thr Asn Ala Phe Cys Ser Gln Tyr Ser Arg Gly Val
                80                  85                  90

TTT GCC ATT TTT GGA CTC TAT GAT AAG AGG TCG GTA CAT ACC TTG ACC            637
Phe Ala Ile Phe Gly Leu Tyr Asp Lys Arg Ser Val His Thr Leu Thr
            95                  100                 105

TCA TTC TGC AGC GCC TTA CAT ATC TCC CTC ATC ACA CCA AGT TTC CCT            685
Ser Phe Cys Ser Ala Leu His Ile Ser Leu Ile Thr Pro Ser Phe Pro
        110                 115                 120

ACT GAG GGG GAG AGC CAG TTT GTG CTG CAA CTA AGA CCT TCG TTA CGA            733
Thr Glu Gly Glu Ser Gln Phe Val Leu Gln Leu Arg Pro Ser Leu Arg
    125                 130                 135

GGA GCA CTC TTG AGT TTG CTG GAT CAC TAC GAA TGG AAC TGT TTT GTC            781
Gly Ala Leu Leu Ser Leu Leu Asp His Tyr Glu Trp Asn Cys Phe Val
140                 145                 150                 155

TTC CTG TAT GAC ACA GAC AGG GGA TAC TCG ATA CTC CAA GCT ATT TTG            829
Phe Leu Tyr Asp Thr Asp Arg Gly Tyr Ser Ile Leu Gln Ala Ile Leu
                160                 165                 170

GAA AAA GCA GGA CAA AAT GGT TGG CAT GTC AGC GCT ATA TGT GTG GAA            877
Glu Lys Ala Gly Gln Asn Gly Trp His Val Ser Ala Ile Cys Val Glu
            175                 180                 185

AAT TTT AAT GAT GTC AGC TAT AGG CAA CTT CTA GAA GAA CTT GAC AGA            925
Asn Phe Asn Asp Val Ser Tyr Arg Gln Leu Leu Glu Glu Leu Asp Arg
        190                 195                 200

AGA CAA GAG AAG AAG TTT GTA ATA GAC TGT GAG ATA GAG AGA CTT CAA            973
Arg Gln Glu Lys Lys Phe Val Ile Asp Cys Glu Ile Glu Arg Leu Gln
    205                 210                 215
```

```
AAC ATA TTA GAA CAG ATT GTA AGT GTT GGA AAG CAT GTT AAA GGC TAC     1021
Asn Ile Leu Glu Gln Ile Val Ser Val Gly Lys His Val Lys Gly Tyr
220             225             230             235

CAT TAT ATC ATT GCA AAC TTG GGA TTC AAG GAT ATT TCT CTT GAG AGG     1069
His Tyr Ile Ile Ala Asn Leu Gly Phe Lys Asp Ile Ser Leu Glu Arg
            240             245             250

TTT ATA CAT GGT GGA GCC AAT GTT ACT GGA TTC CAG TTG GTG GAT TTT     1117
Phe Ile His Gly Gly Ala Asn Val Thr Gly Phe Gln Leu Val Asp Phe
                255             260             265

AAT ACA CCT ATG GTA ATC AAA CTA ATG GAT CGC TGG AAG AAA CTA GAT     1165
Asn Thr Pro Met Val Ile Lys Leu Met Asp Arg Trp Lys Lys Leu Asp
        270             275             280

CAG AGA GAG TAT CCA GGA TCT GAG CC                                   1191
Gln Arg Glu Tyr Pro Gly Ser Glu
285             290
```

( 2 ) INFORMATION FOR SEQ ID NO: 16:

( i ) SEQUENCE CHARACTERISTICS:
        ( A ) LENGTH: 291 amino acids
        ( B ) TYPE: amino acid
        ( D ) TOPOLOGY: linear ( i i ) MOLECULE TYPE: protein ( x i ) SEQUENCE DESCRIPTION: SEQ ID NO: 16:

```
Met Arg Ile Ile Ser Arg Gln Ile Val Leu Leu Phe Ser Gly Phe Trp
1               5               10              15

Gly Leu Ala Met Gly Ala Phe Pro Ser Ser Val Gln Ile Gly Gly Leu
            20              25              30

Phe Ile Arg Asn Thr Asp Gln Glu Tyr Thr Ala Phe Arg Leu Ala Ile
        35              40              45

Phe Leu His Asn Thr Ser Pro Asn Ala Ser Glu Ala Pro Phe Asn Leu
    50              55              60

Val Pro His Val Asp Asn Ile Glu Thr Ala Asn Ser Phe Ala Val Thr
65              70              75              80

Asn Ala Phe Cys Ser Gln Tyr Ser Arg Gly Val Phe Ala Ile Phe Gly
            85              90              95

Leu Tyr Asp Lys Arg Ser Val His Thr Leu Thr Ser Phe Cys Ser Ala
        100             105             110

Leu His Ile Ser Leu Ile Thr Pro Ser Phe Pro Thr Glu Gly Glu Ser
    115             120             125

Gln Phe Val Leu Gln Leu Arg Pro Ser Leu Arg Gly Ala Leu Leu Ser
    130             135             140

Leu Leu Asp His Tyr Glu Trp Asn Cys Phe Val Phe Leu Tyr Asp Thr
145             150             155             160

Asp Arg Gly Tyr Ser Ile Leu Gln Ala Ile Leu Glu Lys Ala Gly Gln
            165             170             175

Asn Gly Trp His Val Ser Ala Ile Cys Val Glu Asn Phe Asn Asp Val
        180             185             190

Ser Tyr Arg Gln Leu Leu Glu Glu Leu Asp Arg Arg Gln Glu Lys Lys
    195             200             205

Phe Val Ile Asp Cys Glu Ile Glu Arg Leu Gln Asn Ile Leu Glu Gln
    210             215             220

Ile Val Ser Val Gly Lys His Val Lys Gly Tyr His Tyr Ile Ile Ala
225             230             235             240

Asn Leu Gly Phe Lys Asp Ile Ser Leu Glu Arg Phe Ile His Gly Gly
            245             250             255
```

| Ala | Asn | Val | Thr | Gly | Phe | Gln | Leu | Val | Asp | Phe | Asn | Thr | Pro | Met | Val |
|---|---|---|---|---|---|---|---|---|---|---|---|---|---|---|---|
| | | | 260 | | | | 265 | | | | | 270 | | | |

| Ile | Lys | Leu | Met | Asp | Arg | Trp | Lys | Lys | Leu | Asp | Gln | Arg | Glu | Tyr | Pro |
|---|---|---|---|---|---|---|---|---|---|---|---|---|---|---|---|
| | 275 | | | | | 280 | | | | | 285 | | | | |

| Gly | Ser | Glu |
|---|---|---|
| 290 | | |

( 2 ) INFORMATION FOR SEQ ID NO: 17:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: genomic DNA ( x i ) SEQUENCE DESCRIPTION: SEQ ID NO: 17:

ATCTATGATT GGACCTGGGC                                            20

( 2 ) INFORMATION FOR SEQ ID NO: 18:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( i i ) MOLECULE TYPE: genomic DNA ( x i ) SEQUENCE DESCRIPTION: SEQ ID NO: 18:

ACATCTGCTC TTCCATAGAC CAGC                                  24

( 2 ) INFORMATION FOR SEQ ID NO: 19:

( i ) SEQUENCE CHARACTERISTICS:
        ( A ) LENGTH: 39 base pairs
        ( B ) TYPE: nucleic acid
        ( C ) STRANDEDNESS: single
        ( D ) TOPOLOGY: linear ( i i ) MOLECULE TYPE: genomic DNA ( x i ) SEQUENCE DESCRIPTION: SEQ ID NO: 19:

TGCGATAAGC TTATGCAGCA CATTTTTGCC TTCTTCTGC                39

( 2 ) INFORMATION FOR SEQ ID NO: 20:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( i i ) MOLECULE TYPE: genomic DNA ( x i ) SEQUENCE DESCRIPTION: SEQ ID NO: 20:

ATGCCATTCC AGGCCTTCGT GTCA                                  24

( 2 ) INFORMATION FOR SEQ ID NO: 21:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: genomic DNA ( x i ) SEQUENCE DESCRIPTION: SEQ ID NO: 21:

GATGGAAAAT ACGGAGCCCG A                                             21

( 2 ) INFORMATION FOR SEQ ID NO: 22:

( i ) SEQUENCE CHARACTERISTICS:
      ( A ) LENGTH: 21 base pairs
      ( B ) TYPE: nucleic acid
      ( C ) STRANDEDNESS: single
      ( D ) TOPOLOGY: linear ( i i ) MOLECULE TYPE: genomic DNA ( x i ) SEQUENCE DESCRIPTION: SEQ ID NO: 22:

GCTGGGGAGC CGAGCCTGCT C                                             21

( 2 ) INFORMATION FOR SEQ ID NO: 23:

( i ) SEQUENCE CHARACTERISTICS:
      ( A ) LENGTH: 24 base pairs
      ( B ) TYPE: nucleic acid
      ( C ) STRANDEDNESS: single
      ( D ) TOPOLOGY: linear ( i i ) MOLECULE TYPE: genomic DNA ( x i ) SEQUENCE DESCRIPTION: SEQ ID NO: 23:

TGACACGAAG GCCTGGAATG GCAT                                          24

( 2 ) INFORMATION FOR SEQ ID NO: 24:

( i ) SEQUENCE CHARACTERISTICS:
      ( A ) LENGTH: 39 base pairs
      ( B ) TYPE: nucleic acid
      ( C ) STRANDEDNESS: single
      ( D ) TOPOLOGY: linear ( i i ) MOLECULE TYPE: genomic DNA ( x i ) SEQUENCE DESCRIPTION: SEQ ID NO: 24:

TGCGATGAAT TCTTACAATC CCGTGGCTCC CAAGGGCAT                          39

( 2 ) INFORMATION FOR SEQ ID NO: 25:

( i ) SEQUENCE CHARACTERISTICS:
      ( A ) LENGTH: 22 base pairs
      ( B ) TYPE: nucleic acid
      ( C ) STRANDEDNESS: single
      ( D ) TOPOLOGY: linear ( i i ) MOLECULE TYPE: genomic DNA ( x i ) SEQUENCE DESCRIPTION: SEQ ID NO: 25:

TACTTGGGTC TCTTCCAGTC CA                                            22

( 2 ) INFORMATION FOR SEQ ID NO: 26:

( i ) SEQUENCE CHARACTERISTICS:
      ( A ) LENGTH: 24 base pairs
      ( B ) TYPE: nucleic acid
      ( C ) STRANDEDNESS: single
      ( D ) TOPOLOGY: linear ( i i ) MOLECULE TYPE: genomic DNA ( x i ) SEQUENCE DESCRIPTION: SEQ ID NO: 26:

TGTGTGGTCT CGAGCATCAC TATT                                          24